(12) United States Patent
Choi et al.

(10) Patent No.: US 9,595,683 B2
(45) Date of Patent: Mar. 14, 2017

(54) ORGANOMETALLIC COMPOUNDS AND ORGANIC LIGHT EMITTING DEVICES INCLUDING THE SAME

(71) Applicant: Samsung Display Co., Ltd., Yongin (KR)

(72) Inventors: Jong-Won Choi, Yongin (KR); Yoon-Hyun Kwak, Yongin (KR); Bum-Woo Park, Yongin (KR); Sun-Young Lee, Yongin (KR); Wha-Il Choi, Yongin (KR); So-Yeon Kim, Yongin (KR); Ji-Youn Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 648 days.

(21) Appl. No.: 13/801,092

(22) Filed: Mar. 13, 2013

(65) Prior Publication Data

US 2014/0117318 A1    May 1, 2014

(30) Foreign Application Priority Data

Oct. 29, 2012   (KR) .................. 10-2012-0120614

(51) Int. Cl.
| | |
|---|---|
| H01L 51/54 | (2006.01) |
| C09K 11/06 | (2006.01) |
| H01L 51/00 | (2006.01) |
| C07F 15/00 | (2006.01) |
| C07D 401/04 | (2006.01) |
| H01L 51/50 | (2006.01) |

(52) U.S. Cl.
CPC ........ H01L 51/0085 (2013.01); C07D 401/04 (2013.01); C07F 15/002 (2013.01); C07F 15/0033 (2013.01); C07F 15/0086 (2013.01); C07F 15/0093 (2013.01); C09K 11/06 (2013.01); H01L 51/0087 (2013.01); H01L 51/0088 (2013.01); C09K 2211/1044 (2013.01); C09K 2211/185 (2013.01); H01L 51/5016 (2013.01); H01L 2251/308 (2013.01)

(58) Field of Classification Search
None
See application file for complete search history.

(56) References Cited

U.S. PATENT DOCUMENTS

| | | | |
|---|---|---|---|
| 6,465,115 | B2 | 10/2002 | Shi et al. |
| 6,596,415 | B2 | 7/2003 | Shi et al. |
| 7,002,013 | B1 | 2/2006 | Chi et al. |
| 7,329,898 | B2 | 2/2008 | Igarashi |
| 7,759,490 | B2 | 7/2010 | Tao et al. |
| 7,868,170 | B2 | 1/2011 | Chi et al. |
| 2001/0019782 | A1 | 9/2001 | Igarashi et al. |
| 2002/0134984 | A1 | 9/2002 | Igarashi |
| 2006/0182992 | A1 | 8/2006 | Nii et al. |
| 2009/0039776 | A1 | 2/2009 | Yamada et al. |

FOREIGN PATENT DOCUMENTS

| | | |
|---|---|---|
| JP | 2000-003782 A | 1/2000 |
| JP | 2003-133074 A | 5/2003 |
| JP | 2005-310733 A | 11/2005 |
| JP | 2009-40728 A | 2/2009 |

OTHER PUBLICATIONS

Liu et al., "Effects of N-Substitution on Phosphorescence Efficiency . . . ", J. Phys. Chem. C, 2012, 116, pp. 26496-26506 (Nov. 29, 2012).*
Kohler et al."Fluorescence and Phosphorescence in Organic Materials", Advanced Engineering Materials, Weinheim, 4, No. 7, 2002, pp. 453-459.
Baldo et al."Very high-efficiency green organic light-emitting devices based on electrophosphorescence", Applied Physics Letters, American Institute of Physics, vol. 75, No. 1, Jul. 5, 1999, pp. 4-6.
Kwong et al."High operational stability of electrophosphorescent devices", Applied Physics Letters, American Institute of Physics, vol. 81, No. 1, Jul. 1, 2002, pp. 162-164.
Lamansky et al."Highly Phosphorescent Bis-Cyclometalated Iridium Complexes: Synthesis, Photophysical Characterization, and Use in Organic Light Emitting Diodes", J. American Chemical Society, vol. 123, No. 18, 2001, pp. 4304-4312.
Lamansky et al."Synthesis and Characterization of Phosphorescent Cyclometalated Iridium Complexes", Inorganic Chemistry, American Chemical Society, vol. 40, No. 7, 2001, pp. 1704-1711.
Baldo et al."Highly efficient phosphorescent emission from organic electroluminescent devices", Letters to nature, Macmillan Publishers, vol. 395, Sep. 10, 1998, pp. 151-154.

* cited by examiner

*Primary Examiner* — Marie R. Yaminitzky
(74) *Attorney, Agent, or Firm* — Robert E. Bushnell, Esq.

(57) ABSTRACT

Organometallic compounds and organic light-emitting devices including the same are provided. Each subject organometallic compound may be a transition metal complex comprising up to seven organic ligands including one to three ligands which are derivatives of one of 2-(pyrazole-3-yl)pyrimidine and 2-(1,2,4-triazol-3-yl)pyrimidine. Organic light-emitting devices including the subject organometallic compounds show lower driving voltages, higher luminences, higher efficiencies and better lifetime characteristics versus organic light-emitting devices including comparative organometallic complexes.

12 Claims, 1 Drawing Sheet

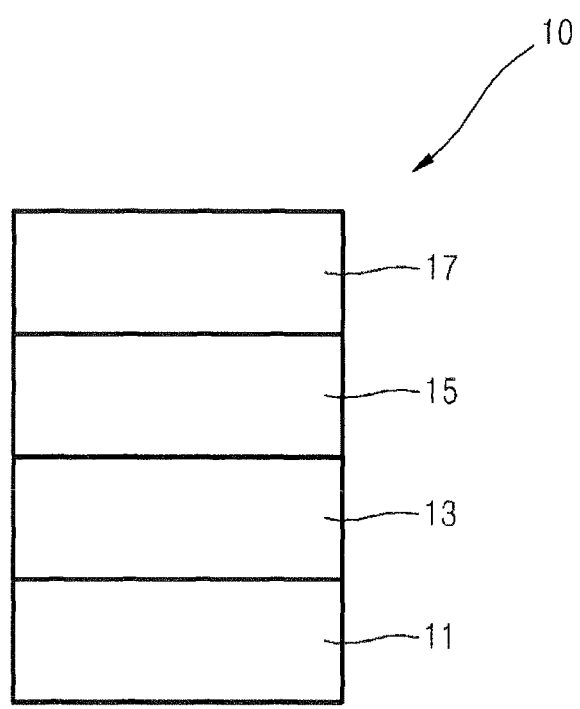

ORGANOMETALLIC COMPOUNDS AND ORGANIC LIGHT EMITTING DEVICES INCLUDING THE SAME

CLAIM OF PRIORITY

This application makes reference to, incorporates the same herein, and claims all benefits accruing under 35 U.S.C. §119 from an application for ORGANOMETALLIC COMPOUNDS AND ORGANIC LIGHT EMITTING DEVICES INCLUDING THE SAME earlier filed in the Korean Intellectual Property Office on 29 Oct. 2012 and there duly assigned Serial No. 10-2012-0120614.

BACKGROUND OF THE INVENTION

Field of the Invention

The present invention relates to compounds for organic light-emitting devices and organic light-emitting devices including the compounds.

Description of the Related Art

Organic light-emitting devices (OLED's), which are self-emitting devices, have advantages such as wide viewing angles, excellent contrast, quick response, high brightness and excellent driving voltage characteristics and can provide multicolored images.

A typical OLED has a structure including a substrate and an anode, a hole transport layer (HTL), an emission layer (EML), an electron transport layer (ETL) and a cathode sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides organometallic compounds having novel structures and organic light-emitting devices including the same.

According to an embodiment of the present invention, there is provided an organometallic compound represented by Formula 1 below:

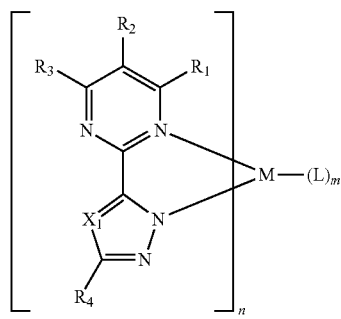

<Formula 1>

M in Formula 1 being a transition metal;
$X_1$ in Formula 1 being N or $C(R_5)$;

$R_1$ to $R_5$ in Formula 1 each being independently one of a hydrogen atom, a deuterium atom, a halogen atom, a hydroxyl group, a cyano group, a nitro group, an amino group, an amidino group, a hydrazine, a hydrazone, carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —$N(Q_1)(Q_2)$, —$Si(Q_3)(Q_4)(Q_5)$, —$C(=O)(Q_6)$ (where $Q_1$ to $Q_6$ are each independently, a hydrogen atom, a substituted or unsubstituted $C_1$-$C_{60}$ alkyl group, a substituted or unsubstituted $C_6$-$C_{60}$ aryl group or a substituted or unsubstituted $C_2$-$C_{60}$ heteroaryl group), or a binding site with an adjacent ligand via a single bond or a divalent linking group, at least two sustituents of $R_1$ to $R_5$ being optionally linked to each other to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group;

n in Formula 1 being an integer from 1 to 3;
L in Formula 1 being an organic ligand; and
m in Formula 1 being an integer from 0 to 4,
where n is 2 or greater, at least two ligands of

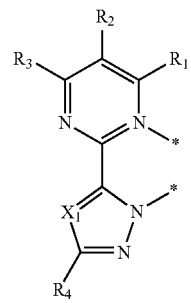

in Formula 1 are identical to or different from each other.

According to another embodiment of the present invention, there is provided an organic light-emitting device including: a substrate; a first electrode; a second electrode disposed opposite to the first electrode; and an organic layer disposed between the first electrode and the second electrode and comprising an emission layer, the organic layer comprising at least one of the organometallic compounds of Formula 1 above.

BRIEF DESCRIPTION OF THE DRAWINGS

These and/or other aspects of the invention will become apparent and more readily appreciated from the following description of the embodiments, taken in conjunction with the accompanying drawings of which:

FIG. 1 is a schematic sectional view of a structure of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided an organometallic compound represented by Formula 1 below:

<Formula 1>

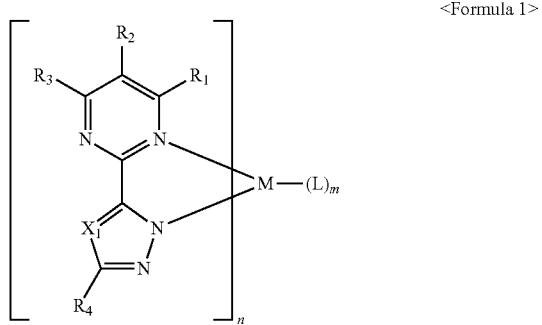

In Formula 1 above, M is a transition metal, which may be, for example, any metal of Group 6, Group 7, Group 8, Group 9, Group 10, or Group 11 of the periodic table of elements.

For example, M in Formula 1 may be one of ruthenium (Ru), rhodium (Rh), palladium (Pd), tungsten (W), rhenium (Re), osmium (Os), iridium (Ir), and platinum (Pt), but is not limited thereto.

In Formula 1, $X_1$ may be one of N and $C(R_5)$.

In Formula 1, $R_1$ to $R_5$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), —C(=O)($Q_6$) (where $Q_1$ to $Q_6$ are each independently, a hydrogen atom, a substituted or unsubstituted $C_1$-$C_{60}$ alkyl group, a substituted or unsubstituted $C_6$-$C_{60}$ aryl group or a substituted or unsubstituted $C_2$-$C_{60}$ heteroaryl group), and a binding site with an adjacent ligand via a single bond or divalent linking group.

In Formula 1, $R_1$ to $R_5$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof; a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group; $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one of a halogen atom, $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a —N($Q_{11}$)($Q_{12}$), and —Si($Q_{13}$)($Q_{14}$)($Q_{15}$) (where $Q_{11}$ to $Q_{15}$ may be each independently, a hydrogen atom, $C_1$-$C_{10}$ alkyl group, a $C_6$-$C_{20}$ aryl group, or a $C_2$-$C_{20}$ heteroaryl group; —N($Q_1$)($Q_2$), —Si($Q_3$)($Q_4$)($Q_5$), and —C(=O)($Q_6$) (where $Q_1$ to $Q_6$ may be each independently a hydrogen atom, $C_1$-$C_{60}$ alkyl group, a $C_6$-$C_{60}$ aryl group or $C_2$-$C_{60}$ heteroaryl group); and a binding site with an adjacent ligand via a single bond or divalent linking group.

For example, in Formula 1, $R_1$ to $R_5$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof; a $C_1$-$C_{20}$ alkyl group, a $C_1$-$C_{20}$ alkoxy group, a cyclopropyl group, a cyclobutyl group, a cyclopentyl group, a cyclohexyl group, a cycloheptyl group, a cyclopentenyl group, a cyclohexcenyl group, a cyclopentadienyl group, a cyclohexadienyl group, a phenyl group, a naphthyl group, an anthryl group, a fluorenyl group, a chrysenyl group, a pyrenyl group, a phenanthrenyl group, a pyrrolyl group, a pyridinyl group, a pyrimidinyl group, a pyrazinyl group, a triazinyl group, a carbazolyl group, an indolyl group, a benzoimidazolyl group, a quinolinyl group, and an isoquinolinyl group; a $C_1$-$C_{20}$ alkyl group, a $C_1$-$C_{20}$ alkoxy group, a cyclopropyl group, a cyclobutyl group, a cyclopentyl group, a cyclohexyl group, a cycloheptyl group, a cyclopentenyl group, a cyclohexcenyl group, a cyclopentadiethyl group, a cyclohexadienyl group, a phenyl group, a naphthyl group, an anthryl group, a fluorenyl group, a chrysenyl group, a pyrenyl group, a phenanthrenyl group, a pyrrolyl group, a pyridinyl group, a pyrimidinyl group, a pyrazinyl group, a triazinyl group, a carbazolyl group, an indolyl group, a benzoimidazolyl group, a quinolinyl group, and an isoquinolinyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$alkyl group, a $C_1$-$C_{20}$alkoxy group, a phenyl group, a naphthyl group, an anthryl group, a dimethyl-fluorenyl group, and a phenyl-carbazolyl group; —N($Q_1$)($Q_2$), —Si($Q_3$)($Q_4$)($Q_5$), —C(=O)($Q_6$) (where $Q_1$ to $Q_6$ may be each independently one of a hydrogen atom, a $C_1$-$C_{20}$ alkyl group, a phenyl group, a naphthyl group, and an anthryl group), and a binding site with an adjacent ligand via a single bond or a divalent linking group, but are not limited thereto.

In some embodiments, in Formula 1, $X_1$ may be $C(R_5)$; $R_1$ to $R_5$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, sulfonic acid group or a salt thereof, a phosphoric acid group or a salt thereof; a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and pentoxy group; a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group that are substituted with at least one of a deuterium atom, —F, hydroxyl group, a cyano group, a nitro group, and an amino group; a phenyl group, a naphthyl group, an anthryl group, a fluorenyl group, a phenanthrenyl group, a chrysenyl group, a carbazolyl group, a pyridinyl group, a pyrimidinyl group, a pyrazinyl group, a triazinyl group, a quinolinyl group, and an isoquinolinyl group; phenyl group, a naphthyl group, an anthryl group, a fluorenyl group, a phenanthrenyl group, a chrysenyl group, a carbazolyl group, a pyridinyl group, a pyrimidinyl group, a pyrazinyl group, a triazinyl group, a quinolinyl group, and an isoquinolinyl group that are substituted with at least one of a deuterium atom, —F, hydroxyl group, a cyano group, a nitro group, an amino group, a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, a pentoxy group, a phenyl group, a naphthyl group, and an anthryl group, but are not limited thereto.

In some embodiments, in Formula 1, $X_1$ may be N; $R_1$ to $R_4$ may be each independently, a hydrogen atom, a deuterium atom, a halogen atom, a hydroxyl group, cyano group, a nitro group, an amino group, an amidino group, a hydrazine, a hydrazone, carboxyl group or a salt thereof, sulfonic acid group or a salt thereof, a phosphoric acid group or a salt thereof; methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group that are substituted with at least one of a deuterium atom, —F, hydroxyl group, a cyano group, a nitro group, and an amino group; a phenyl group, a naphthyl group, an anthryl group, a fluorenyl group, a phenanthrenyl group, a chrysenyl group, a carbazolyl group, a pyridinyl group, a pyrimidinyl group, a pyrazinyl group, a triazinyl group, a quinolinyl group, and an isoquinolinyl group; and a phenyl group, a naphthyl group, an anthryl group, a fluorenyl group, a phenanthrenyl group, a chrysenyl group, a carbazolyl group, a pyridinyl group, a pyrimidinyl group, a pyrazinyl group, a triazinyl group, a quinolinyl group, and an isoquinolinyl group that are substituted with at least one of a deuterium atom, —F, a hydroxyl group, a cyano group, a nitro group, an amino group, a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, a pentoxy group, a phenyl group, a naphthyl group, and an anthryl group, but are not limited thereto.

For example, in Formula 1, $X_1$ may be $C(R_5)$; and $R_1$ to $R_5$ may be each independently, one of a hydrogen atom, a methyl group, an ethyl group, a n-propyl group, an i-propyl group, a n-butyl group, an i-butyl group, a t-butyl group, a methoxy group, an ethoxy group, a propoxy group, a butoxy group, a pentoxy group, a —$CF_3$, a phenyl group, a naphthyl group, an anthryl group, a pyridinyl group, a pyrimidinyl group and a triazinyl group. In some other embodiments, in Formula 1, $X_1$ may be N; and $R_1$ to $R_4$ may be each independently a hydrogen atom, a methyl group, an ethyl group, a n-propyl group, an i-propyl group, a n-butyl group, an i-butyl group, a t-butyl group, a methoxy group, an ethoxy group, a propoxy group, a butoxy group, a pentoxy group, a —$CF_3$, a phenyl group, a naphthyl group, an anthryl group, a pyridinyl group, a pyrimidinyl group, or a triazinyl group.

In Formula 1, at least two substitutents of $R_1$ to $R_5$ may be optionally linked to each other to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group.

In some embodiments,
the organometallic compound may be represented by Formula 1A below where $R_1$ and $R_2$ are linked to each other.
In some embodiments, the organometallic compound may be represented by Formula 1B below where $R_2$ and $R_3$ are linked to each other.
In some embodiments, the organometallic compound may be represented by Formula 1C below where $R_1$ to $R_3$ are linked to each other.
In some embodiments, the organometallic compound may be represented by Formula 1D below where $X_1$ is $C(R_5)$, and $R_4$ and $R_5$ are linked to each other.
In some embodiments, the organometallic compound may be represented by Formula 1E below where $R_1$ and $R_2$ are linked to each other, $X_1$ is $C(R_5)$, and $R_4$ and $R_5$ are linked to each other.
In some embodiments, the organometallic compound may be represented by Formula 1F below where $R_2$ and $R_3$ are linked to each other, $X_1$ is $C(R_5)$; and $R_4$ and $R_5$ are linked to each other, or
In some embodiments, the organometallic compound may be represented by Formula 1G below where $R_1$ to $R_3$ are linked to each other, $X_1$ is $C(R_5)$, and $R_4$ and $R_5$ are linked to each other.

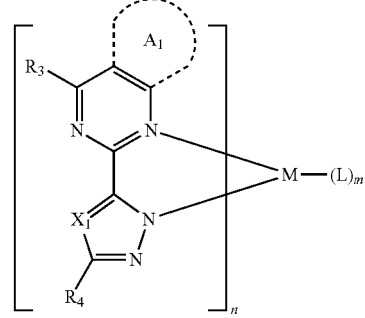

<Formula 1A>

-continued

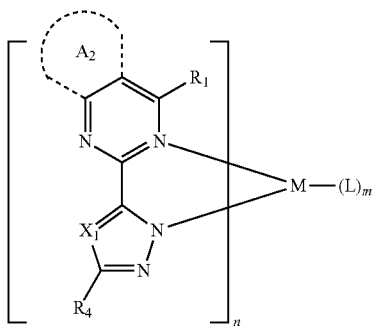
<Formula 1B>

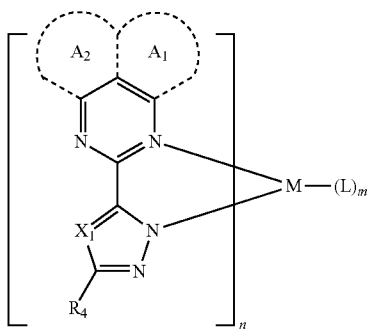
<Formula 1C>

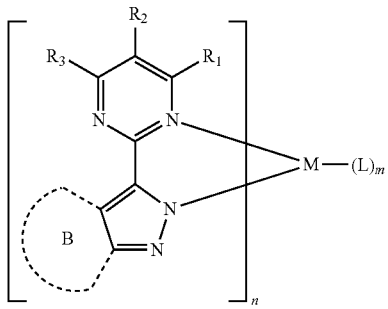
<Formula 1D>

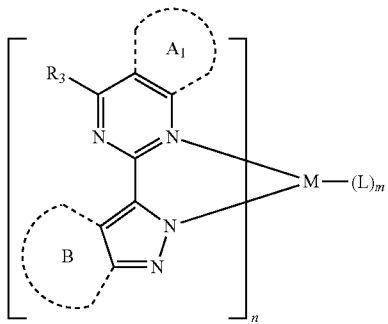
<Formula 1E>

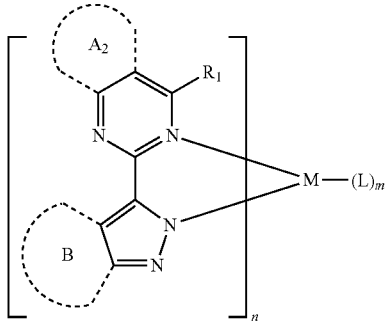
<Formula 1F>

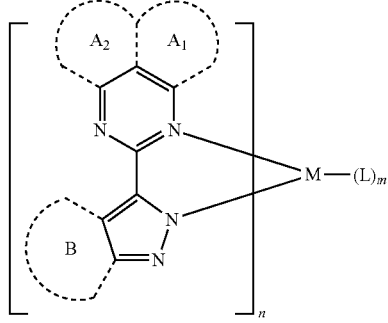
<Formula 1G>

In Formulae 1A to 1G, M, $R_1$, $R_2$, n, L and m may be as defined as above herein.

In Formulae 1A to 1G, an $A_1$ ring, an $A_2$ ring, and a B ring may be each independently a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group.

For example, in Formulae 1A to 1G, the $A_1$ ring and the $A_2$ ring may be each independently one of benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene; and benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one hydrogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (where $Q_{11}$ to $Q_{15}$ are each independently one of a hydrogen atom, a $C_1$-$C_{10}$ alkyl group, a $C_6$-$C_{20}$ aryl group, and a $C_2$-$C_{20}$ heteroaryl group);

In Formulae 1A to 1G, the B ring may be one of cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene; and cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one hydrogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —$N(Q_{11})(Q_{12})$, and —$Si(Q_{13})(Q_{14})(Q_{15})$ (where $Q_{11}$ to $Q_{15}$ are each independently one of a hydrogen atom, a $C_1$-$C_{10}$ alkyl group, a $C_6$-$C_{20}$ aryl group, and a $C_2$-$C_{20}$ heteroaryl group), but is not limited thereto.

In some embodiments, the organometallic compound may be represented by Formula 1A-(1), 1A-(2), 1B-(1), 1D-(1), 1D-(2), 1D-(3), 1F-(1), 1F-(2) or 1F-(3) below, but is not limited thereto:

<Formula 1A-(1)>

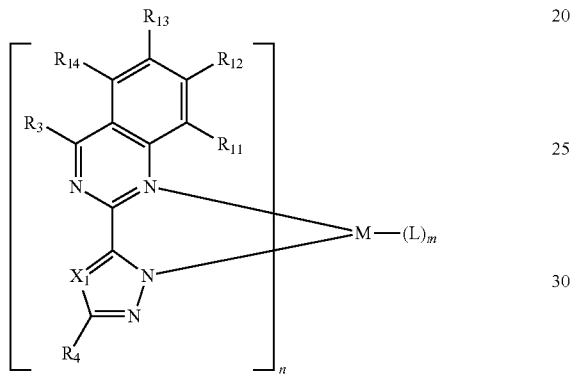

<Formula 1A-(2)>

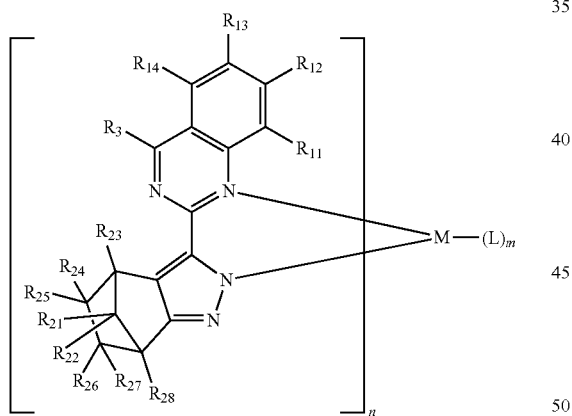

<Formula 1B-(1)>

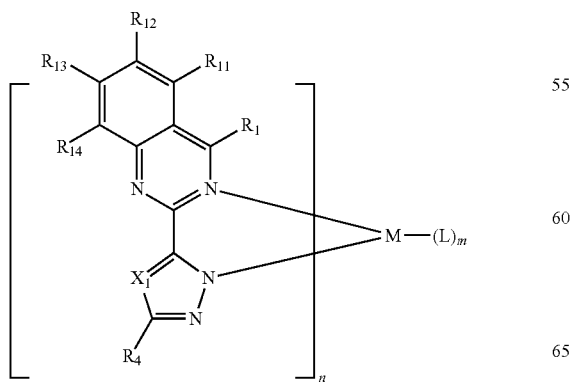

<Formula 1D-(1)>

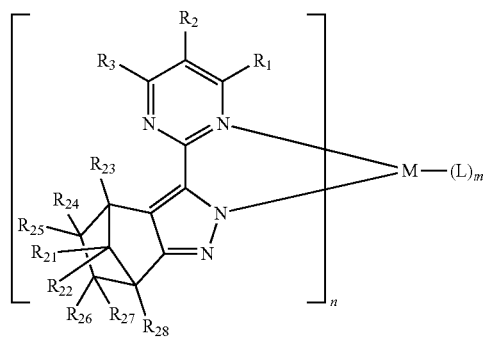

<Formula 1D-(2)>

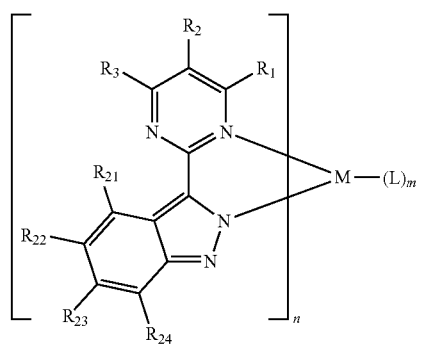

<Formula 1D-(3)>

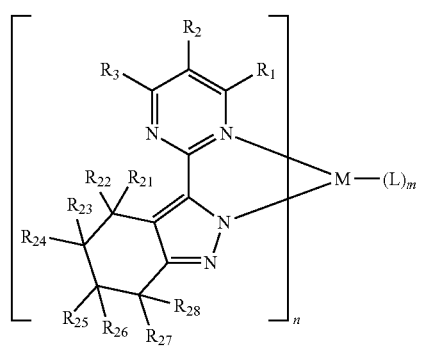

<Formula 1F-(1)>

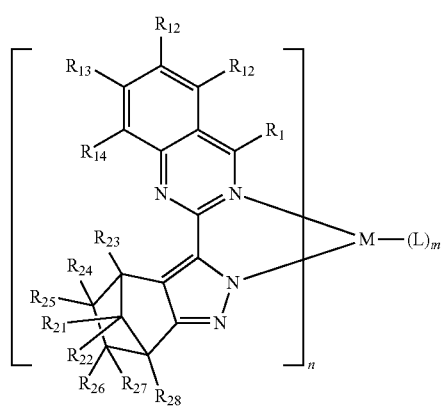

<Formula 1F-(2)>

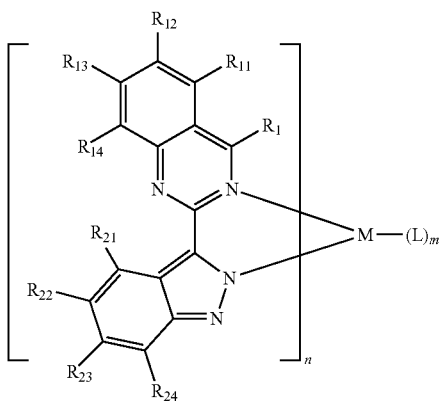

<Formula 1F-(3)>

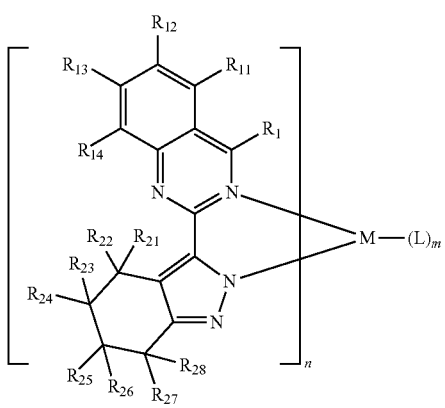

In Formula 1A-(1), 1A-(2), 1B-(1), 1D-(1), 1D-(2), 1D-(3), 1F-(1), 1F-(2), and 1F-(3), M and $R_1$ to $R_3$ are as defined above, n, L and m are as defined below, $R_{11}$ to $R_{14}$ and $R_{21}$ to $R_{28}$ are each independently as defined above described in conduction with $R_1$.

For example, in Formulae 1A-(1), 1A-(2), 1B-(1), 1D-(1), 1D-(2), 1D-(3), 1F-(1), 1F-(2) and 1F-(3), M may be a transition metal (for example, osmium (Os), iridium (Ir), or platinum (Pt)); $R_1$ to $R_3$, $R_{11}$ to $R_{14}$ and $R_{21}$ to $R_{28}$ may be each independently one of a hydrogen atom, a deuterium atom, a halogen atom, a hydroxyl group, a cyano group, a nitro group, an amino group, an amidino group, a hydrazine, a hydrazone, carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; n may be an integer from 1 to 3; L may be an organic ligand; and m may be an integer from 0 to 4, but are not limited thereto.

In Formula 1, n may be an integer from 1 to 3. That is, Formula 1 may include one, two, or three ligands represented by Formula 1' below:

<Formula 1'>

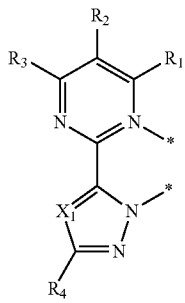

In Formula 1', * indicates a binding site with M in Formula 1.

The organometallic compound must include the ligand represented by Formula 1'.

When n is 2 or greater, at least two ligands of Formula 1' may be identical to or different from each other.

In Formula 1, L is an organic ligand, m indicates the number of L's, and m may be an integer from 0 to 4. L may be a monodentate organic ligand, a bidentate organic ligand, a tridentate organic ligand, or a tetradentate organic ligand. When m is 0, the organometallic compound may include only the ligand of Formula 1'. When m is 2 or greater, the at least two L's may be identical to or different from each other.

L represents an organic ligand. For example, in Formula 1, L may include at least one of Formulae 2A to 2F and may include a cyano group, but is not limited thereto:

Formula 2A

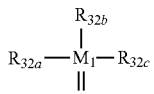

Formula 2B

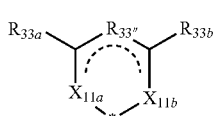

Formula 2C

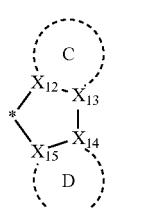

Formula 2D

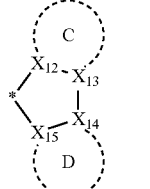

Formula 2E

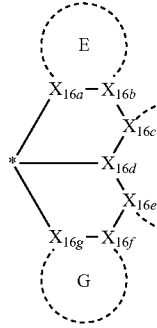

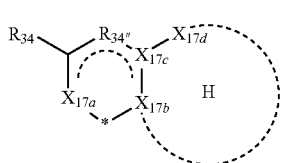

Formula 2F

In Formulae 2A to 2F, $M_1$ may be P or As.

In Formulae 2A to 2F, $X_{11a}$, $X_{11b}$, $X_{12}$, $X_{13}$, $X_{14}$, $X_{15}$, $X_{16a}$, $X_{16b}$, $X_{16c}$, $X_{16d}$, $X_{16e}$, $X_{16f}$, $X_{16g}$, $X_{17a}$, $X_{17b}$, $X_{17c}$ and $X_{17d}$ may be each independently one of C, N, O, N($R_{35}$), P($R_{36}$)($R_{37}$) and As($R_{38}$)($R_{39}$); $R_{33"}$ and $R_{34"}$ may be each independently one of a single bond, a substituted or unsubstituted $C_1$-$C_5$ alkylene group (for example, methylene, ethylene, or the like) and a substituted or unsubstituted $C_2$-$C_5$ alkenylene group (for example, an ethylene group or the like); and $R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, and a substituted or unsubstituted $C_2$-$C_{60}$ heteroaryl group; a C ring, a D ring, an E ring, a F ring, a G ring, and a H ring may be each independently a 5-membered to 20-membered saturated ring or a 5-membered to 20-membered unsaturated ring; and * indicates a binding site with M in Formula 1.

In Formulae 2A to 2F, $R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$ and $R_{39}$ may be each independently one of a hydrogen atom, a deuterium atom, a halogen atom, a hydroxyl group, a cyano group, a nitro group, an amino group, an amidino group, a hydrazine, a hydrazone, carboxyl group or a salt thereof, sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group and amino; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

For example, in Formula 1, when m is 1 or greater, L may include a ligand of Formula 2C above, $X_{11a}$ and $X_{11b}$ in Formula 2C may be one of O and P($R_{36}$)($R_{37}$), and $R_{36}$ and $R_{37}$ may be each independently one of a $C_1$-$C_{10}$ alkyl group, a phenyl group, a naphthyl group and an anthryl group.

In some other embodiments, in Formula 1, when m is 1 or greater, L may include a ligand of Formula 2B above, $M_1$ in Formula 2B being P and $R_{32a}$, $R_{32b}$, and $R_{32c}$ being each independently one of a $C_1$-$C_{10}$ alkyl group, a phenyl group, a naphthyl group, and an anthryl group, but are not limited thereto.

In some embodiments, in Formula 1, when m is 1 or greater, L may include at least one of the ligands of Formula 2D, 2E, and 2F; and the C ring, D ring, E ring, F ring, G ring, and H ring in Formulae 2D, 2E and 2F above may be each independently one of a substituted or unsubstituted benzene, a substituted or unsubstituted pentalene, a substituted or unsubstituted indene, a substituted or unsubstituted naphthalene, a substituted or unsubstituted azulene, a substituted or unsubstituted heptalene, a substituted or unsubstituted indacene, a substituted or unsubstituted acenaphthylene, a substituted or unsubstituted fluorene, a substituted or unsubstituted spiro-fluorene, a substituted or unsubstituted phenalene, a substituted or unsubstituted phenanthrene, a substituted or unsubstituted anthracene, a substituted or unsubstituted fluoranthene, a substituted or unsubstituted triphenylene, a substituted or unsubstituted pyrene, a substituted or unsubstituted chrysene, a substituted or unsubstituted pyrrole, a substituted or unsubstituted imidazole, a substituted or unsubstituted pyrazole, a substituted or unsubstituted isothiazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted isoindole, a substituted or unsubstituted indole, a substituted or unsubstituted indazole, a substituted or unsubstituted purine, a substituted or unsubstituted isoquinoline, a substituted or unsubstituted quinoline, a substituted or unsubstituted phthalazine, a substituted or unsubstituted quinoxaline, a substituted or unsubstituted quinazoline, or a substituted or unsubstituted cinnoline. In this regard, i) when the C ring has at least two substituents, adjacent two of the at least two substitutents may be optionally linked to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

When one of the D ring in Formula 2D, the E ring in Formula 2E, the F ring in Formula 2E, the G ring in Formula 2E and the H ring in Formula 2F has at least two adjacent substituents, the at least two adjacent substitutents may be optionally linked to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

In this regard, the terms "one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group" are as defined above and described in connection with the C ring, the D ring, the E ring, the F ring, the G ring and the H ring.

In Formula 1, n may be 2 and m may be 0; n may be 1 and m may be 1; n may be 2 and m may be 2; or n may be 3 and m may be 0, but the inventive combinations of m and n are not limited thereto.

In some embodiments, the organometallic compound may be an organometallic compound with n=2 and m=0 in Formula 1 above, two ligands of Formula 1' being identical to each other, and the organometallic compound may be in a trans-form.

In some other embodiments, n may be 2, and the organometallic compound may be represented by Formula 3 or Formula 4:

<Formula 3>

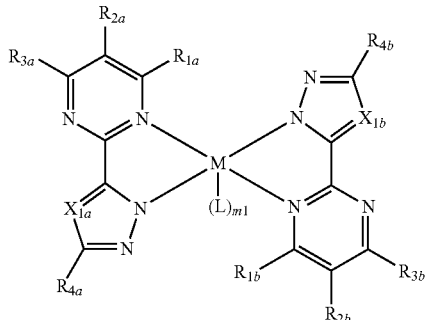

<Formula 4>

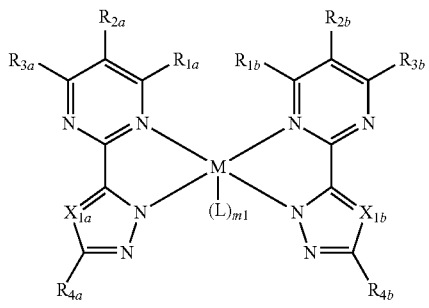

In Formulae 3 and 4, M and L are as defined above, and m1 may be 0, 1, or 2.

In Formulae 3 and 4, $X_{1a}$ may be one of N and $C(R_{5a})$, $X_{1b}$ may be one of N and $C(R_{5b})$, and $R_{1a}$ to $R_{5a}$, and $R_{1b}$ to $R_{5b}$ may be as defined above in conjunction with $R_1$.

In some other embodiments, the organometallic compound may be a compound represented by one of Formulae 3A to 3J below:

<Formula 3A>

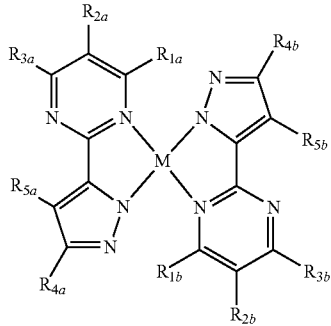

<Formula 3B>

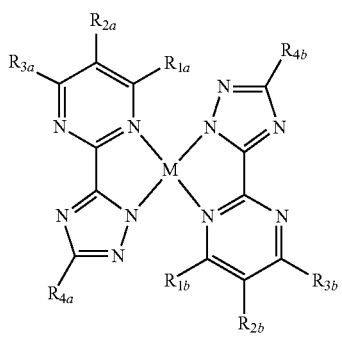

<Formula 3C>

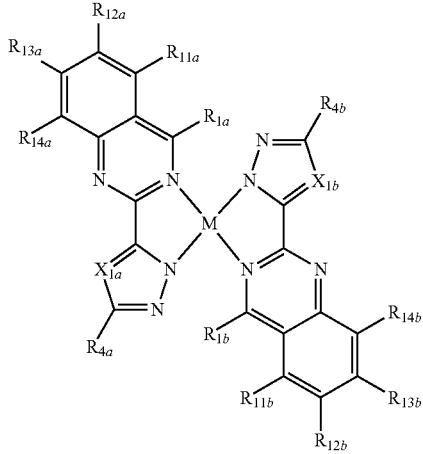

<Formula 3D>

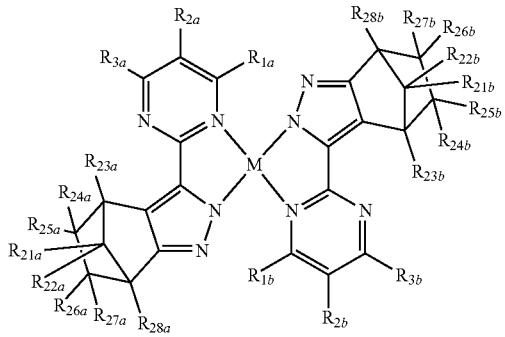

<Formula 3E>

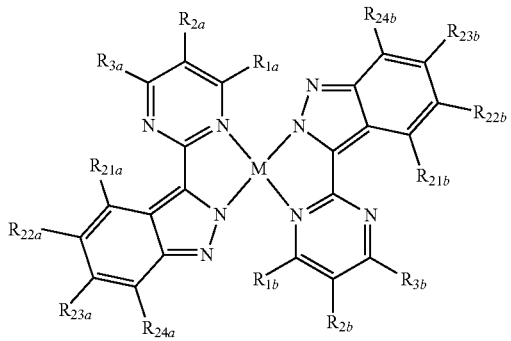

<Formula 3F>

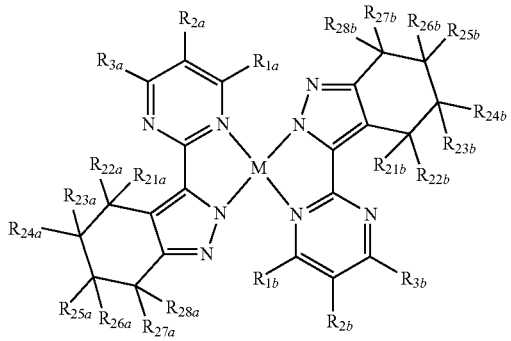

-continued

<Formula 3G>

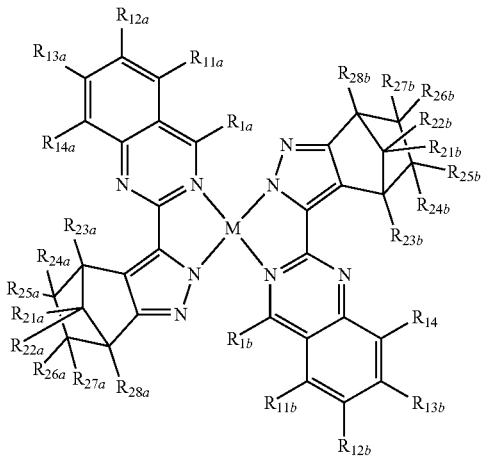

<Formula 3H>

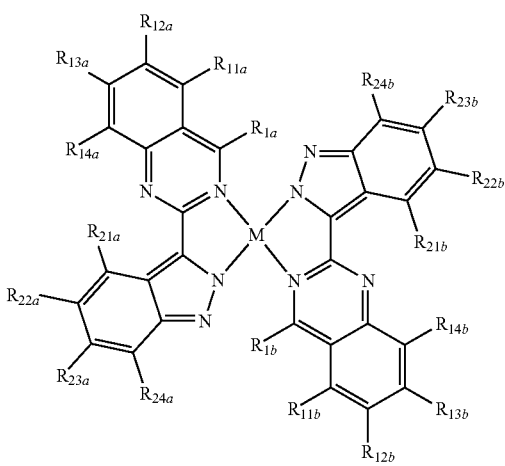

<Formula 3I>

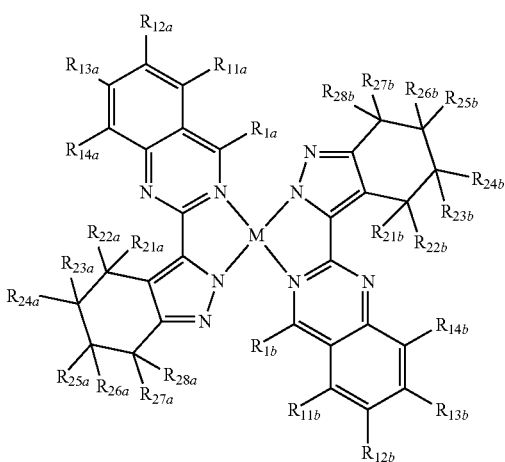

-continued

<Formula 3J>

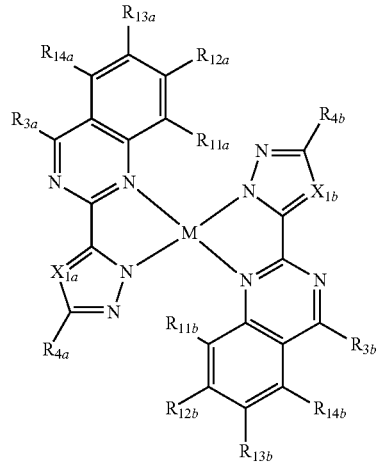

In Formulae 3A to 3J, M may be Pt; $X_{1a}$ may be one of N and $C(R_{5a})$; $X_{1b}$ may be one of N and $C(R_{5b})$; $R_{1a}$ to $R_{5a}$, $R_{1b}$ to $R_{5b}$, $R_{11a}$ to $R_{14a}$, $R_{11b}$ to $R_{14b}$, $R_{21a}$ to $R_{28a}$, and $R_{21b}$ to $R_{28b}$ may be each independently as defined above in conjunction with $R_1$.

For example, in Formulae 3A to 3I, M may be Pt; $X_{1a}$ may be one of N and $C(R_{5a})$; $X_{1b}$ may be one of N and $C(R_{5b})$; $R_{1a}$ to $R_{5a}$, $R_{1b}$ to $R_{5b}$, $R_{11a}$ to $R_{14a}$, $R_{11b}$ to $R_{14b}$, $R_{21a}$ to $R_{28a}$, and $R_{21b}$ to $R_{28b}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, and a triazinyl group, but are not limited thereto.

In some embodiments, the organometallic compound may be a compound represented by one of Formulae 3I to 3J, two ligands being identical to each other, and the organometallic compounds may be in a trans-form.

In some other embodiments, the organometallic compound may be a compound represented by Formula 3A or 3B, wherein $R_{1a}$=$R_{1b}$, $R_{2a}$=$R_{2b}$, $R_{3a}$=$R_{3b}$, $R_{4a}$=$R_{4b}$, and $R_{5a}$=$R_{5b}$. In this regard, M may be Pt, and the organometallic compound may be in a trans-form. In some other embodiments, the organometallic compound may be a compound represented by Formula 3A or 3B, $R_{1a}$=$R_{1b}$, $R_{2a}$=$R_{2b}$, $R_{3a}$=$R_{3b}$, $R_{4a}$=$R_{4b}$, $R_{5a}$=$R_{5b}$, M is Pt, and $R_{1a}$ to $R_{5a}$ being each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group (for example, a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, or the like), a $C_1$-$C_{20}$ alkyl group substituted with at least one of —F (for example, —$CF_3$), a $C_1$-$C_{20}$alkoxy group, a phenyl group, a naphthyl group, and an anthryl group, but is not limited thereto.

The organometallic compound may be a compound represented by Formula 4-(a) below:

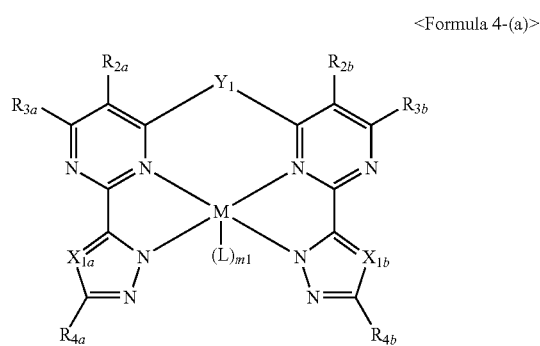

<Formula 4-(a)>

In Formula 4-(a), M and L may be as defined above, and m1 may be 0, 1, or 2.

In Formula 4-(a), $X_{1a}$ may be one of N and $C(R_{5a})$; $X_{1b}$ may be one of N and $C(R_{5b})$; $R_{2a}$ to $R_{5a}$ and $R_{2b}$ to $R_{5b}$ may be as defined above in conjunction with $R_1$.

In Formula 4-(a), $Y_1$ may be i) a divalent linking group including at least one of —O—, —S—, —N($Z_1$)—, —[C($Z_2$)($Z_3$)]$_a$—, and —[Si($Z_4$)($Z_5$)]$_b$—, or ii) a single bond.

In —N($Z_1$)—, —[C($Z_2$)($Z_3$)]$_a$—, and —[Si($Z_4$)($Z_5$)]$_b$—, $Z_1$ to $Z_5$ may be each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, or a $C_2$-$C_{60}$ heteroaryl group; and a and b may be each independently an integer from 1 to 4.

For example, in —N($Z_1$)—, —[C($Z_2$)($Z_3$)]$_a$—, and —[Si($Z_4$)($Z_5$)]$_b$—, $Z_1$ to $Z_5$ may be each independently one of a $C_1$-$C_{20}$ alkyl group (for example, a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, or the like), a $C_1$-$C_{20}$ alkyl group (for example, —$CF_3$) substituted with at least —F, a phenyl group, a naphthyl group, and an anthryl group; and a and b may be each independently 1 or 2, but are not limited thereto.

For example, in Formula 4-(a), $Y_1$ may be —N($Z_1$)—; and $Z_1$ may be one of a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group, but not limited thereto.

In some embodiments, the organometallic compound may be a compound represented by Formula 3 above, L including a ligand represented by Formula 2B above, and m1 may be 2, but is not limited thereto:

In Formula 2B, $M_1$ may be P, $R_{32a}$, $R_{32b}$, and $R_{32c}$ may be each independently a $C_1$-$C_{10}$ alkyl group, a phenyl group, a naphthyl group, or an anthryl group.

The organometallic compound may be a compound represented by Formula 1 above with n=3 and n=0. That is, the organometallic compound may include only three ligands of Formula 1' above. In some embodiments, in the organometallic compound of Formula 1 above with n=3 and m=0, M may be Ir, and $X_1$ and $R_1$ to $R_4$ may be as defined above. For example, the organometallic compound may be a compound represented by Formula 3K below, but is not limited thereto:

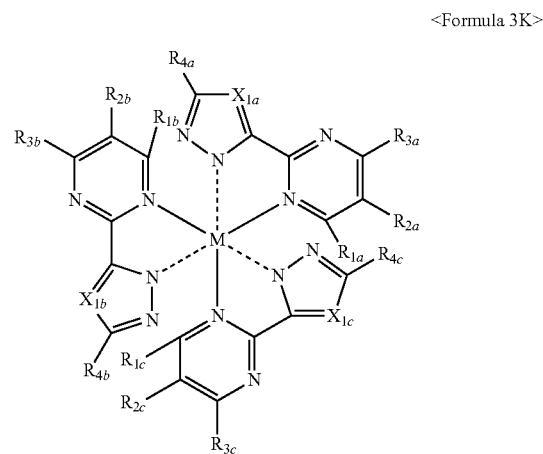

<Formula 3K>

In Formula 3J, $X_{1a}$ may be one of N and $C(R_{5a})$; $X_{1b}$ may be one of N and $C(R_{5b})$; $X_{1c}$ may be one of N and $C(R_{5c})$; and $R_{1a}$ to $R_{5a}$, $R_{1b}$ to $R_{5b}$, and $R_{1c}$ to $R_{5c}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, and a triazinyl group, but not limited thereto.

The organometallic compound may be a compound represented by Formula 1 where n is 1 and m is an integer from 1 to 4.

In some embodiments, the organometallic compound of Formula 1 where n is 1 and m is an integer from 1 to 4 may be a compound represented by one of Formulae 5 to 8 below, but is not limited thereto:

<Formula 5>

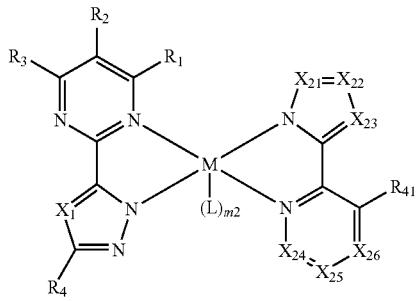

<Formula 6>

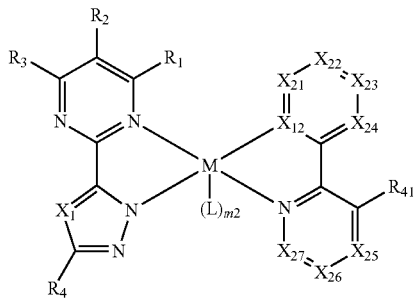

<Formula 7>

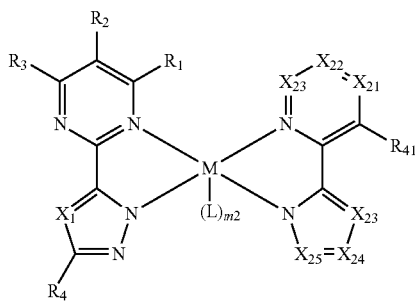

<Formula 8>

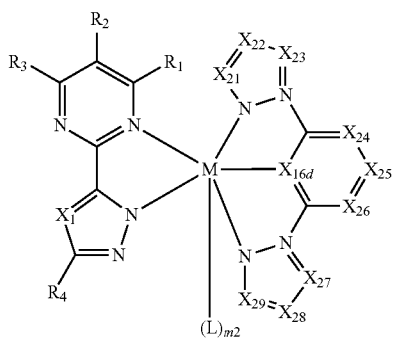

In Formulae 5 to 8, $X_1$ may be one of N and $C(R_5)$; M, $R_1$ to $R_5$, and L may be as defined above; and m2 may be one of 0, 1 and 2.

In Formulae 5 to 8, $X_{12}$ and $X_{16d}$ may be each independently one of N and C; $X_{21}$ may be one of N and $C(R_{51})$, $X_{22}$ may be one of N and $C(R_{52})$, $X_{23}$ may be one of N and $C(R_{53})$, $X_{24}$ may be one of N and $C(R_{54})$, $X_{25}$ may be one of N and $C(R_{55})$, $X_{26}$ may be one of N and $C(R_{56})$, $X_{27}$ may be one of N and $C(R_{57})$, $X_{28}$ may be one of N and $C(R_{58})$, $X_{29}$ may be one of N and $C(R_{59})$; $R_{41}$, $R_{42}$, and $R_{51}$ to $R_{59}$ may be each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-N(Q_{11})(Q_{12})$, $-Si(Q_{13})(Q_{14})(Q_{15})$ (where $Q_{11}$ to $Q_{15}$ may be each independently selected from a hydrogen atom, a $C_1$-$C_{10}$ alkyl group, a $C_6$-$C_{20}$ aryl group, and a $C_2$-$C_{20}$ heteroaryl group), and a binding site with an adjacent ligand via a single bond or a divalent linking group, two adjacent substituents of $R_{41}$, $R_{42}$, and $R_{51}$ to $R_{59}$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

In Formulae 5 to 8, $R_{41}$, $R_{42}$, and $R_{51}$ to $R_{59}$ may be as defined above in conjunction with $R_1$, and the terms "a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group" are as defined above in conjunction with the B ring.

In some embodiments, the organometallic compound may be a compound represented by Formula 5-(1), 5-(2), 6-(1), or 8-(1) below:

<Formula 5-(1)>

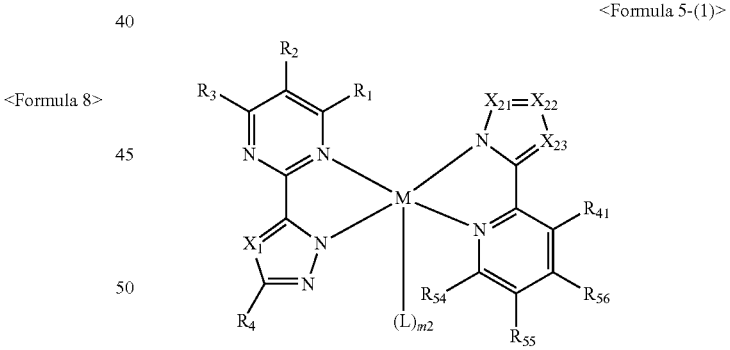

<Formula 5-(2)>

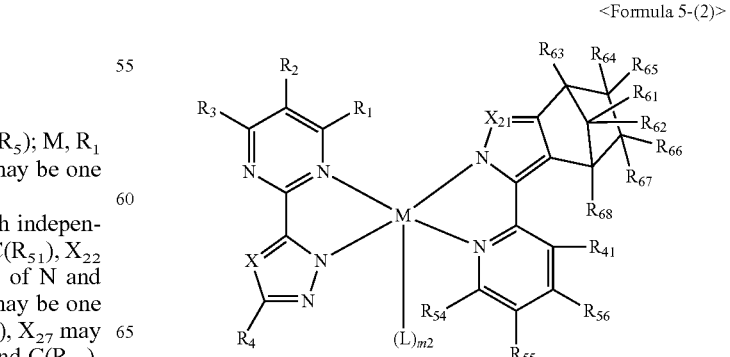

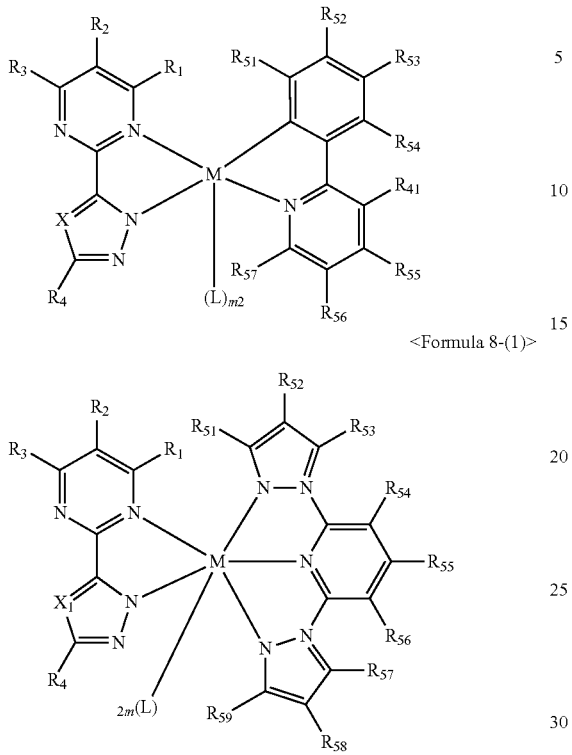

<Formula 6-(1)>

<Formula 8-(1)>

In Formula 5-(1), 5-(2), 6-(1), and 8-(1), $X_1$ may be one of N and $C(R_5)$; M, $R_1$ to $R_5$, L, m2, $X_{21}$ to $X_{23}$, $R_{41}$, and $R_{51}$ to $R_{59}$ may be as defined above; and $R_{61}$ to $R_{68}$, may be as defined above in conjunction with $R_{11}$.

For example, in Formula 5-(1), 5-(2), 6-(1), and 8-(1), $X_{21}$ may be one of N and $C(R_{51})$, $X_{22}$ may be one of N and $C(R_{52})$, $X_{23}$ may be one of N and $C(R_{53})$; and $R_{41}$, $R_{51}$ to $R_{59}$, and $R_{61}$ to $R_{68}$ may be each independently one of a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxy group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxy group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group, not limited thereto.

The organometallic compound may be one of Compounds 1 to 45 below, but is not limited thereto:

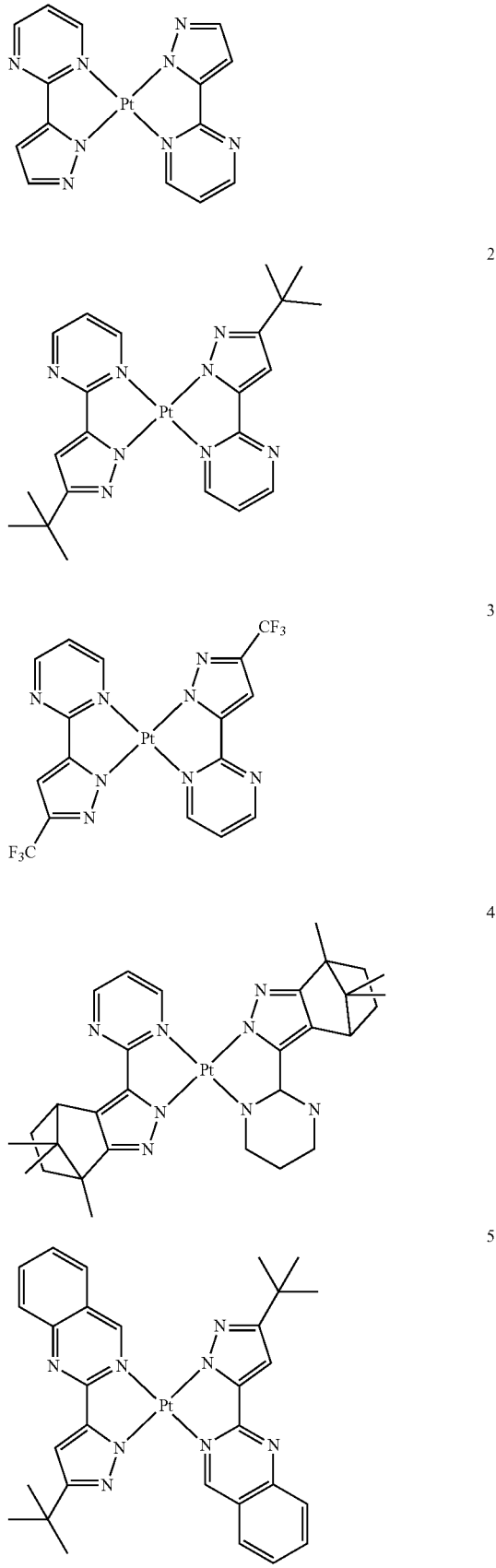

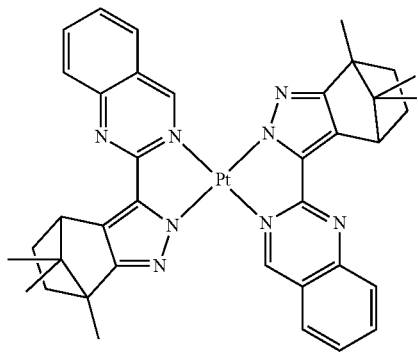
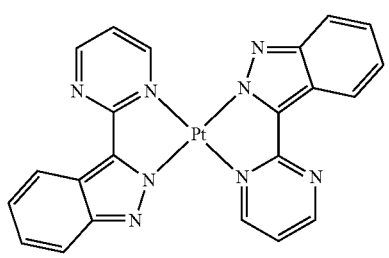
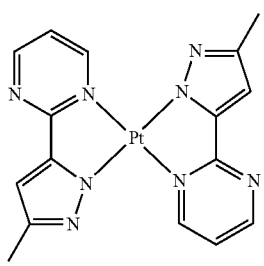
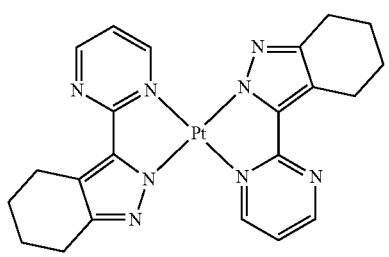
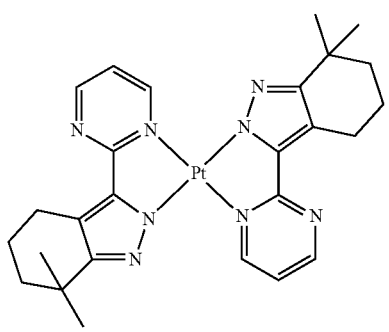
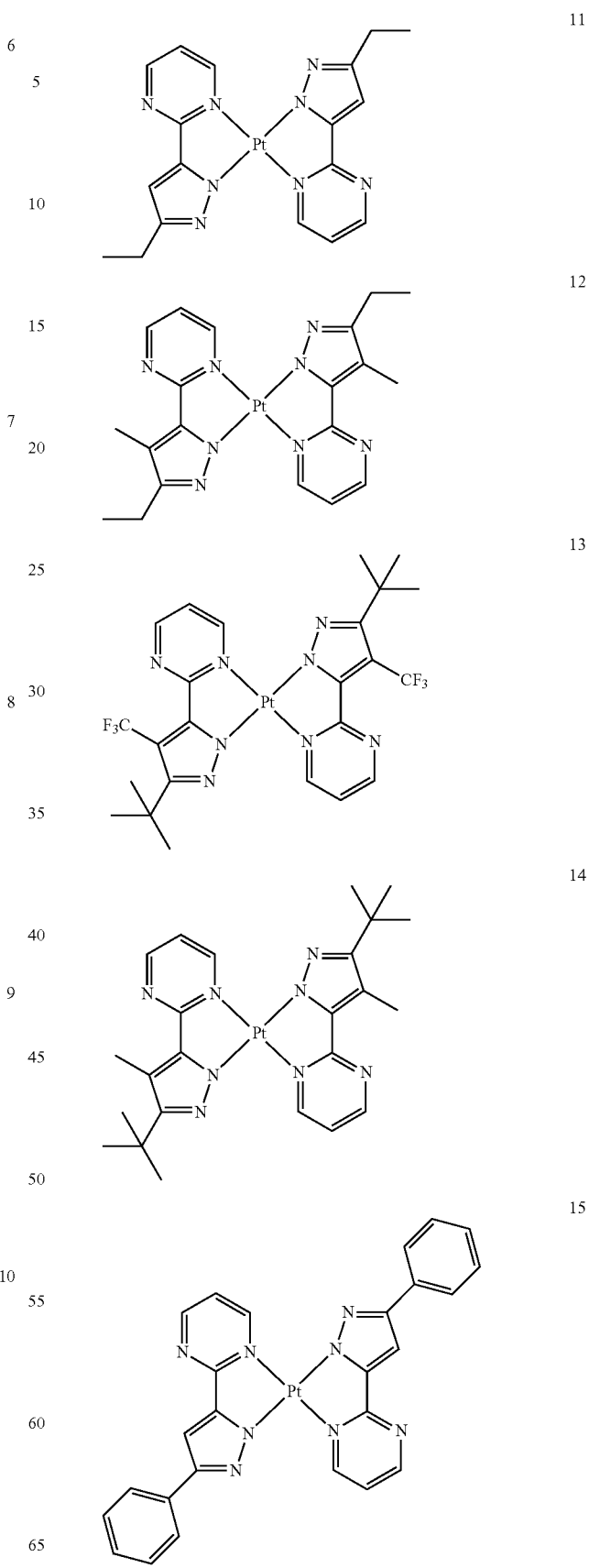

16
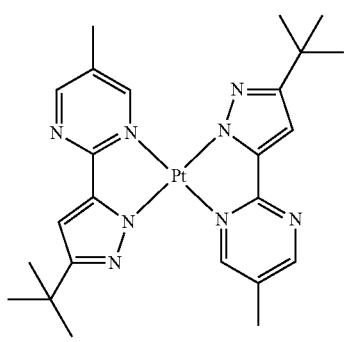
17
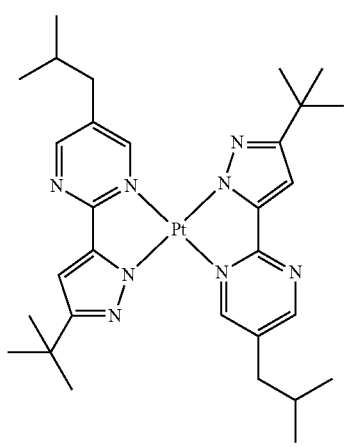
18
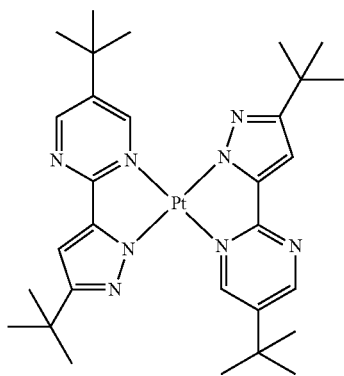
19
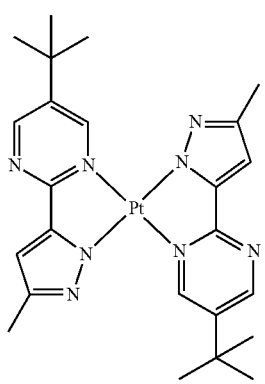
20
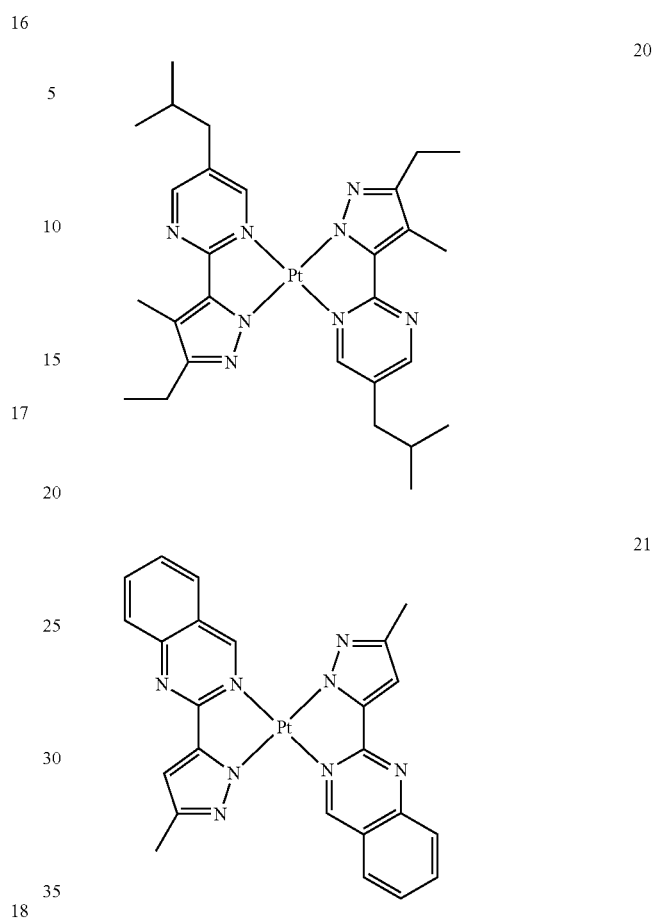
21
22
23
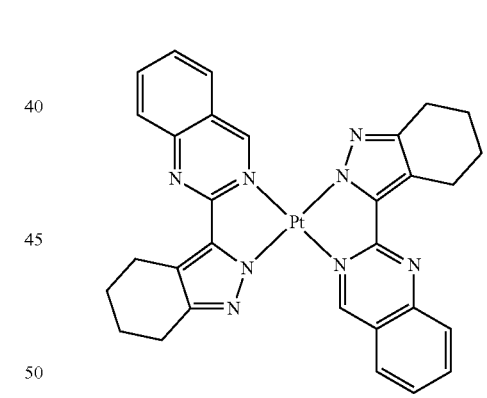
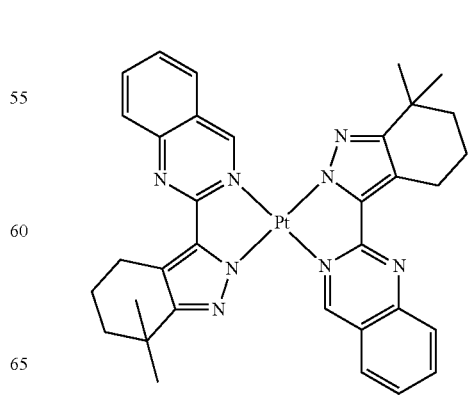

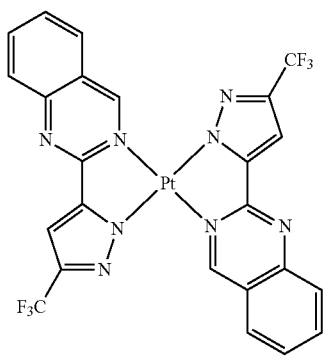
24
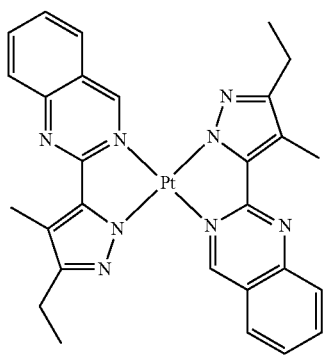
25
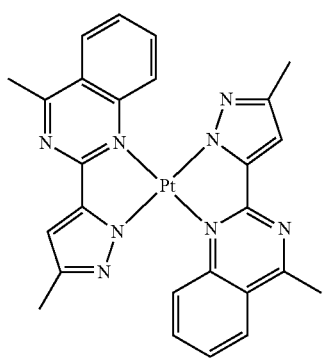
26
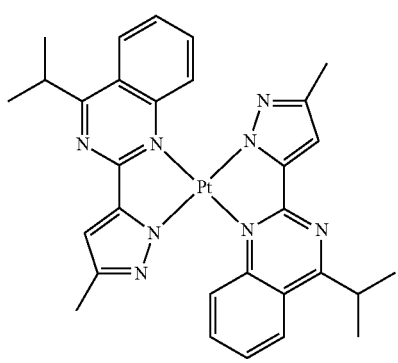
27
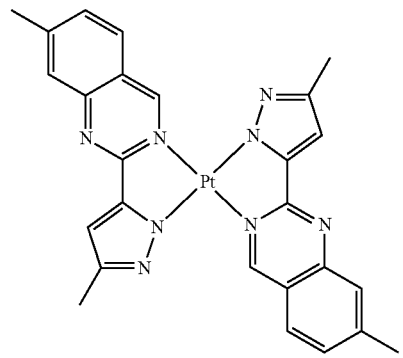
28
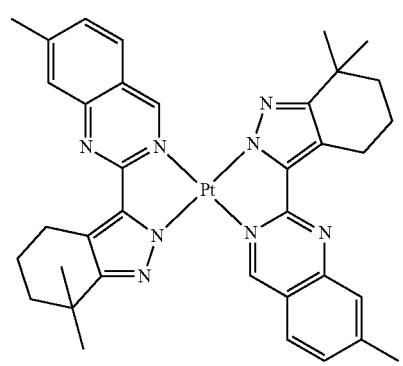
29
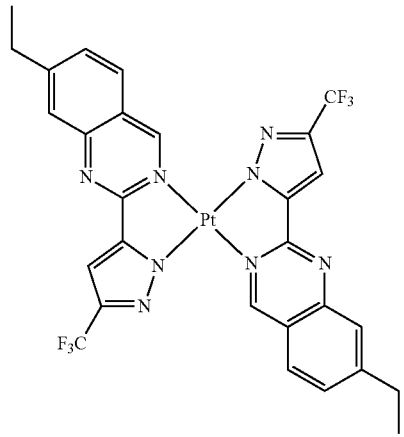
30
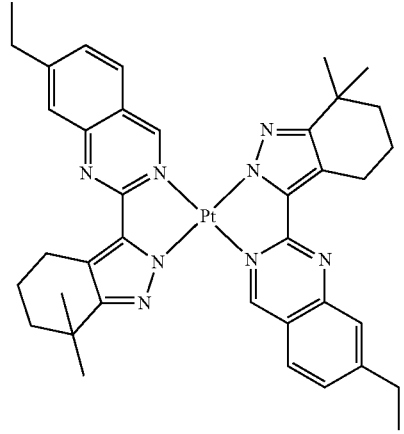
31

31
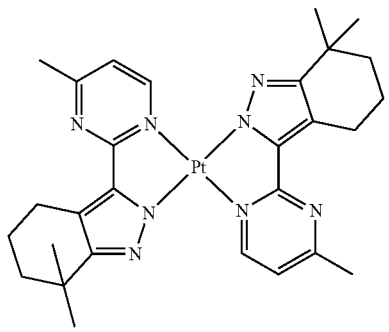
32
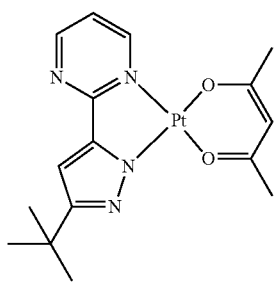
33
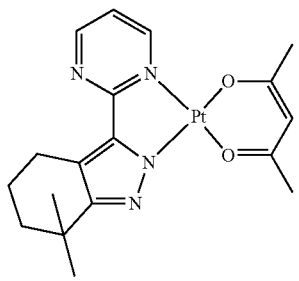
34
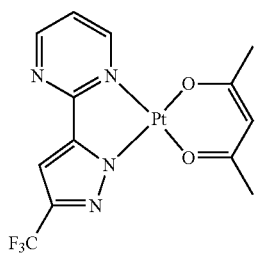
35
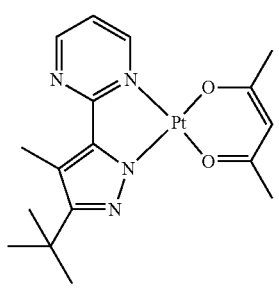
36
32
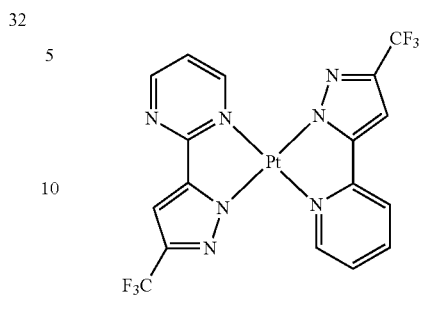
37
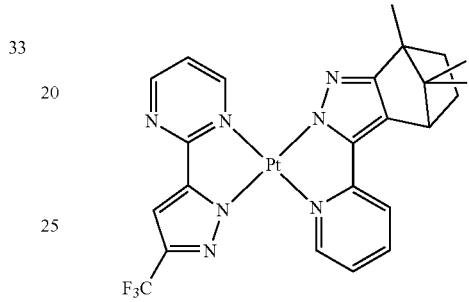
38
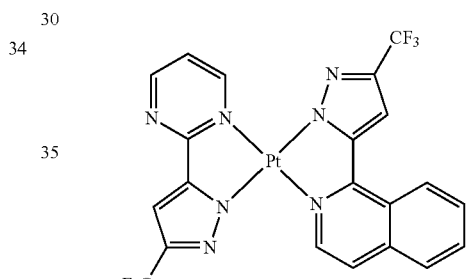
39
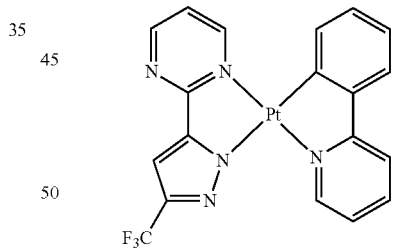
40
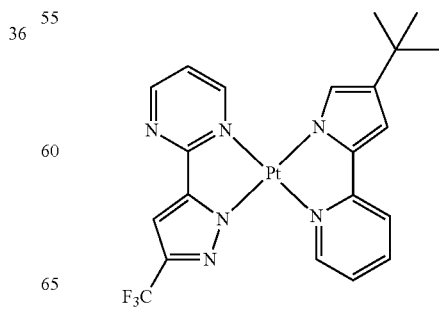
41

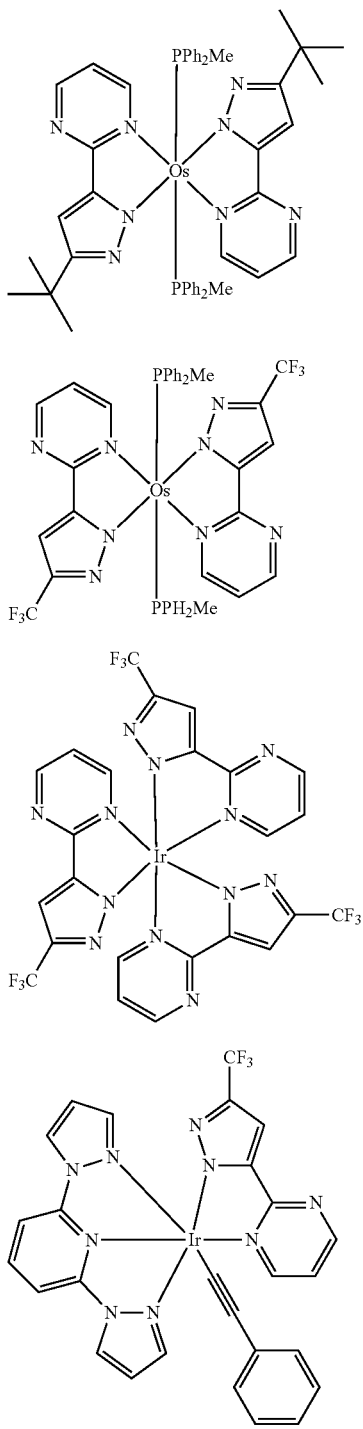

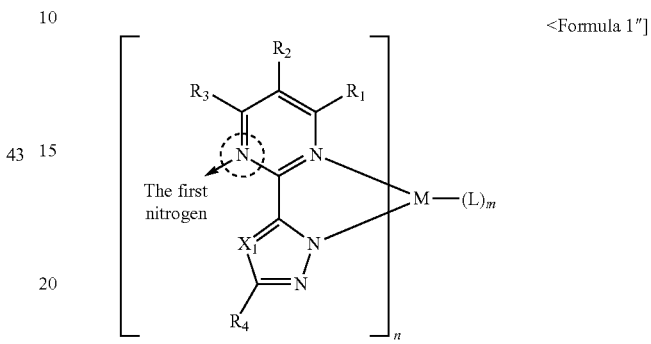

Since the organometallic compound of Formula 1 above includes a first nitrogen below (see Formula 1" below), it may have a relatively low highest occupied molecular orbital (HOMO) energy level. Thus, when the organometallic compound of Formula 1 is used as a dopant in an emission layer of an organic light-emitting device, a high charge-transfer effect between the host and the dopant may be attained. Accordingly, the organic light-emitting device including the organometallic compound of Formula 1 may have high efficiency characteristics. Due to the inclusion of the first nitrogen (see Formula 1" below,) the organometallic compound may have high electron drawing characteristics as compared with an imaginary compound without the first nitrogen. Therefore, the organometallic compound may have a strong binding strength between a 5-membered ring and a core metal M in a ligand and thus may have an improved thermal stability.

<Formula 1"]

Therefore, since the organometallic compound of Formula 1 above has high thermal stability, an organic light-emitting device including the organometallic compound may have a low driving voltage, a high luminance, a high efficiency, and a long lifetime.

The organometallic compound of Formula 1 may be synthesized using an organic synthesis method. A synthesis method of the organometallic compound of Formula 1 may be understood by those of ordinary skill in the art from the examples that will be described below.

The organometallic compound of Formula 1 may be used between a pair of electrodes of an organic light-emitting device, for example, an emission layer of an organic light-emitting device.

According to another embodiment of the present invention, an organic light-emitting device includes a first electrode, a second electrode disposed opposite to the first electrode, and an organic layer disposed between the first electrode and the second electrode, the organic layer including the organometallic compound of Formula 1 described above.

As used herein, "(for example, the organic layer) including at least one organometallic compound" means that "(the organic layer) including one of the organometallic compounds of Formula 1 above, or at least two different organometallic compounds of Formula 1 above".

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The term "organic layer" as used herein refers to a single layer and/or a plurality of layers disposed between the first and second electrodes of the organic light-emitting device.

The organic layer may include an emission layer, and the emission layer may include the organometallic compound of Formula 1 described above. The emission layer including the organometallic compound may emit light based on the mechanism of phosphorescence.

In some embodiments, the organometallic compound in the emission layer of the organic light-emitting device may serve as a dopant, and the emission layer may further include a carbazole-based compound as a host.

For example, the carbazole-based compound as the host may be represented by Formula 10 below, but is not limited thereto:

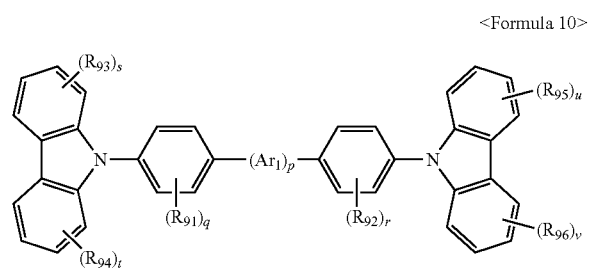

<Formula 10>

In Formula 10, $Ar_1$ may be selected from a substituted or unsubstituted $C_1$-$C_{60}$ alkylene group, a substituted or unsubstituted $C_2$-$C_{60}$ alkenylene group, —C(=O)—, —N($R_{100}$)— (where $R_{100}$ may be a substituted or unsubstituted $C_6$-$C_{60}$ aryl group, or a substituted or unsubstituted $C_2$-$C_{60}$ heteroaryl group), a substituted or unsubstituted $C_6$-$C_{60}$ arylene group and a substituted or unsubstituted $C_2$-$C_{60}$ hetero arylene group; p may be an integer from 0 to 10; $R_{91}$ to $R_{96}$ may be each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_2$-$C_{60}$ heteroaryl group, two adjacent substituents of $R_{91}$ to $R_{96}$ being optionally linked to each other to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group; and q, r, s, t, u, and v may be each independently an integer from 1 to 4.

In Formula 10 above, $Ar_1$ may be one of a $C_1$-$C_5$ alkylene group, a $C_2$-$C_5$ alkenylene group, —C(=O)—, and —N($R_{100}$)-yl, where $R_{100}$ may be one of a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In Formula 10, $R_{91}$ to $R_{96}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group.

The carbazole-based compound may be one of the following compounds, but is not limited thereto:

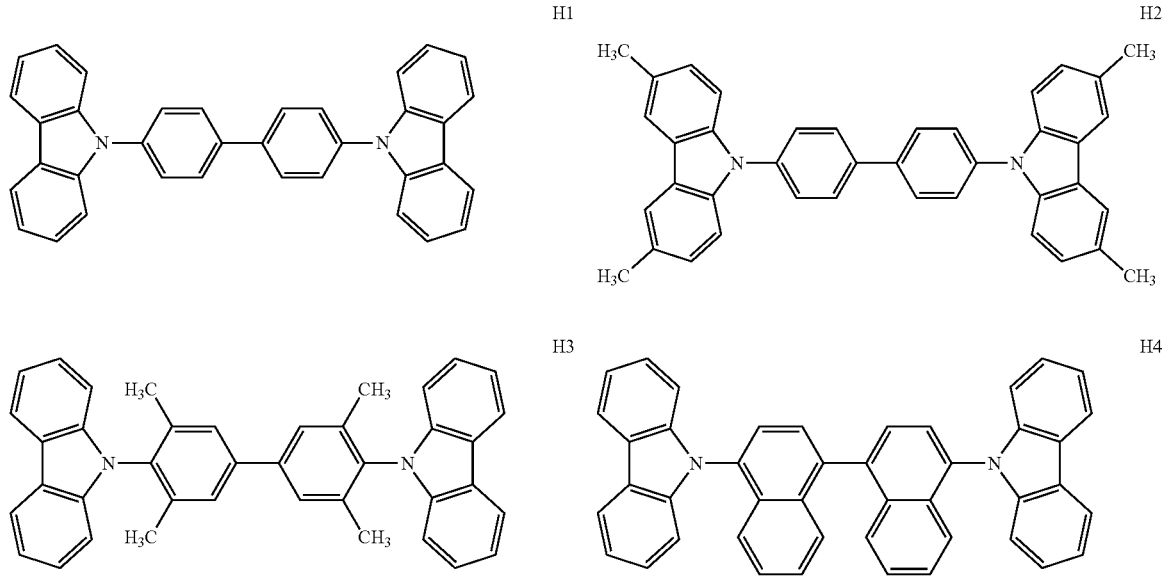

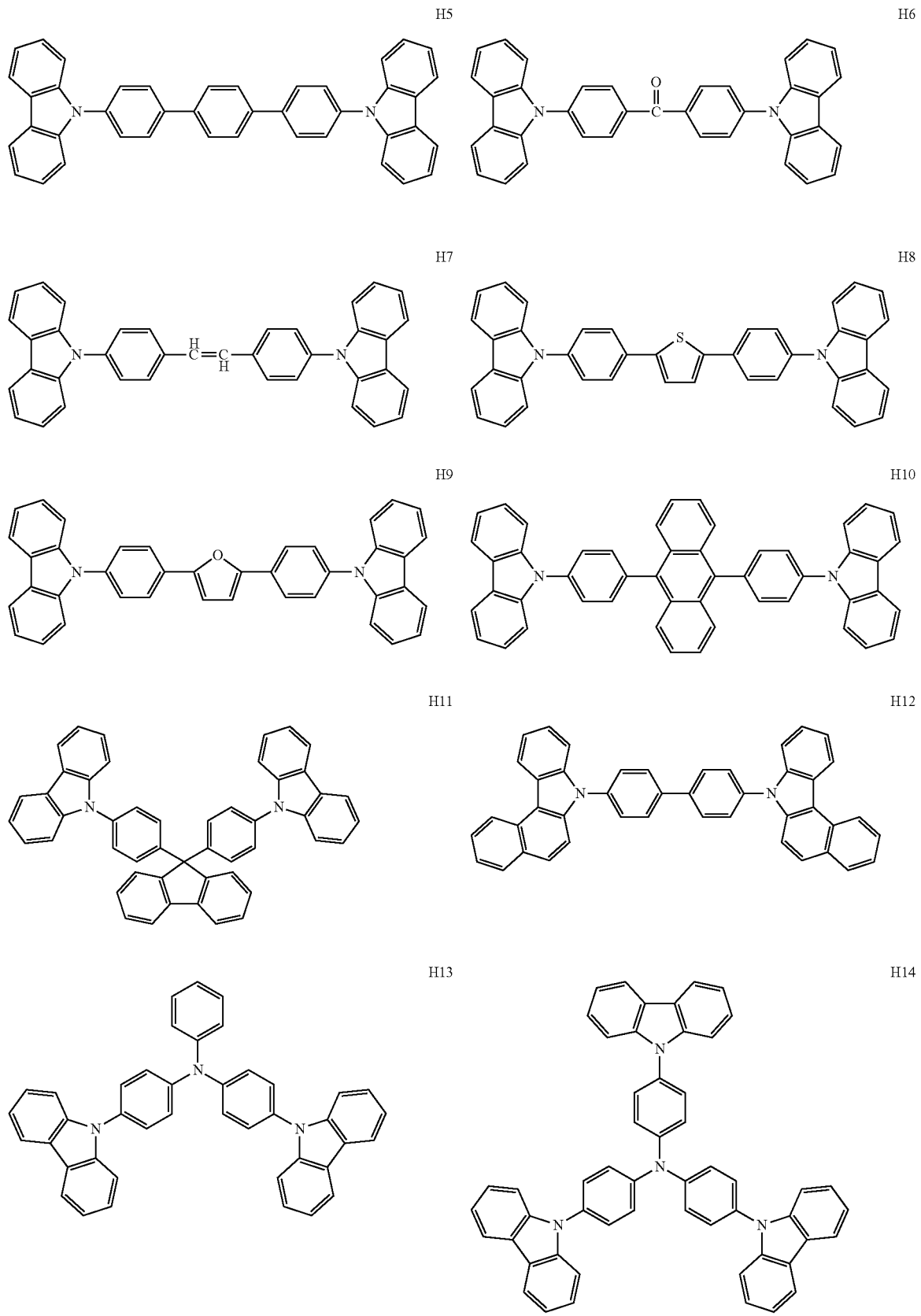

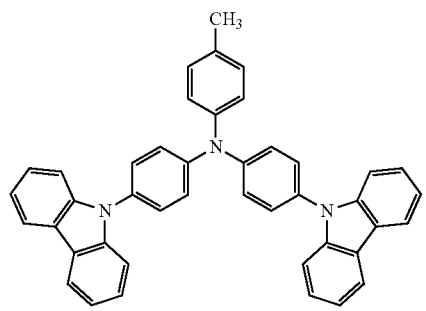
H15
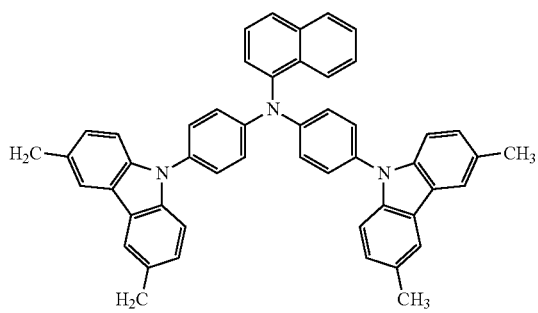
H16
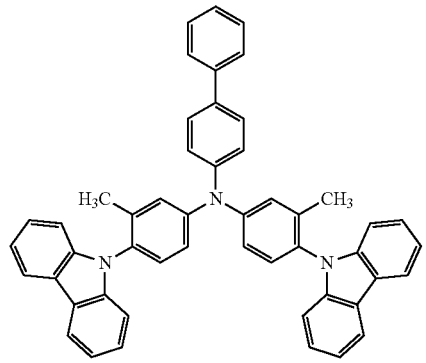
H17
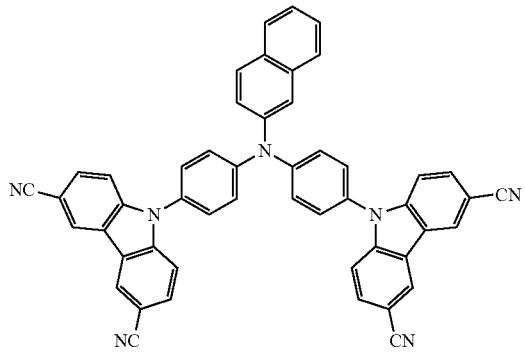
H18
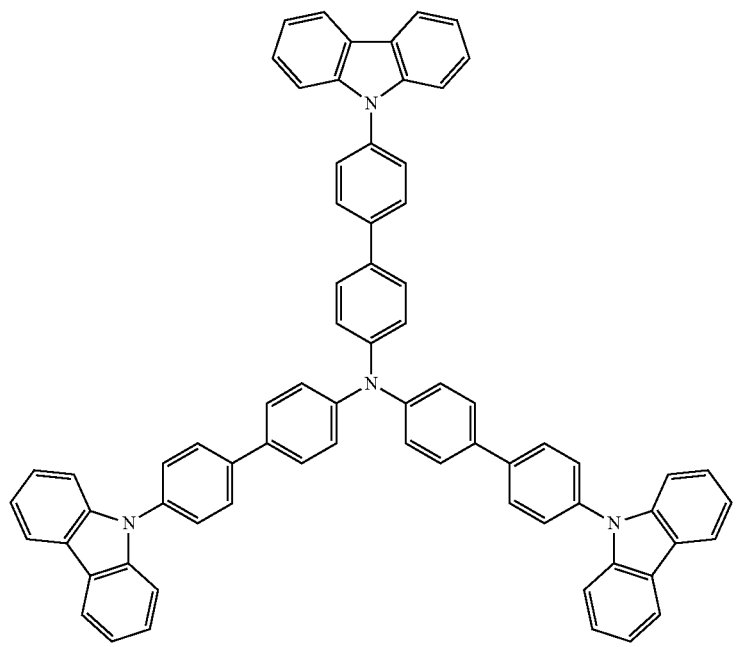
H19

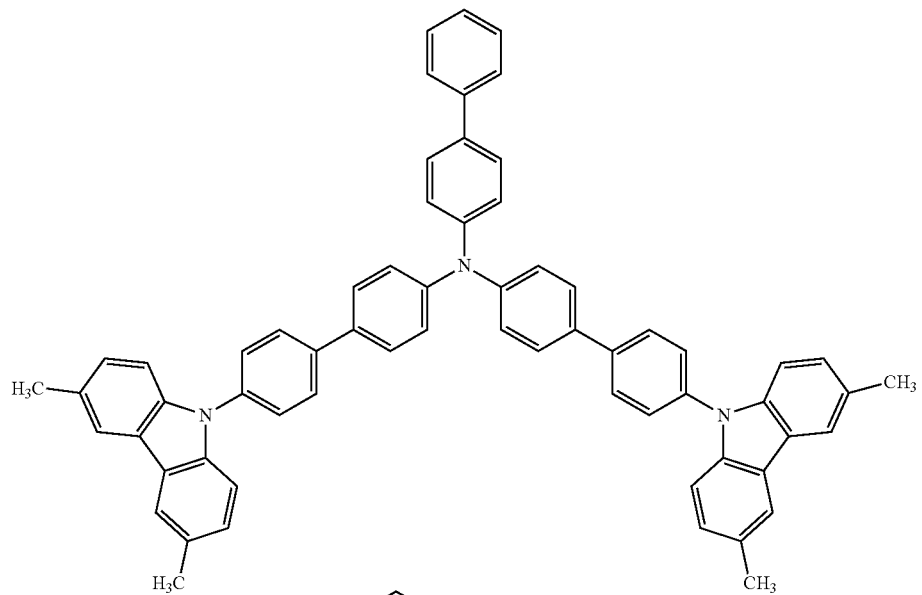
H20
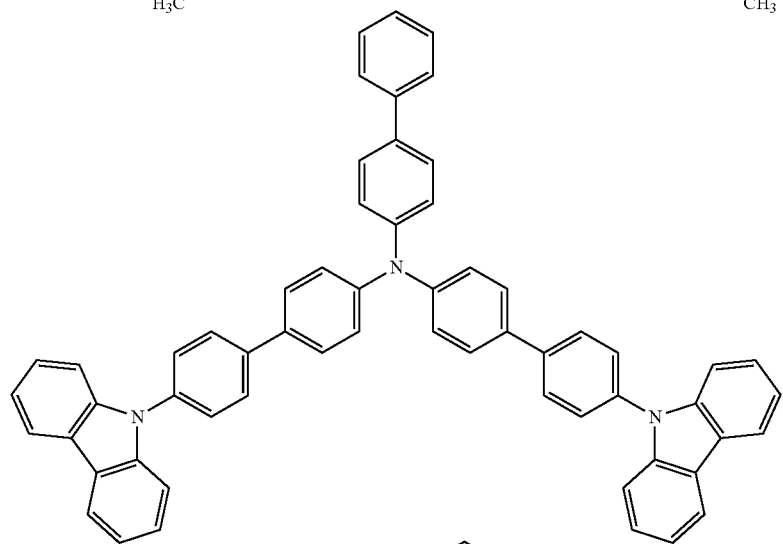
H21
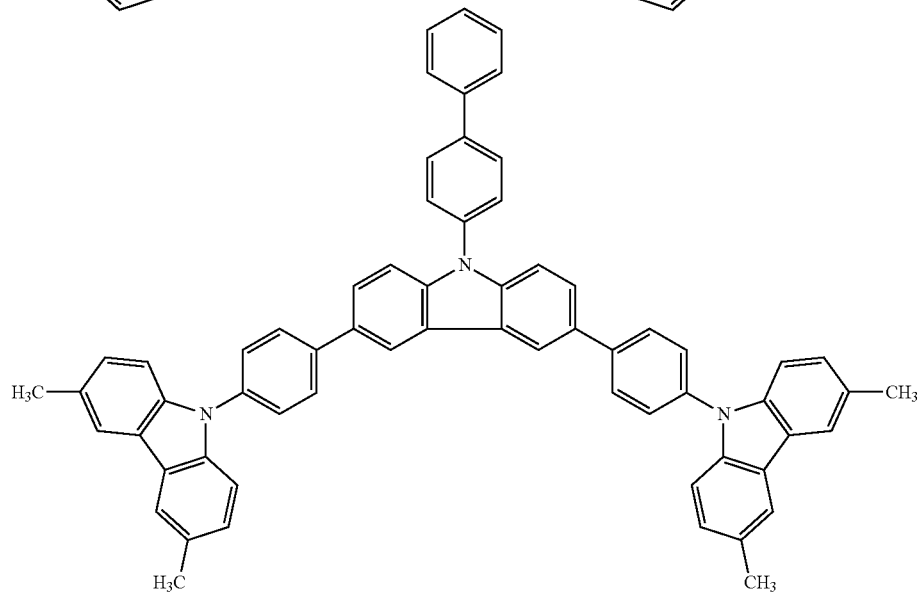
H22

H23
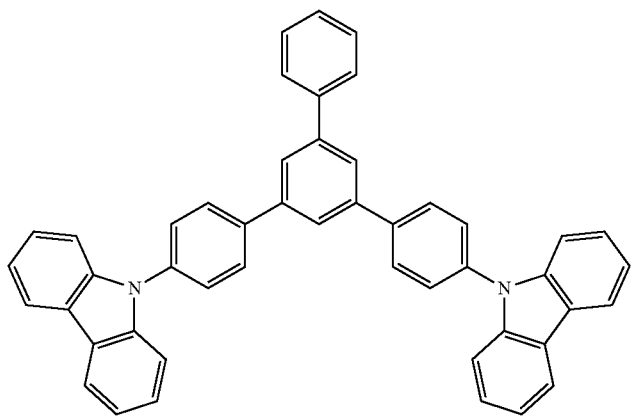
H24
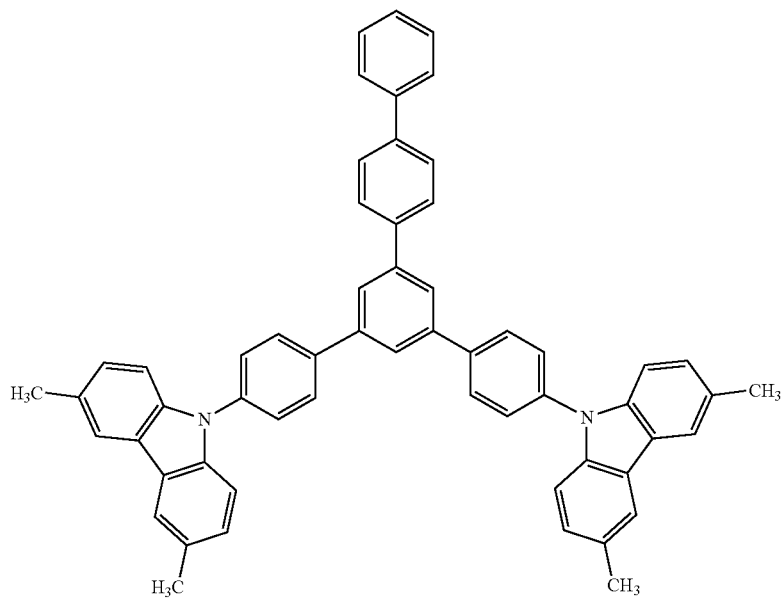
H25
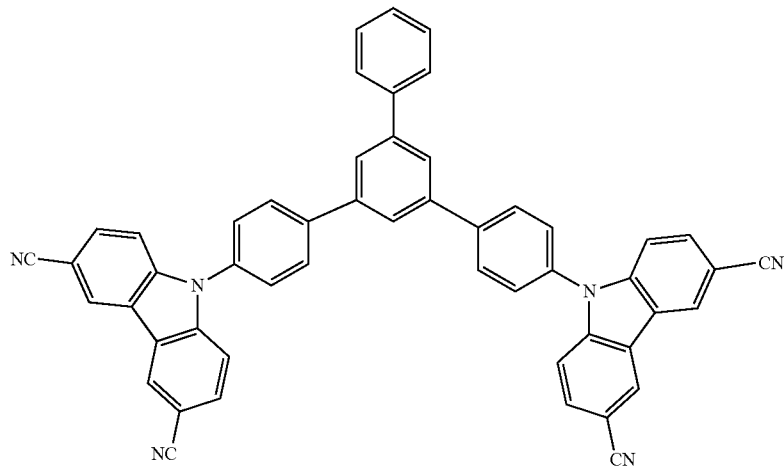

-continued
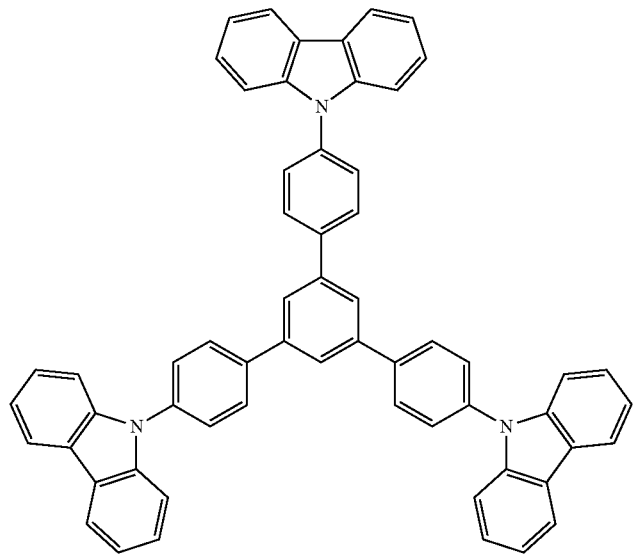
H26
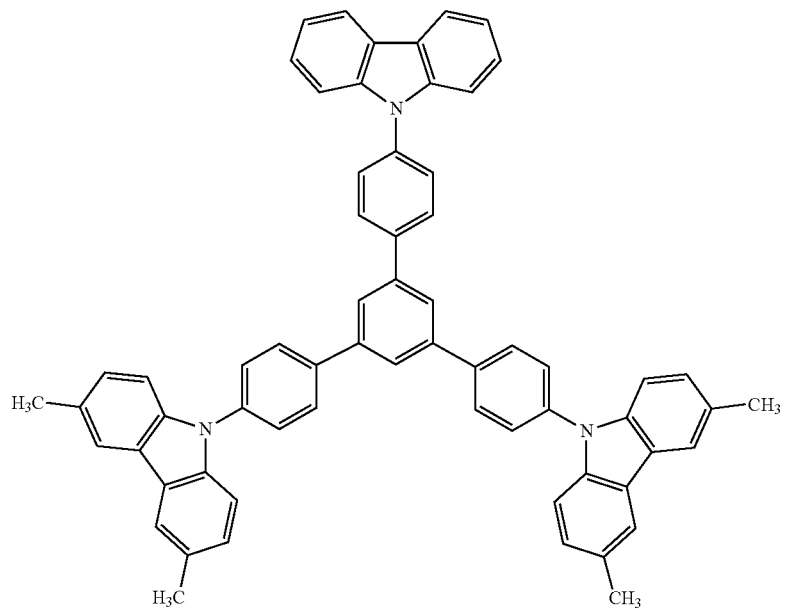
H27

-continued
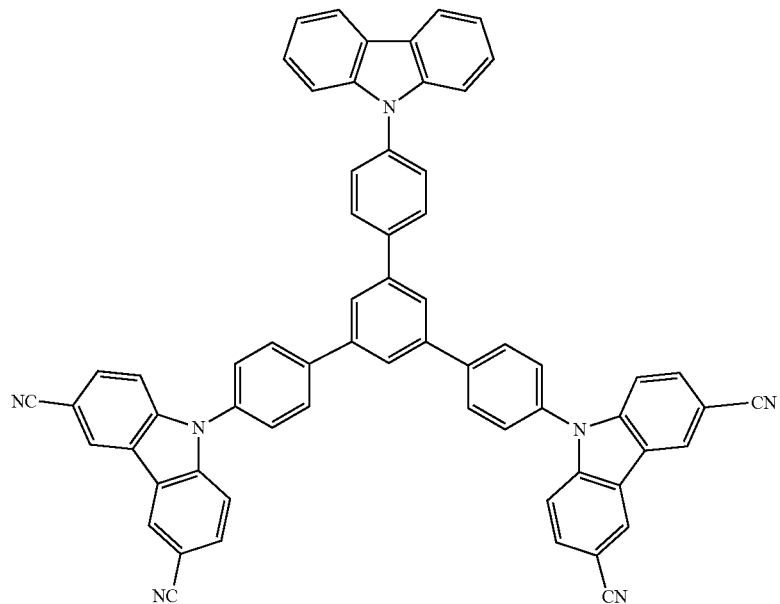
H28
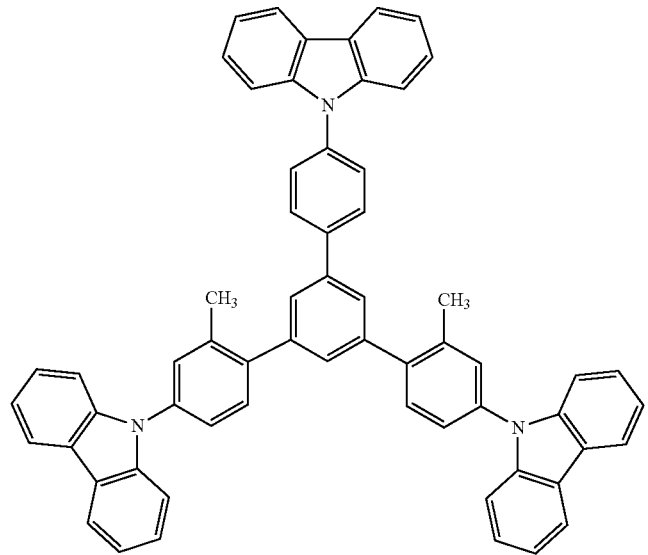
H29

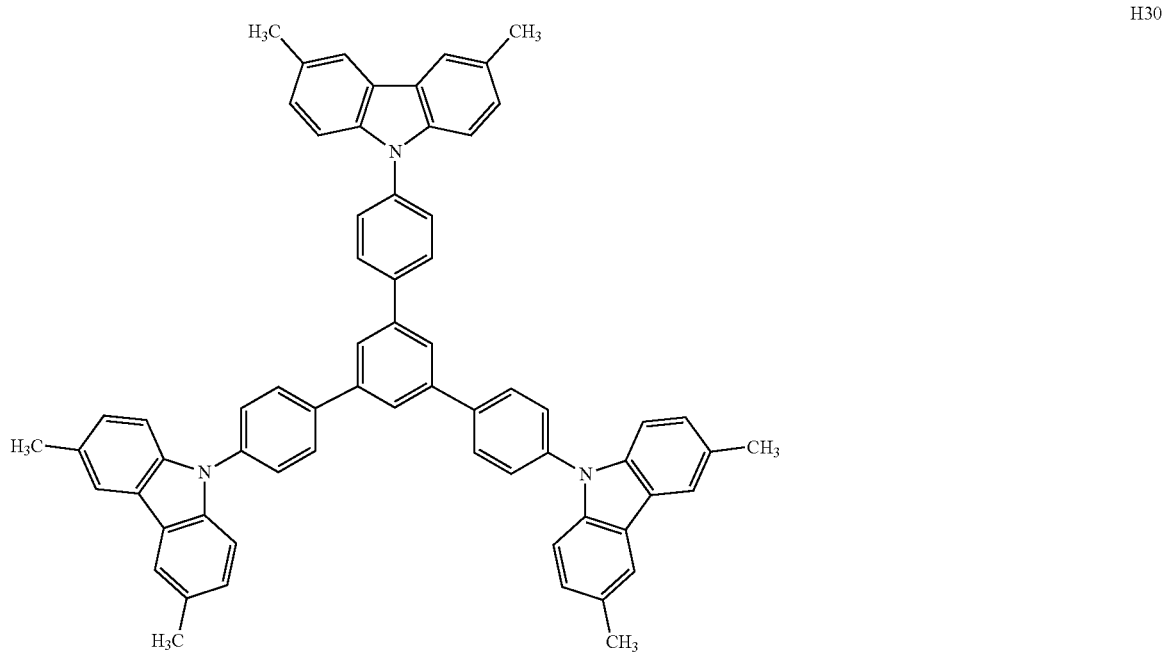

H30

FIG. 1 is a schematic cross-sectional view of an organic light-emitting device 10 according to an embodiment of the present invention. Hereinafter, a structure of an organic light-emitting device according to an embodiment of the present invention and a method of manufacturing the same will now be described with reference to FIG. 1.

The substrate 11 may be any substrate that is used in existing organic light-emitting devices. In some embodiments, the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate. When the first electrode 13 is an anode, a material having a high work function may be used as the first electrode-forming material to facilitate hole injection. The first electrode 13 may be a reflective electrode or a transmissive electrode. Suitable first electrode-forming materials include transparent and conductive materials such as indium tin oxide (ITO), indium zinc oxide (IZO), $SnO_2$, and ZnO. In some embodiments, the first electrode 13 may be formed as a reflective electrode using one of magnesium (Mg), aluminum (Al), aluminum-lithium (Al—Li), calcium (Ca), magnesium-indium (Mg—In), magnesium-silver (Mg—Ag), and the like.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of from about $10^{-8}$ torr to about $10^{-3}$ torr, and a deposition rate of from about 0.01 to about 100 Å/sec. However, the deposition conditions are not limited thereto.

When the HIL is formed using spin coating, the coating conditions may vary according to the compound that is used to form the HIL and the desired structure and thermal properties of the HIL to be formed. For example, the coating rate may be in the range of from about 2000 rpm to about 5000 rpm, and a temperature at which heat treatment is performed to remove a solvent after coating may be in the range of from about 80° C. to about 200° C. However, the coating conditions are not limited thereto.

Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4"-tris-(3-methylphenylphenylamino)triphenylamine (m-MTDATA), N,N'-di(1-naphthyl)-N,N'-diphenylbenzidine (NPB), 4,4',4"-tris(N,N-diphenylamino)triphenylamine (TDATA), 4,4',4"-tris[2-naphthyl(phenyl)amino]triphenylamine (2T-NATA), polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and polyaniline)/poly(4-styrenesulfonate (PANI/PSS).

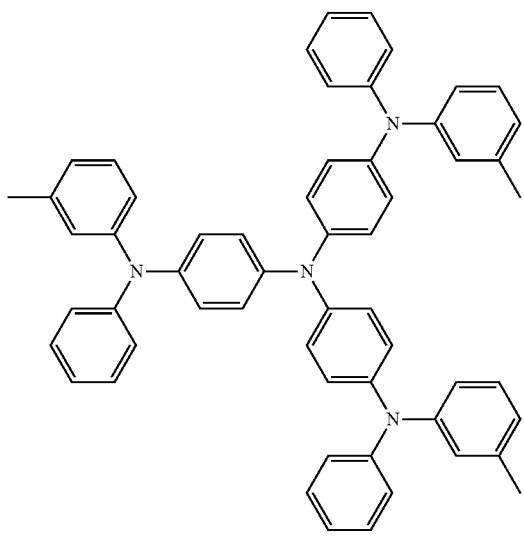

m-MTDATA

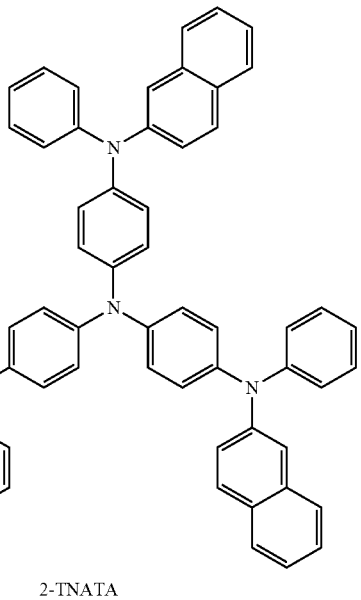

2-TNATA

The thickness of the HIL may be from about 100 Å to about 10000 Å, and in some embodiments, may be from about 100 Å to about 1000 Å. When the thickness of the HIL is within these ranges, the HIL may have good hole injecting ability without imparting a high driving voltage to the organic light-emitting device.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those used for the formation of the HIL, though the conditions for the deposition and coating may vary according to the material that is used to form the HTL.

Non-limiting examples of suitable HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

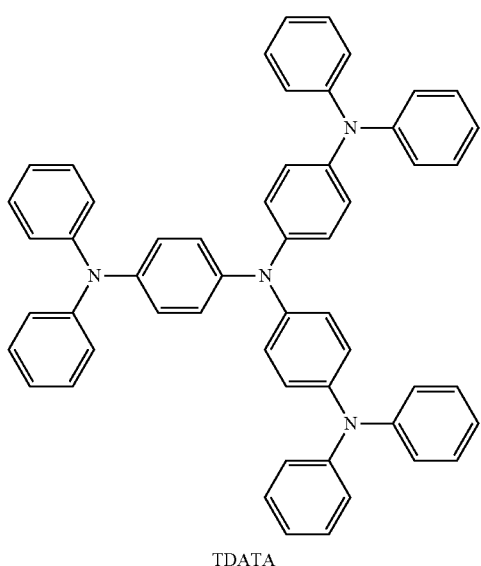

TDATA

TPD

-continued

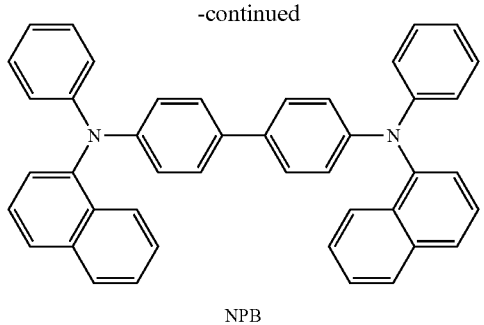

NPB

The thickness of the HTL may be from about 50 Å to about 2000 Å, and, in some embodiments, from about 100 Å to about 1500 Å. When the thickness of the HTL is within these ranges, the HTL may have good hole transporting ability without a imparting a high driving voltage to the organic light-emitting device.

The H-functional layer (having both hole injection and hole transport capabilities) may contain at least one material from each group of the hole injection layer materials and hole transport layer materials. The thickness of the H-functional layer may be from about 500 Å to about 10,000 Å, and, in some embodiments, may be from about 100 Å to about 1,000 Å. When the thickness of the H-functional layer is within these ranges, the H-functional layer may have good hole injection and transport capabilities without imparting a high driving voltage to the organic light-emitting device.

In some embodiments, at least one of the HIL, HTL, and H-functional layer may include at least one of a compound of Formula 300 below and a compound of Formula 301 below:

<Formula 300>

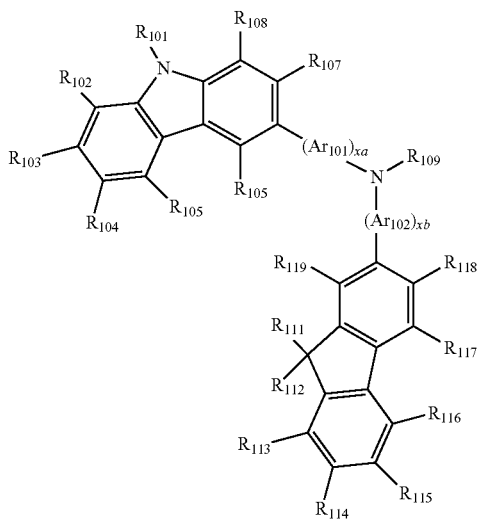

<Formula 301>

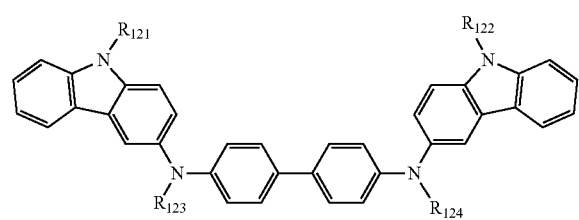

In Formula 300, $Ar_{101}$ and $Ar_{102}$ may be each independently a substituted or unsubstituted $C_6$-$C_{60}$ arylene group. For example, $Ar_{101}$ and $Ar_{102}$ may be each independently one of a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthrylene group, a fluoranthenylene group, a triphenylenylene group, a pyrenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthrylene group, a fluoranthenylene group, a triphenylenylene group, a pyrenylene group, a chrysenylene group, a naphthacenylene group, a picenylene group, a perylenylene group, and a pentacenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

In Formula 300, xa and xb may be each independently an integer from 0 to 5, or may be 0, 1 or 2. For example, xa may be 1, and xb may be 0, but not limited thereto.

In Formulae 300 and 301, $R_{101}$ to $R_{108}$, $R_{111}$ to $R_{119}$, and $R_{121}$ to $R_{124}$ may be each independently selected from a hydrogen atom, a deuterium atom, a halogen atom, a hydroxyl group, cyano group, nitro group, an amino group, an amidino group, a hydrazine, a hydrazone, carboxyl group or a salt thereof, sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group. For example, $R_{51}$ to $R_{58}$, $R_{61}$ to $R_{69}$, and $R_{71}$ and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, one of a methyl group, an ethyl group, a propyl group, a butyl group, a pentyl group, a hexyl group, and the like); a $C_1$-$C_{10}$ alkoxy group (for example, one of a methoxy group, an ethoxy group, a propoxy group, a butoxy group, a pentoxy group, and the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; phenyl group; naphthyl group; anthryl group; fluorenyl group; pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group, but not limited thereto.

In Formula 300, $R_{109}$ may be one of a phenyl group; a naphthyl group; an anthryl group; a biphenyl group; a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, carboxyl group or a salt thereof, sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below, but is not limited thereto <Formula 300A>

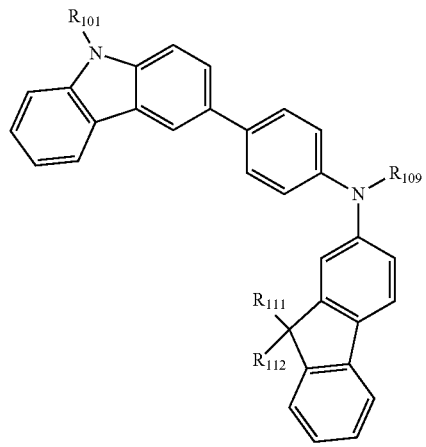

In Formula 300A, $R_{101}$, $R_{110}$, $R_{121}$, and $R_{109}$ may be as defined above.

In some non-limiting embodiments, at least one of the HIL, HTL, and H-functional layer may include at least one of compounds represented by Formulae 301 to 320 below:

301

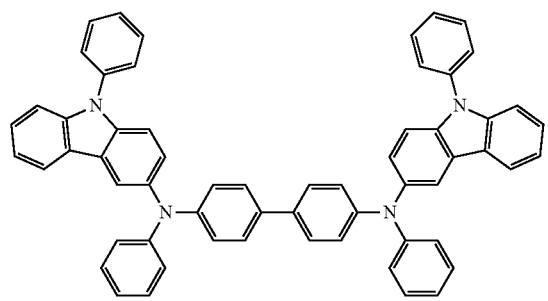

302

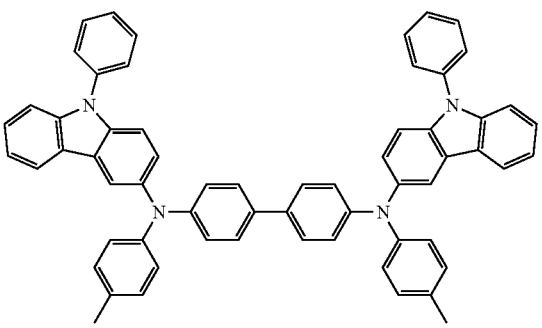

303

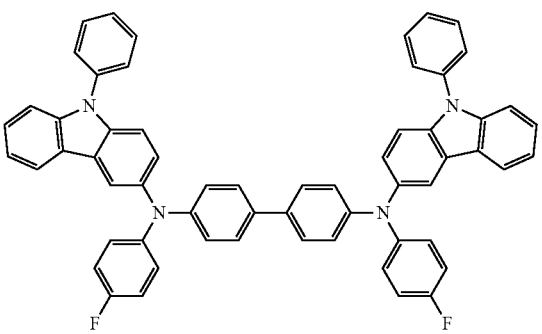

304

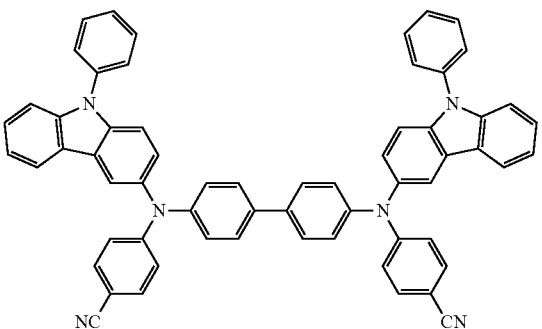

305

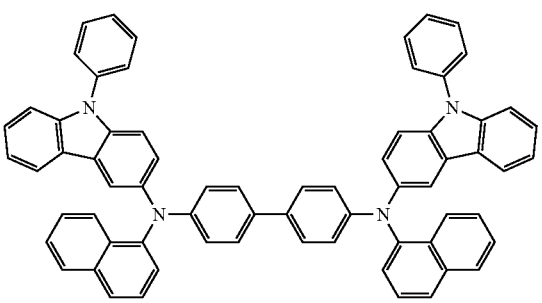

306
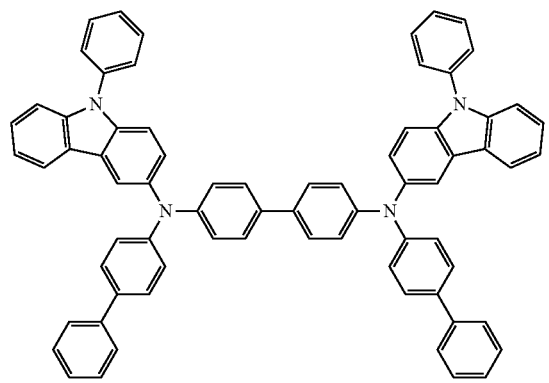
307
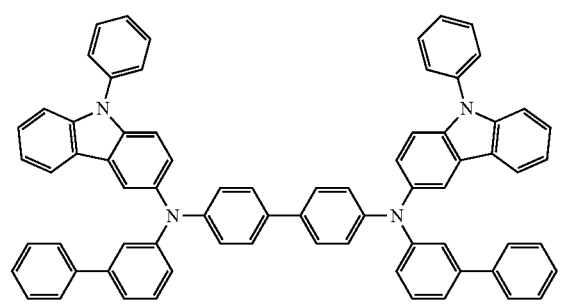
308
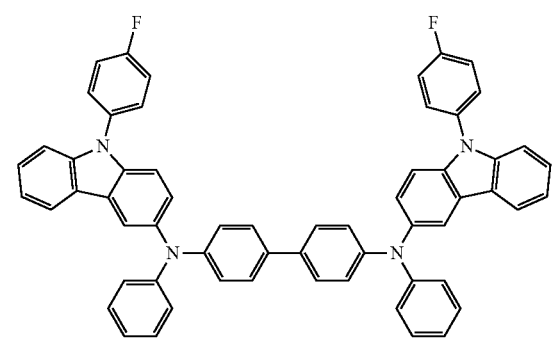
309
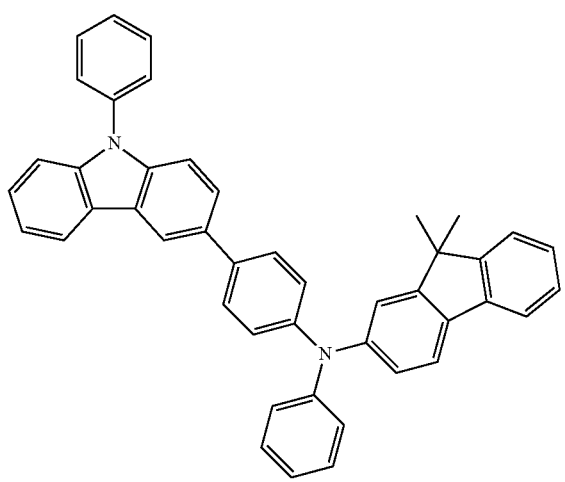
310
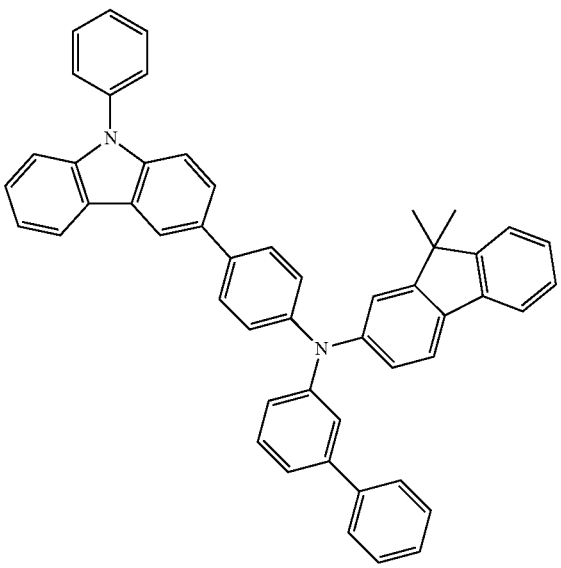
311
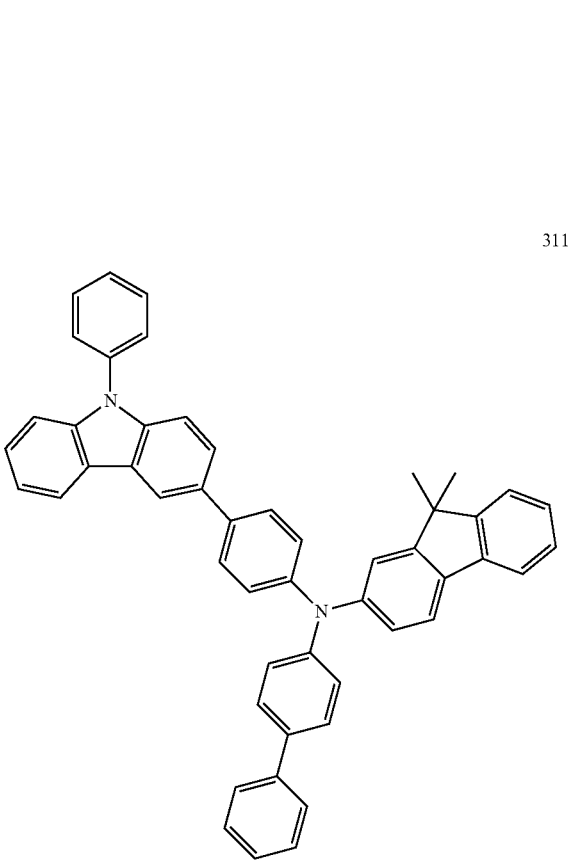

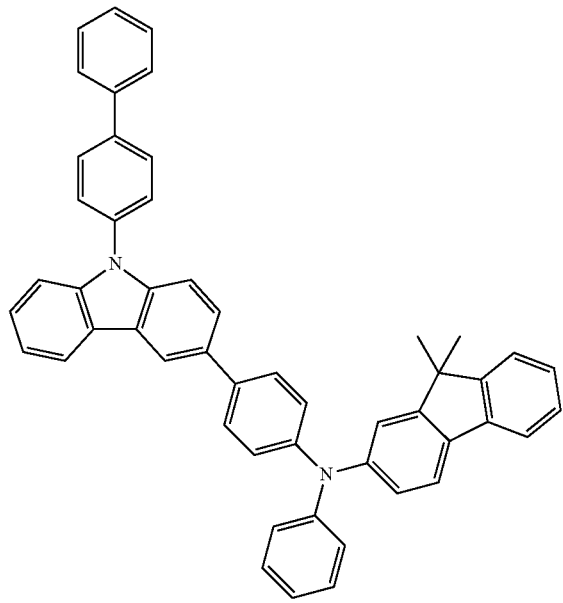
312
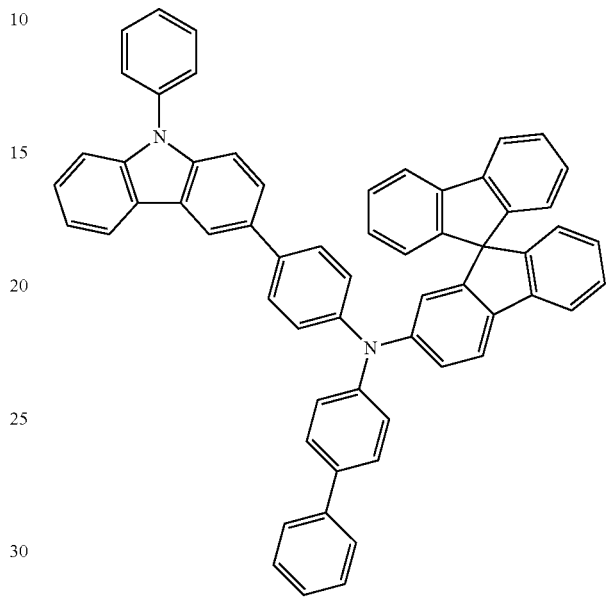
314
313
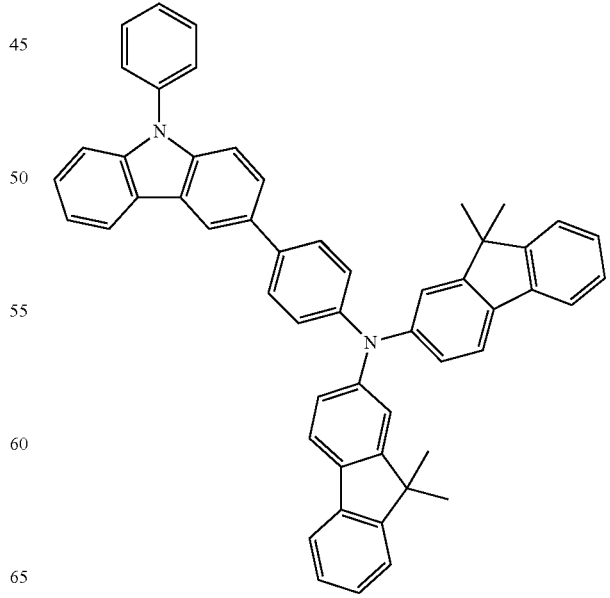
315

316
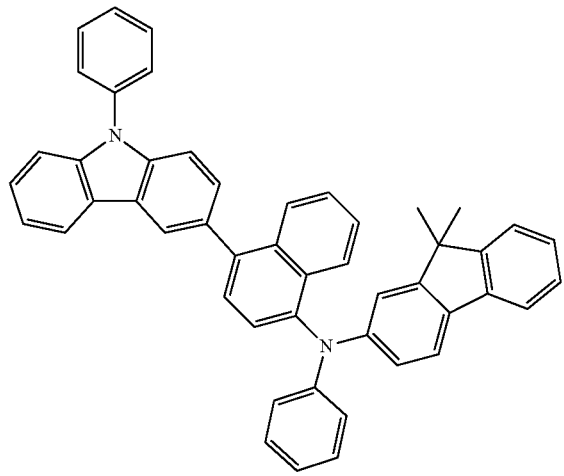
318
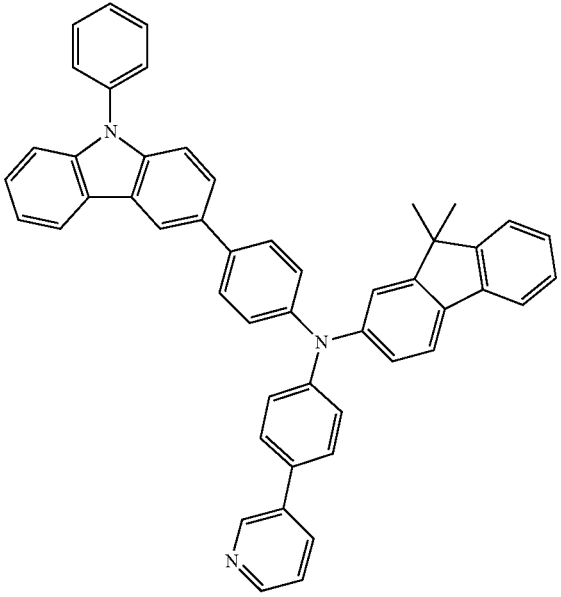
317
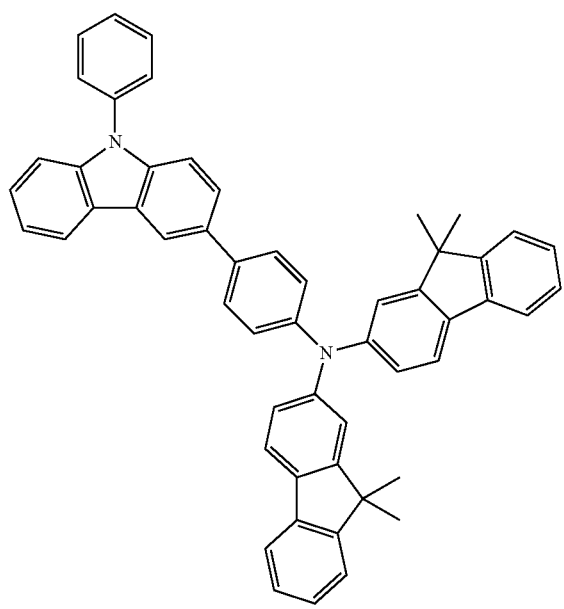
319
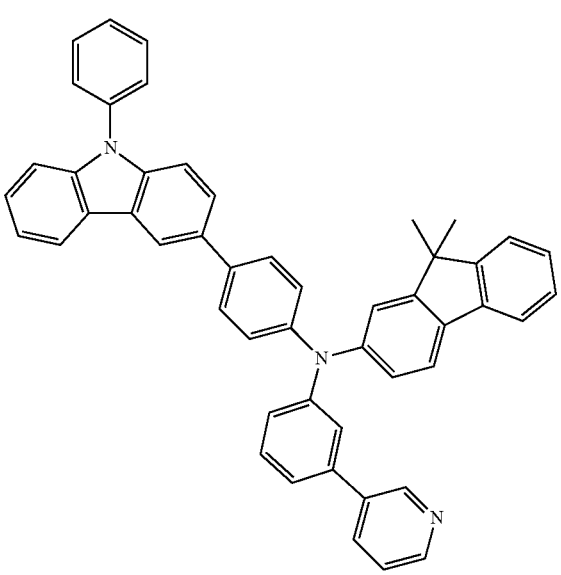

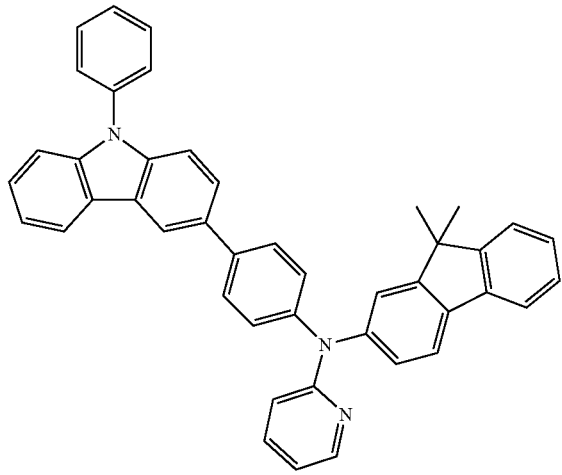

320

At least one of the HIL, HTL, and H-functional layer may further include a charge-generating material for improved layer conductivity, in addition to a hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

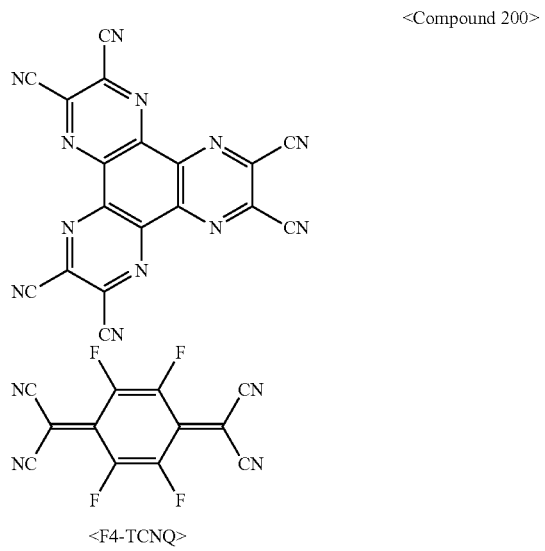

<Compound 200>

<F4-TCNQ>

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light corresponding to a wavelength of the light emitted from the EML, and thus may increase efficiency. The buffer layer may include at least one of a hole injecting material and a hole transporting material. In some other embodiments, the buffer layer may include the same material as one of the materials included in the HIL, HTL, and H-functional layer that underly the buffer layer.

Then, an EML may be formed on the HTL, H-functional layer, or buffer layer by one of vacuum deposition, spin coating, casting, Langmuir-Blodget (LB) deposition, and the like. When the EML is formed using vacuum deposition or spin coating, the deposition and coating conditions may be similar to those for the formation of the HIL, though the conditions for deposition and coating may vary according to the material that is used to form the EML.

The EML may include the organometallic compound (dopant) of Formula 1 described above and a host.

The amount of a dopant in the EML (i.e., the organometallic compound of Formula 1) may be from about 0.01 parts to about 15 parts by weight based on 100 parts by weight of the host, but is not limited thereto.

The thickness of the EML may be from about 100 Å to about 1000 Å, and in some embodiments, may be from about 200 Å to about 600 Å. When the thickness of the EML is within these ranges, the EML may have good light emitting ability without imparting a high driving voltage to the organic light-emitting device.

A hole blocking layer (HBL) may be formed on the EML in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Non-limiting examples of useful hole-blocking materials are oxadiazole derivatives, triazole derivatives, and phenanthroline derivatives. For example, bathocuproine (BCP), represented by the following formula, may be used as a material for forming the HBL.

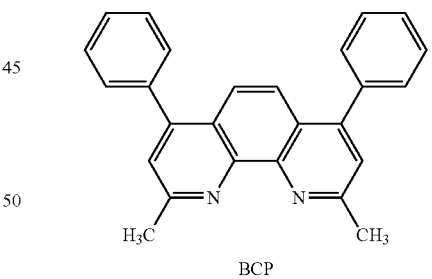

BCP

The thickness of the HBL may be from about 20 Å to about 1,000 Å, and, in some embodiments, from about 30 Å to about 300 Å. When the thickness of the HBL is within these ranges, the HBL may have improved hole blocking ability without imparting a high driving voltage to the organic light-emitting device.

Then, an ETL may be formed on the HBL by any of a variety of methods, for example, one of vacuum deposition, spin coating, and casting. When the ETL is formed using vacuum deposition or spin coating, the deposition and coating conditions may be similar to those for the formation of the HIL, though the deposition and coating conditions may vary according to the material that is used to form the ETL. A material for forming the ETL may be any material that can stably transport electrons injected from an electron injecting electrode (cathode). Non-limiting examples of materials useful for forming the ETL are a quinoline derivative, such as tris(8-quinolinato)aluminum (Alq3), 3-phenyl-4-(1'naphthyl)-5-phenyl-1,2,4-triazole (TAZ), bis(2-methyl-8-quinolinato)-4-phenylphenolate aluminum (BAlq), beryllium bis(benzoquinolin-10-olate) (Bebq$_2$), 9,10-di(naphthalene-2-yl)anthracene (ADN), Compound 201, and Compound 202, but are not limited thereto.

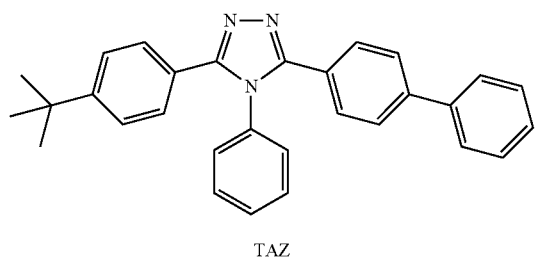

TAZ

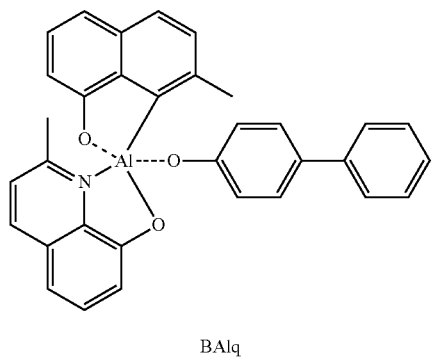

BAlq

<Compound 201>

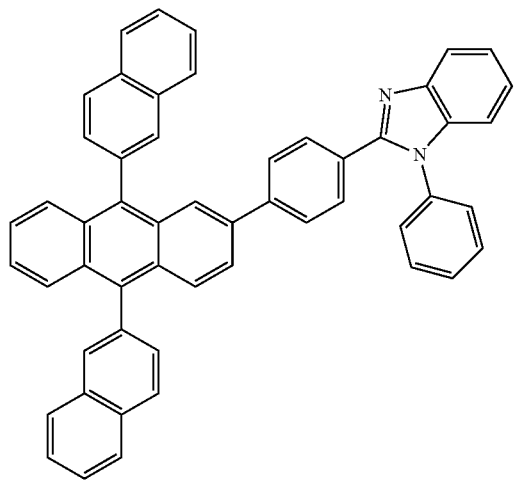

<Compound 202>

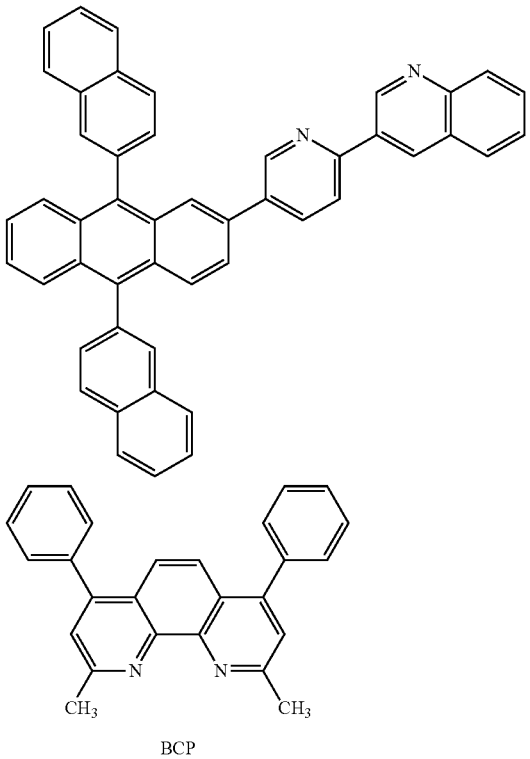

BCP

The thickness of the ETL may be from about 100 Å to about 1000 Å, and in some embodiments, from about 150 Å to about 500 Å. When the thickness of the ETL is within these ranges, the ETL may have satisfactory electron transporting ability without imparting a high driving voltage to the organic light-emitting device.

In some embodiments, the ETL may further include a metal-containing material, in addition to an electron-transporting organic compound.

The metal-containing material may be a lithium (Li) compound. Non-limiting examples of the Li compound are lithium quinolate (LiQ) and Compound 203 below:

<Compound 203>

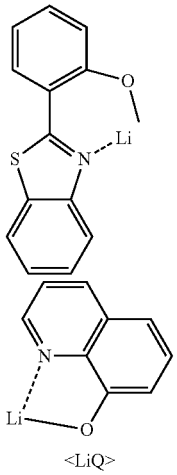

<LiQ>

Then, an EIL, which facilitates injection of electrons from the cathode, may be formed on the ETL. Any suitable electron-injecting material may be used to form the EIL.

Non-limiting examples of materials useful for forming the EIL are LiF, NaCl, CsF, $Li_2O$, and BaO. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, may be from about 3 Å to about 90 Å. When the thickness of the EIL is within these ranges, the EIL may have satisfactory electron injection ability without imparting a high driving voltage to the organic light-emitting device.

The second electrode 17 is disposed on the organic layer 15. The second electrode 17 may be a cathode that is an electron injection electrode. A material for forming the second electrode 17 may be one of a metal, an alloy, an electro-conductive compound and a mixture thereof, the material having a low work function. In some embodiments, the second electrode 190 as a transmission electrode may be formed using a thin film comprising one of Li, Mg, Al, Al—Li, Ca, Mg—In, Mg—Ag, and the like. In some embodiments, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

Hereinafter, the present invention will be described in detail with reference to the following synthesis examples and other examples. However, these examples are for illustrative purposes only and are not intended to limit the scope of the present invention.

As used herein, examples of the unsubstituted $C_1$-$C_{60}$ alkyl group (or $C_1$-$C_{60}$ alkyl group) are linear or branched $C_1$-$C_{60}$ alkyl groups, such as methyl, ethyl, propyl, isobutyl, sec-butyl, pentyl, iso-amyl, or hexyl. Examples of the substituted $C_1$-$C_{60}$ alkyl group are the unsubstituted $C_1$-$C_{60}$ alkyl group of which at least one hydrogen atom is substituted with one of a deuterium atom, a halogen atom, a hydroxy group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one hydrogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —$N(Q_{11})(Q_{12})$, and —$Si(Q_{13})(Q_{14})(Q_{15})$ ($Q_{11}$ to $Q_{15}$ each being, independently, one of a hydrogen atom, a $C_1$-$C_{10}$ alkyl group, a $C_6$-$C_{20}$ aryl group, and a $C_2$-$C_{20}$ heteroaryl group) a $C_2$-$C_{60}$ alkenyl group, a $C_2$-$C_{60}$ alkynyl group, a $C_6$-$C_{60}$ aryl group, a $C_2$-$C_{60}$ heteroaryl group, —$N(Q_{11})(Q_{12})$, and —$Si(Q_{13})(Q_{14})(Q_{15})$ (where $Q_{11}$ to $Q_{15}$ are each independently selected from a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group).

As used herein, the unsubstituted $C_1$-$C_{60}$ alkoxy group (or $C_1$-$C_{60}$ alkoxy group) may be represented by the formula of —OA (wherein A is an unsubstituted $C_1$-$C_{60}$ alkyl group as described above). Examples of the unsubstituted $C_1$-$C_{60}$ alkoxy group are methoxy, ethoxy, and isopropyloxy groups. At least one hydrogen atom of the unsubstituted $C_1$-$C_{60}$ alkoxy group may be substituted with those substituents described above in conjunction with the substituted $C_1$-$C_{60}$ alkyl group.

As used herein, the unsubstituted $C_2$-$C_{60}$ alkenyl group (or a $C_2$-$C_{60}$ alkenyl group) is a hydrocarbon chain having a carbon-carbon double bond in the center or at a terminal of the unsubstituted $C_2$-$C_{60}$ alkyl group. Examples of the unsubstituted $C_2$-$C_{60}$ alkenyl group are ethenyl, prophenyl, and butenyl groups. At least one hydrogen atom of the unsubstituted $C_2$-$C_{60}$ alkenyl group may be substituted with those substituents described above in conjunction with the substituted $C_1$-$C_{60}$ alkyl group.

As used herein, the unsubstituted $C_2$-$C_{60}$ alkynyl group (or a $C_2$-$C_{60}$ alkynyl group) is a hydrocarbon chain having a carbon-carbon triple bond in the center or at a terminal of the above-defined $C_2$-$C_{60}$ alkyl group. Examples of the unsubstituted $C_2$-$C_{60}$ alkynyl group are ethynyl and propynyl groups. At least one hydrogen atom of the unsubstituted $C_2$-$C_{60}$ alkynyl group may be substituted with those substituents described above in conjunction with the substituted $C_1$-$C_{60}$ alkyl group.

As used herein, the unsubstituted $C_6$-$C_{60}$ aryl group is a monovalent group having a carbocyclic aromatic system having 6 to 60 carbon atoms including at least one aromatic group. The unsubstituted $C_6$-$C_{60}$ arylene group is a divalent group having a carbocyclic aromatic system having 6 to 60 carbon atoms including at least one aromatic group. When the aryl group and the arylene group, respectively, have at least two rings, they may be fused to each other. At least one hydrogen atom of the aryl group and the arylene group may be substituted with those substituents described above in conjunction with the substituted $C_1$-$C_{60}$ alkyl group.

Examples of the substituted or unsubstituted $C_6$-$C_{60}$ aryl group are a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, o-, m- and p-fluorophenyl groups, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, an azrenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenylgroup, a coroneryl group, a trinaphthylenyl group, a heptaphenyl group, a heptacenyl group, a piranthrenyl group, and an obarenyl group. Examples of the substituted $C_5$-$C_{60}$ aryl group may be understood based on the above-described examples of the unsubstituted $C_5$-$C_{60}$ aryl group and substituents of the substituted $C_1$-$C_{60}$ alkyl group. Examples of the substituted or unsubstituted $C_5$-$C_{60}$ arylene group may be understood based on the above-described examples of the substituted or unsubstituted $C_5$-$C_{60}$ aryl group.

As used herein, the unsubstituted $C_2$-$C_{60}$ heteroaryl group is a monovalent group having at least one aromatic group, the aromatic group having at least one of the heteroatoms selected from N, O, P, and S and having at least one carbon atom. The unsubstituted $C_2$-$C_{60}$ heteroarylene group is a divalent group having at least one aromatic group, the aromatic group having at least one of the heteroatoms selected from N, O, P, and S and having at least one carbon atom. In this regard, when the heteroaryl group and the heteroarylene group, respectively, have at least two rings, they may be fused to each other. At least one hydrogen atom from one or both of the heteroaryl group and the heteroarylene group may be substituted with those substituents described above in conjunction with the substituted $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ hetero arylene group may be understood based on the above-described examples of the substituted or unsubstituted $C_2$-$C_{60}$ arylene group.

The substituted or unsubstituted $C_6$-$C_{60}$ aryloxy group is represented by —$OA_2$ (where $A_2$ is a substituted or unsubstituted $C_6$-$C_{60}$ aryl group as described above). The substituted or unsubstituted $C_6$-$C_{60}$ arylthio group is —$SA_3$ (where $A_3$ is a substituted or unsubstituted $C_6$-$C_{60}$ aryl group as described above).

SYNTHESIS EXAMPLE

Synthesis Example 1

Synthesis of Compound 2

Compound 2 was synthesized according to Reaction Scheme 1 below:

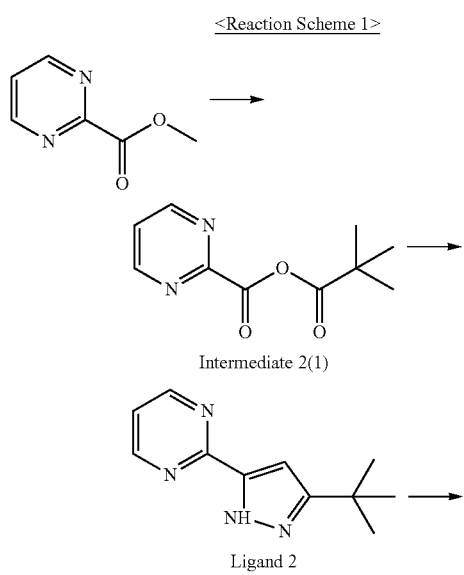

Intermediate 2(1)

Ligand 2

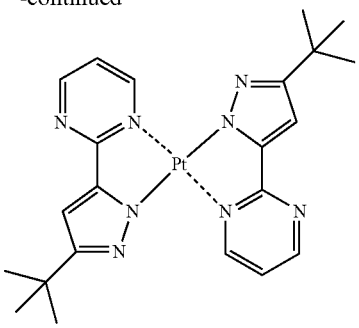

Compound 2

Synthesis of Intermediate 2(1)

A quantity of 0.35 g (8.7 mmol) of NaH was put in 50 ml of anhydrous tetrahydrofuran, followed by an addition of 0.7 g (7.24 mmol) of dimethyl-2-butanone at about 0° C. to obtain a mixture, which was then stirred for about 30 minutes. Afterward, 1.0 g (7.24 mmol) of pyrimidine-2-carboxylic acid methyl ester dissolved in 10 ml of anhydrous tetrahydrofuran was slowly added to the mixtures at about 0° C., and stirred for about 1 hour, and then further at about 80° C. for about 18 hours. After completion of the reaction, 50 ml of distilled water was added to the reaction product, which was then extracted three times with 100 ml portions of methylene chloride. The organic layer was collected, dried using anhydrous magnesium sulfate, then distilled under reduced pressure. The resulting reaction mixture was separated and purified using column chromatography to obtain 0.8 g (3.8 mmol) of Intermediate 2(1) (Yield 52%). This compound was identified using liquid chromatography-mass spectroscopy (LC-MS) and $^1$H nuclear magnetic resonance (NMR).

LC-MS m/z=207(M+H)$^+$ $^1$H NMR(300MHz, CDCl$_3$) δ=9.01(d, 2H), 7.72(m, 1H), 6.81(s, 1H), 1.15(s, 9H)

Synthesis of Ligand 2

A quantity of 0.8 g (3.8 mmol) of Intermediate 2(1) was dissolved in 30 ml of ethanol, followed by an addition of 19 ml (19.0 mmol) of hydrazine hydrate to obtain a mixture, which was then heated under reflux. After completion of reaction, the reaction product was neutralized with a 4M aqueous hydrochloric acid solution, then concentrated using a reduced-pressure distillation system. The concentrated compound was extracted with 70 ml of distilled water and then 100 ml of methylene chloride. The organic layer was collected, dried using anhydrous magnesium sulfate, then distilled under reduced pressure to obtain a reaction product mixture. The reaction product mixture was separated and purified using column chromatography to obtain 0.45 g (2.3 mmol) of ligand 2 (Yield 60%). This compound was identified using LC-MS and $^1$H NMR.

LC-MS m/z=203(M+H)$^+$ $^1$H NMR(300MHz, CDCl$_3$) δ=8.92 (d, 2H), 7.41(m, 1H), 6.73(s, 1H), 1.34(s, 9H)

Synthesis of Compound 2

A quantity of 0.4 g (1.98 mmol) of ligand 2 was dissolved in a mixed solvent of 30 ml of ethanol and 10 ml of distilled water, followed by an addition of 0.42 g (1.0 mmol) of K$_2$PtCl$_4$ to obtain a mixture, which was then heated under reflux for 16 hours. The completion of the reaction was confirmed using LC-MS, and the resulting reaction mixture was filtered to obtain 0.5 g (0.8 mmol) of Compound 2 (Yield 80%). This compound was identified using LC-MS and $^1$H NMR.

LC-MS m/z=598(M+H)$^+$ $^1$H NMR(300MHz, CDCl$_3$) δ=9.32 (d, 4H), 8.71(m, 2H), 6.85(s, 2H), 1.27(s, 18H)

Synthesis Example 2

Synthesis of Compound 1

Compound 1 was synthesized according to Reaction Scheme 1 below:

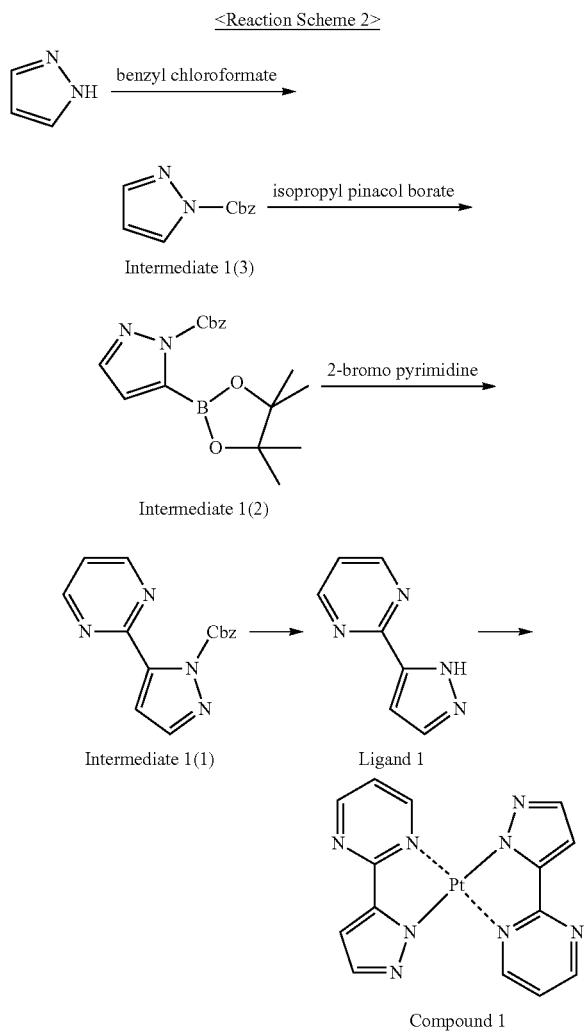

Synthesis of Intermediate 1(3)

A quantity of 1.9 g (80.8 mmol) of NaH was put in 80 ml of dichloromethane, followed by an addition of 5.0 g (73.5 mmol) of pyrazole at 0° C. to obtain a mixture, which was then stirred for about 30 minutes. Afterward, 11.5 ml (80.8 mmol) of benzyl chloroformate dissolved in 30 ml of dichloromethane was dropwise added to the mixture at 0° C., then stirred for about 1 hour, and then further stirred at room temperature for 3 hours. After completion of the reaction, 100 ml of a saturated aqueous sodium hydrogen carbonate solution was added to the reaction product, which was then extracted three times with 50 ml portions of methylene chloride. The organic layer was collected, dried using anhydrous magnesium sulfate, and then distilled under reduced pressure. The resulting product was separated and purified using column chromatography to obtain 12.6 g (62.4 mmol) of Intermediate 1(3) (Yield 85%). This compound was identified using LC-MS.

LC-MS m/z=203(M+H)$^+$

Synthesis of Intermediate 1(2)

A quantity of 10.0 g (49.5 mmol) of Intermediate 1(3) was dissolved in 80 ml of anhydrous tetrahydrofuran, and 25 ml (54.5 mmol) of n-BuLi (2.2M in THF) was slowly added thereto, then stirred at room temperature for about 1 hour. Then, the temperature was lowered to about −78° C., and 12.0 ml (59.4 mmol) of isopropyl pinacol borate was slowly added to the reaction mixture, which was then stirred at about −78° C. for about 15 minutes, then further stirred for about 1 hour while the temperature slowly increased to 0° C. After completion of the reaction, 100 ml of a saturated aqueous ammonium chloride solution was added to the reaction mixture, which was then extracted with 100 ml of dichloromethane. The organic layer was collected and washed twice with 100 ml of distilled water, dried using anhydrous magnesium sulfate, then distilled with reduced pressure to obtain 9.7 g (29.7 mmol) of Intermediate 1(2).

LC-MS m/z=329(M+H)$^+$

Synthesis of Intermediate 1(1)

A quantity of 1.9 g (12.2 mmol) of 2-bromo pyrimidine was dissolved in 120 ml of a mixed solvent of dioxolane and water (5:1) in a seal-tube, and 5.0 g (36.6 mmol) of potassium carbonate, 1.4 g (1.2 mmol) of tetrakistriphenyl-phosphine Pd(0), and 8.0 g (24.4 mmol) of Intermediate 1(2) were added thereto. The resulting reaction mixture was stirred at about 90° C. overnight. After completion of the reaction, 100 ml of distilled water was added to the reaction product, which was then extracted with 100 ml of dichloromethane. The organic layer was collected dried using anhydrous magnesium sulfate, and then distilled under reduced pressure to obtain Intermediate 1(1) (7.3 mmol, Yield 60%).

LC-MS m/z=281(M+H)$^+$

Synthesis of Ligand 1

A quantity of 2.0 g (7.3 mmol) of Intermediate 1(1) was dissolved in 60 ml of methanol at room temperature, followed by an addition of 0.2 g (10% w/w) of Pd/C to obtain a mixture, which was then stirred at room temperature for about 12 hours while hydrogen was supplied thereto. After completion of the reaction, Pd/C was removed using celite. Afterward, the organic layer was collected and concentrated under reduced pressure. The resulting product was separated and purified using column chromatography to obtain ligand 1 (6.9 mmol, Yield 95%). This compound was identified using LC-MS.

LC-MS m/z=147(M+H)$^+$

Synthesis of Compound 1

Compound 1 (0.5 mmol, Yield 7%) was synthesized in the same manner as was Compound 2 in Synthesis Example 1, except that ligand 1, instead of ligand 2, was used. This compound was identified using LC-MS and NMR.

LC-MS m/z=486(M+H)$^+$ $^1$H NMR(300MHz, CDCl$_3$) δ=9.41 (d, 8H), 7.68(d, 4H), 7.32(m, 4H), 6.77(d, 4H)

Synthesis Example 3

Synthesis of Compound 3

<Reaction Scheme 3>

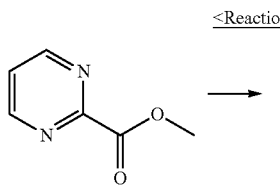

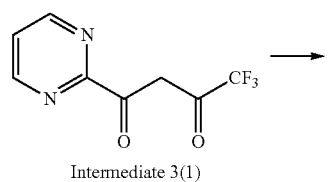

Intermediate 3(1)

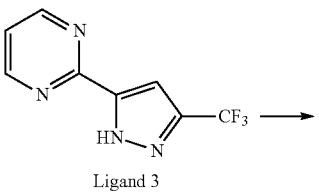

Ligand 3

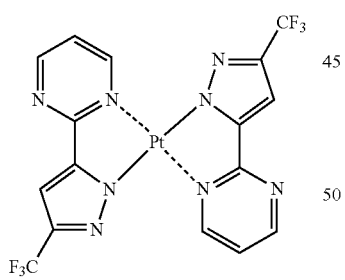

Compound 3

Compound 3 (Yield 53%) was synthesized in the same manner as described in Synthesis Example 1, via the synthesis of Intermediate 3(1), ligand 3, and Compound 3 according to Reaction Scheme 3, except that 1,1,1-trifluoropropan-2-one, instead of the dimethyl-2-butanone used in the synthesis of Intermediate 2(1), was used. This compound was identified using LC-MS and NMR.

LC-MS m/z=622(M+H)$^+$ $^1$H NMR(300MHz, CDCl$_3$) δ=10.32(d, 4H), 9.26(m, 2H), 6.93(s, 2H)

Synthesis Example 4

Synthesis of Compound 4

<Reaction Scheme 4>

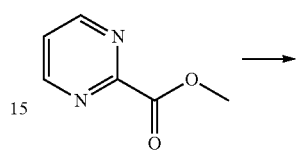

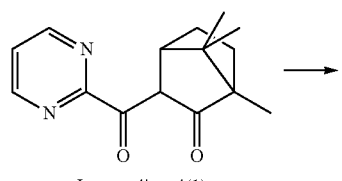

Intermediate 4(1)

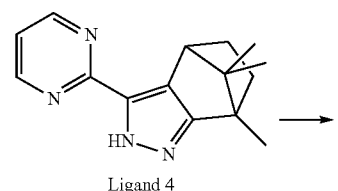

Ligand 4

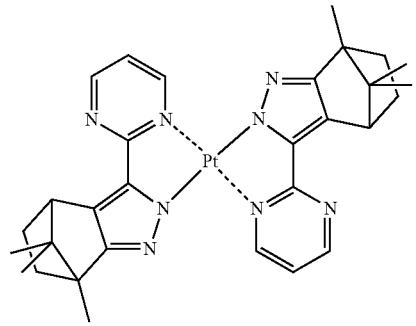

Compound 4

Compound 4 (Yield 68%) was synthesized in the same manner as described in Synthesis Example 1, via the synthesis of Intermediate 4(1), ligand 4, and Compound 4 according to Reaction Scheme 4, except that camphor, instead of the dimethyl-2-butanone used in the synthesis of Intermediate 2(1), was used. This compound was identified using LC-MS and NMR.

LC-MS m/z=702(M+H)$^+$ $^1$H NMR(300MHz, CDCl$_3$) δ=10.28(d, 4H), 9.23(m, 2H), 2.77(br s, 2H), 1.68~1.62(m, 8H), 1.47(s, 6H), 1.11(s, 12H)

Synthesis Example 5

Synthesis of Compound 5

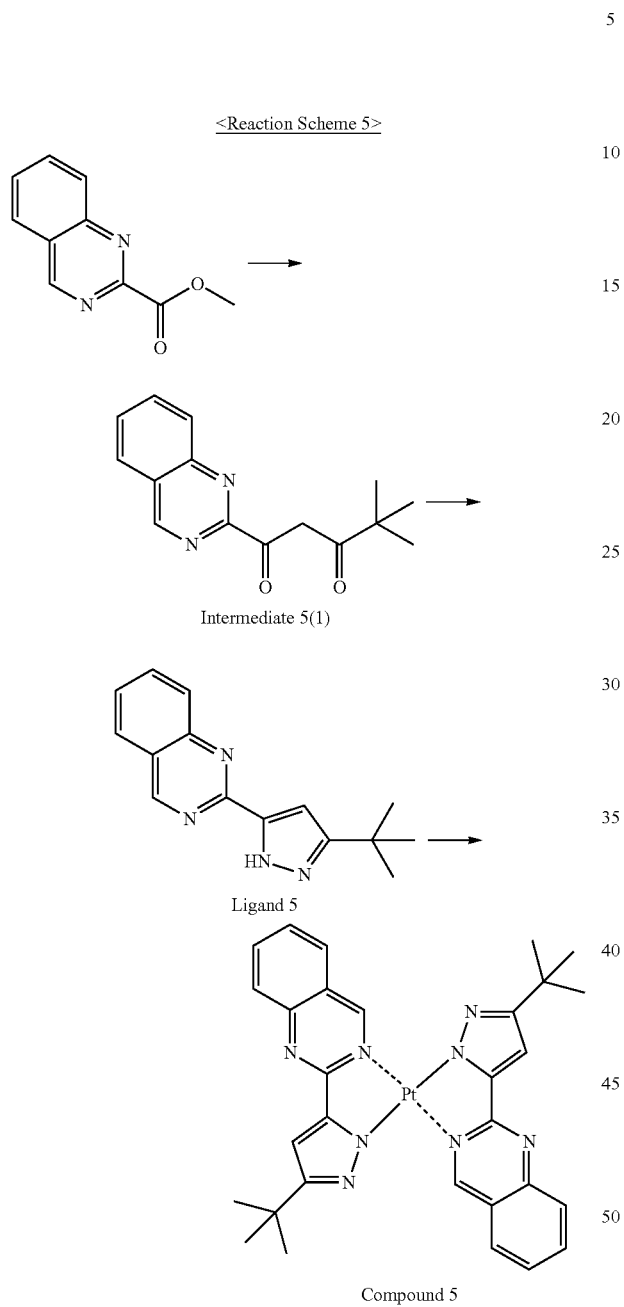

Compound 5

Compound 5 (Yield 45%) was synthesized in the same manner as described in Synthesis Example 1, via the synthesis of Intermediate 5(1), ligand 5, and Compound 5 according to Reaction Scheme 5, except that methyl quinazoline-2-carboxylate, instead of the pyrimidine-2-carboxylic acid methyl ester used in the synthesis of Intermediate 2(1), was used. This compound was identified using LC-MS and NMR.

LC-MS m/z=698(M+H)$^+$ $^1$H NMR(300MHz, CDCl$_3$) δ=10.58(d, 4H), 9.03(d, 2H), 7.83-7.80 (m, 4H), 7.68 (m, 2H), 6.86 (s, 2H), 1.26 (s, 18H)

Synthesis Example 6

Synthesis of Compound 6

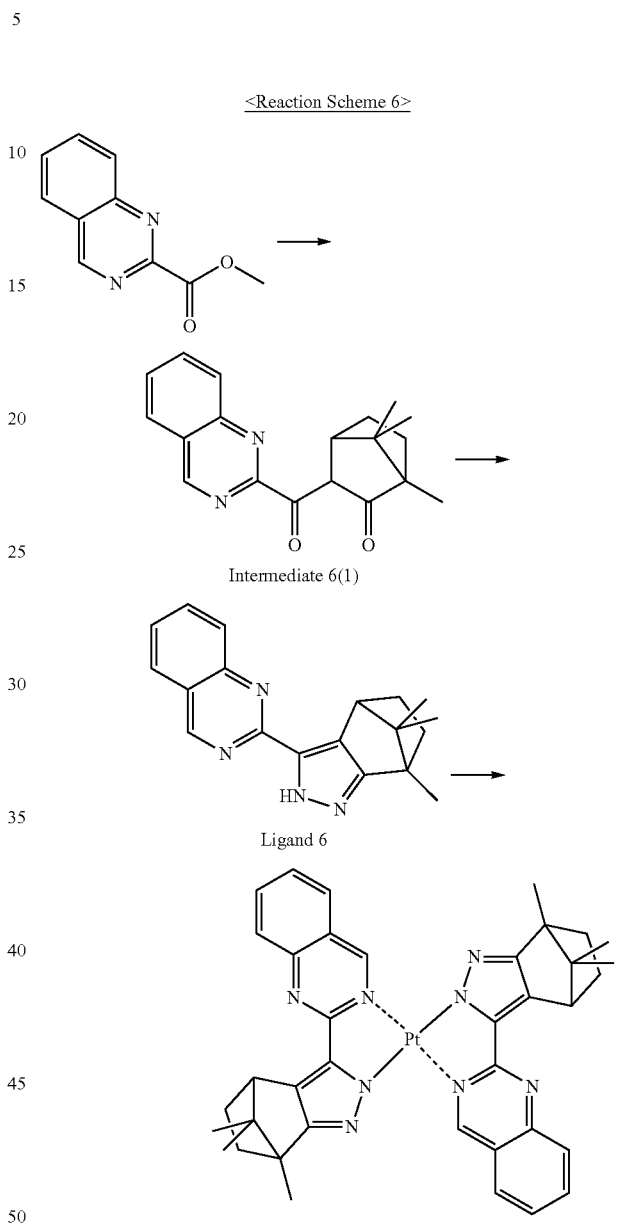

Compound 6

Compound 6 (Yield 43%) was synthesized in the same manner as described in Synthesis Example 1, via the synthesis of Intermediate 6(1), ligand 6, and Compound 6 according to Reaction Scheme 6, except that methyl quinazoline-2-carboxylate and camphor, respectively, instead of the pyrimidine-2-carboxylic acid methyl ester and the dimethyl-2-butanone used in the synthesis of Intermediate 2(1), were used. Compound 6 was identified using LC-MS and NMR.

LC-MS m/z=802(M+H)$^+$ $^1$H NMR(300MHz, CDCl$_3$) δ=10.61(d, 4H), 9.16(d, 2H), 7.85-7.81 (m, 4H), 2.82(br s, 2H), 1.71~1.66(m, 8H), 1.51(s, 6H), 1.12(s, 12H)

Synthesis Example 7

Synthesis of Compound 7

Compound 7 was synthesized according to Reaction Scheme 7 below:

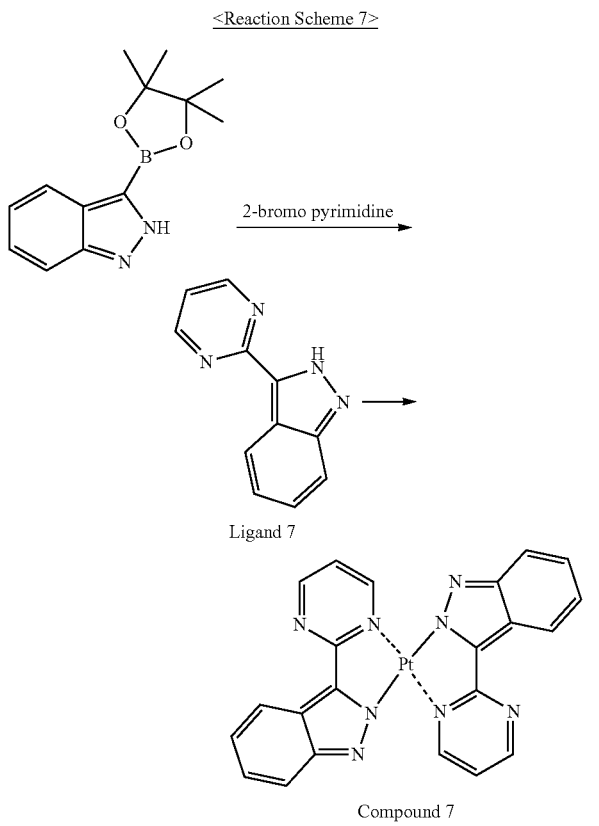

Synthesis of Ligand 7

A quantity of 2.0 g (12.6 mmol) of 2-bromo pyrimidine was dissolved in 80 ml of 1,2-dimethoxyethane at room temperature, followed by an addition of 1.4 g (1.2 mmol) of tetrakistriphenylphosphine) Pd(0) and 4.6 g (18.9 mmol) of H-indazole-3-yl boronic acid pinacol ester. The resulting mixture was heated at about 90° C. for about 18 hours under reflux. After completion of the reaction, 100 ml of distilled water was added to the reaction product, which was then extracted with 100 ml of dichloromethane. The organic layer was collected, dried using anhydrous magnesium sulfate, and distilled under reduced pressure. The product residue was separated and purified using column chromatography to obtain 1.1 g (5.7 mmol) of ligand 7 (Yield 45%).

LC-MS m/z=197(M+H)$^+$

Synthesis of Compound 7

Compound 7 (Yield 38%) was synthesized in the same manner as described in the method of synthesizing Compound 1 in Synthesis Example 1, except that ligand 7, instead of ligand 2, was used. This compound was identified using LC-MS and NMR.

LC-MS m/z=586(M+H)$^+$ $^1$H NMR(300MHz, CDCl$_3$) δ=9.18(d, 4H), 7.8-7.6 (m, 4H), 7.32-7.21 (m, 6H)

Synthesis Example 8

Synthesis of Compound 8

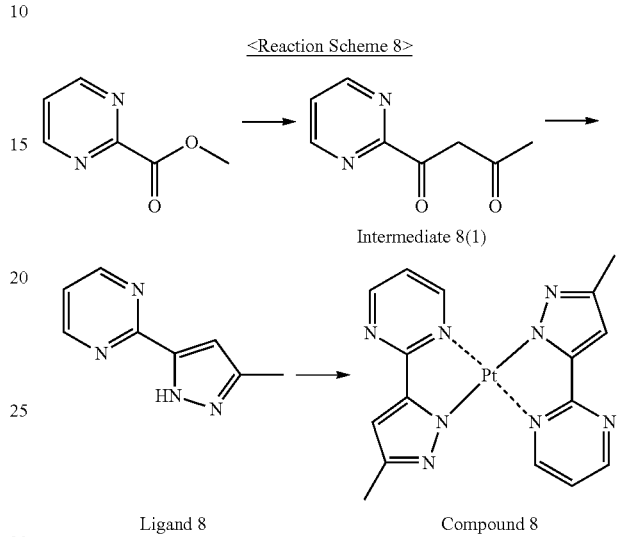

Compound 8 (Yield 62%) was synthesized in the same manner as described in Synthesis Example 8, via the synthesis of Intermediate 8(1), ligand 8, and Compound 8 according to Reaction Scheme 8, except that acetone, instead of the dimethyl-2-butanone used in the synthesis of Intermediate 2(1), was used. This compound was identified using LC-MS and NMR.

LC-MS m/z=514(M+H)$^+$ $^1$H NMR(300MHz, CDCl$_3$) δ=9.28 (d, 4H), 8.68(m, 2H), 6.87(s, 2H), 2.72(s, 6H)

Synthesis Example 9

Synthesis of Compound 9

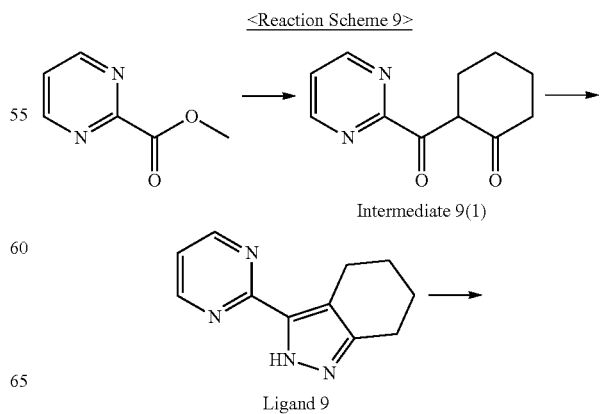

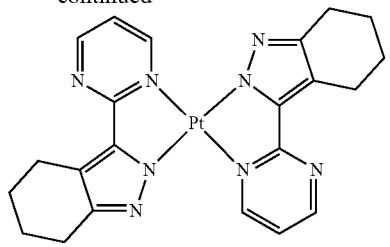

Compound 9

Compound 9 (Yield 62%) was synthesized in the same manner as described in Synthesis Example 1, via the synthesis of Intermediate 9(1), ligand 9, and Compound 9 according to Reaction Scheme 9, except that cyclohexanone, instead of the dimethyl-2-butanone used in the synthesis of Intermediate 2(1), was used. This compound was identified using LC-MS and NMR.

LC-MS m/z=594(M+H)$^+$ $^1$H NMR(300MHz, CDCl$_3$) δ=9.31 (d, 4H), 8.62(m, 2H), 2.81(br s, 4H), 2.76(br s, 4H), 1.76~1.72(br s, 8H)

Synthesis Example 10

Synthesis of Compound 10

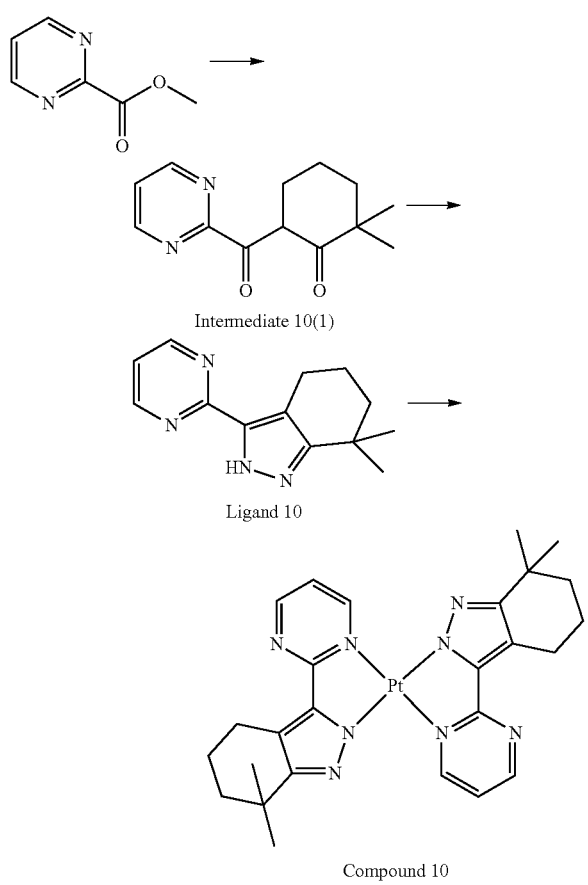

Compound 10 (Yield 47%) was synthesized in the same manner as described in Synthesis Example 1, via the synthesis of Intermediate 10(1), ligand 10, and Compound 10 according to Reaction Scheme 10, except that 2,2-dimethylcyclohexanone, instead of the dimethyl-2-butanone used in the synthesis of Intermediate 2(1), was used. This compound was identified using LC-MS and NMR.

LC-MS m/z=650(M+H)$^+$ $^1$H NMR(300MHz, CDCl$_3$) δ=9.68 (d, 4H), 9.36(m, 2H), 2.65(br s, 4H), 1.95(br s, 4H), 1.5 (br s, 4H), 1.39(s, 6H)

Synthesis Example 11

Synthesis of Compound 11

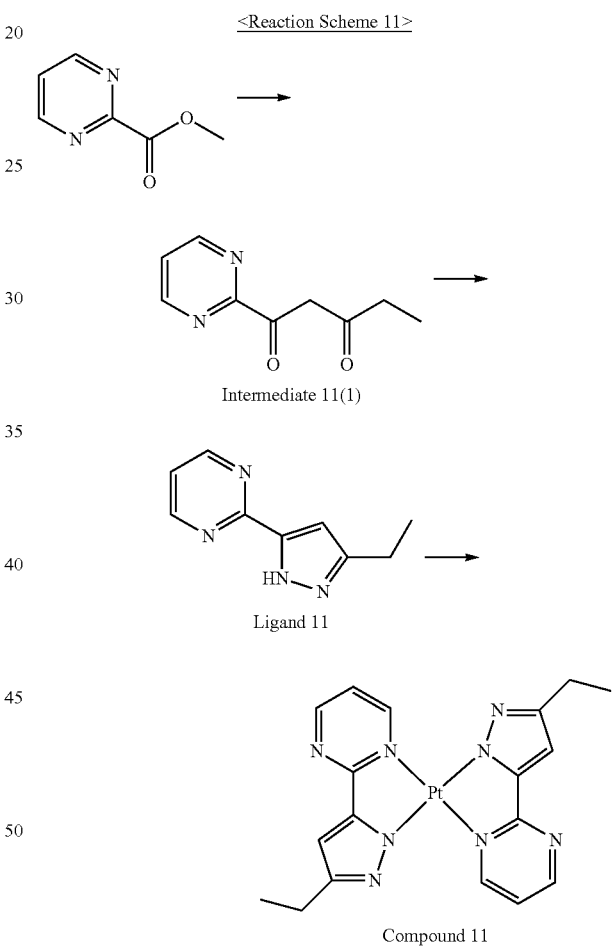

Compound 11 (Yield 31%) was synthesized in the same manner as described in Synthesis Example 1, via the synthesis of Intermediate 11(1), ligand 11, and Compound 11 according to Reaction Scheme 11, except that 3-butanone, instead of the dimethyl-2-butanone used in the synthesis of Intermediate 2(1), was used. This compound was identified using LC-MS and NMR.

LC-MS m/z=542(M+H)$^+$ $^1$H NMR(300MHz, CDCl$_3$) δ=9.84 (d, 4H), 8.62(m, 2H), 6.86(s, 2H), 2.48(q, 4H), 1.28(t, 6H)

Synthesis Example 12

Synthesis of Compound 12

<Reaction Scheme 12>

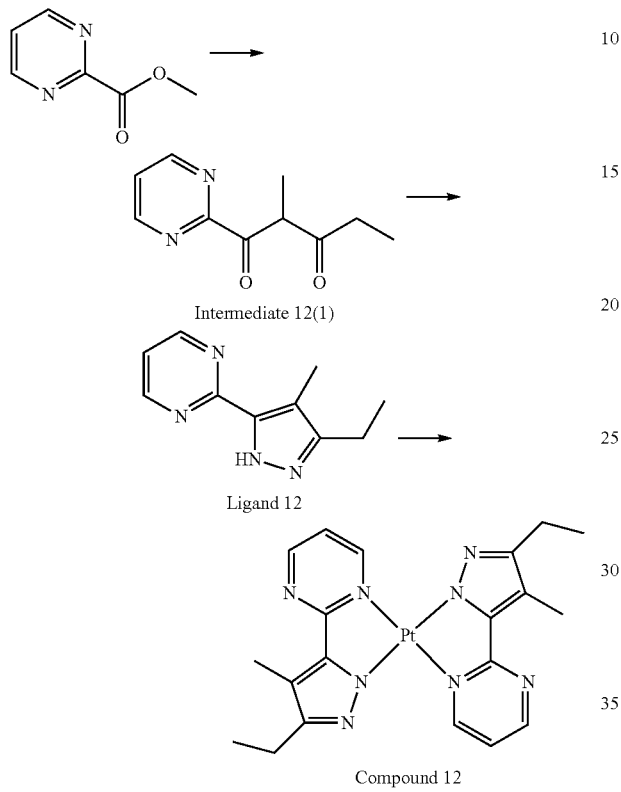

Compound 12

Compound 12 (Yield 16%) was synthesized in the same manner as described in Synthesis Example 1, via the synthesis of Intermediate 12(1), ligand 12, and Compound 12 according to Reaction Scheme 12, except that 3-pentanone, instead of the dimethyl-2-butanone used in the synthesis of Intermediate 2(1), was used. This compound was identified using LC-MS and NMR.

LC-MS m/z=570(M+H)$^+$ $^1$H NMR(300MHz, CDCl$_3$) δ=9.76 (d, 4H), 8.58(m, 2H), 2.61(q, 4H), 2.08(s, 6H), 1.26(t, 6H)

Synthesis Example 13

Synthesis of Compound 13

<Reaction Scheme 13>

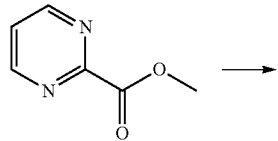

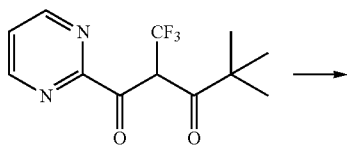

Intermediate 13(1)

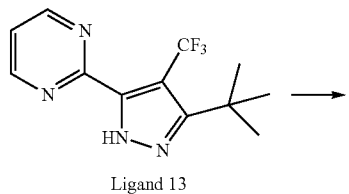

Ligand 13

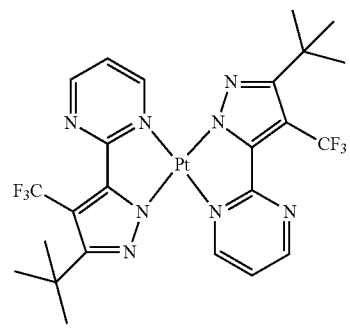

Compound 13

Compound 13 (Yield 11%) was synthesized in the same manner as described in Synthesis Example 1, via the synthesis of Intermediate 13(1), ligand 13, and Compound 13 according to Reaction Scheme 13, except that 1,1,1-trifluoro-4,4-dimethylpentan-3-one, instead of the dimethyl-2-butanone used in the synthesis of Intermediate 2(1), was used. This compound was identified using LC-MS and NMR.

LC-MS m/z=734(M+H)$^+$ $^1$H NMR(300MHz, CDCl$_3$) δ=9.51 (d, 4H), 8.65(m, 2H), 1.36(s, 18H)

Synthesis Example 14

Synthesis of Compound 14

<Reaction Scheme 14>

Intermediate 14(1)

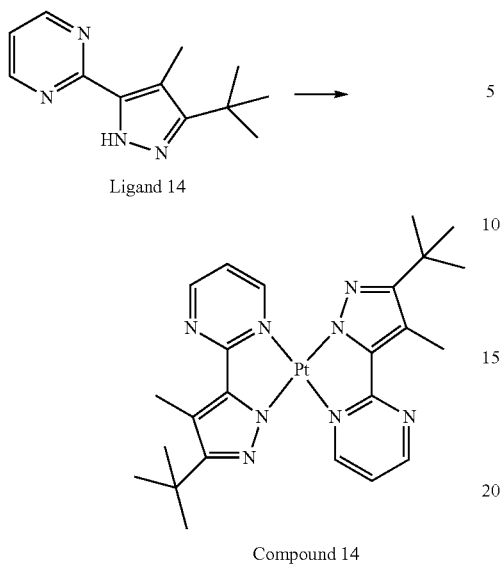

Ligand 14

Compound 14

Compound 14 (Yield 13%) was synthesized in the same manner as described in Synthesis Example 1, via the synthesis of Intermediate 14(1), ligand 14, and Compound 14 according to Reaction Scheme 14, except that 2,2-dimethyl-3-pentanone, instead of the dimethyl-2-butanone used in the synthesis of Intermediate 2(1), was used. This compound was identified using LC-MS and NMR.

LC-MS m/z=626(M+H)$^+$ $^1$H NMR(300MHz, CDCl$_3$) δ=9.76 (d, 4H), 8.71(m, 2H), 2.04(s, 6H), 1.28(s, 9H)

Synthesis Example 15

Synthesis of Compound 15

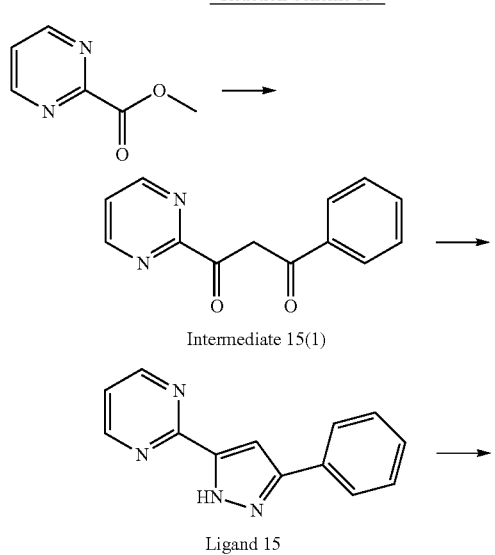

Ligand 15

Compound 15

Compound 15 (Yield 57%) was synthesized in the same manner as described in Synthesis Example 1, via the synthesis of Intermediate 15(1), ligand 15, and Compound 15 according to Reaction Scheme 15, except that acetophenone, instead of the dimethyl-2-butanone used in the synthesis of Intermediate 2(1), was used. This compound was identified using LC-MS and NMR.

LC-MS m/z=638(M+H)$^+$ $^1$H NMR(300MHz, CDCl$_3$) δ=9.82 (d, 4H), 8.53(m, 2H), 7.48-7.22(m, 10H), 6.76(s, 2H)

Synthesis Example 16

Synthesis of Compound 16

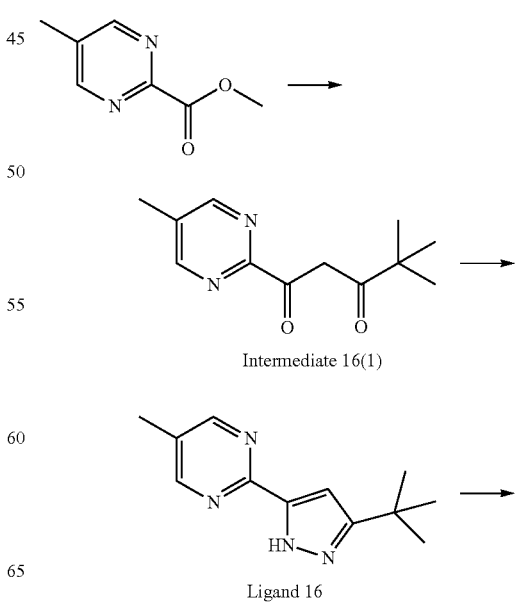

Ligand 16

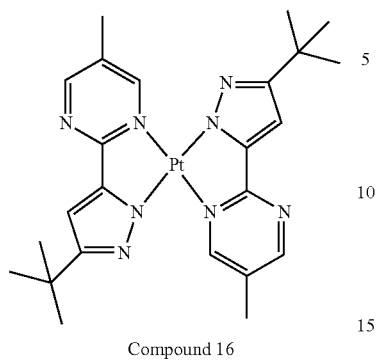

Compound 16

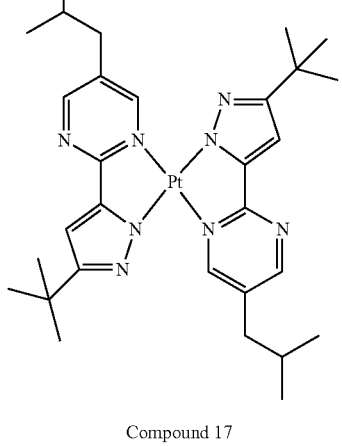

Compound 17

Compound 16 (Yield 16%) was synthesized in the same manner as described in Synthesis Example 1, via the synthesis of Intermediate 16(1), ligand 16, and Compound 16 according to Reaction Scheme 16, except that methyl 5-methylpyrimidine-2-carboxylate, instead of the pyrimidine-2-carboxylic acid methyl ester used in the synthesis of Intermediate 2(1), was used. This compound was identified using LC-MS and NMR.

LC-MS m/z=626(M+H)$^+$ $^1$H NMR(300MHz, CDCl$_3$) δ=9.63 (s, 4H), 6.88(s, 2H), 2.27(s, 6H), 1.28(s, 18H)

Compound 17 (Yield 15%) was synthesized in the same manner as described in Synthesis Example 1, via the synthesis of Intermediate 17(1), ligand 17, and Compound 17 according to Reaction Scheme 17, except that 5-Isobutyl-pyrimidine-2-carboxylic acid methyl ester, instead of pyrimidine-2-carboxylic acid methyl ester, was used. This compound was identified using LC-MS and NMR.

LC-MS m/z=710(M+H)$^+$ $^1$H NMR(300MHz, CDCl$_3$) δ=9.59 (s, 4H), 6.78(s, 2H), 2.43(d, 4H), 2.26-2.23(m, 2H), 1.29(s, 18H), 1.05(s, 12H)

Synthesis Example 17

Synthesis of Compound 17

Synthesis Example 18

Synthesis of Compound 18

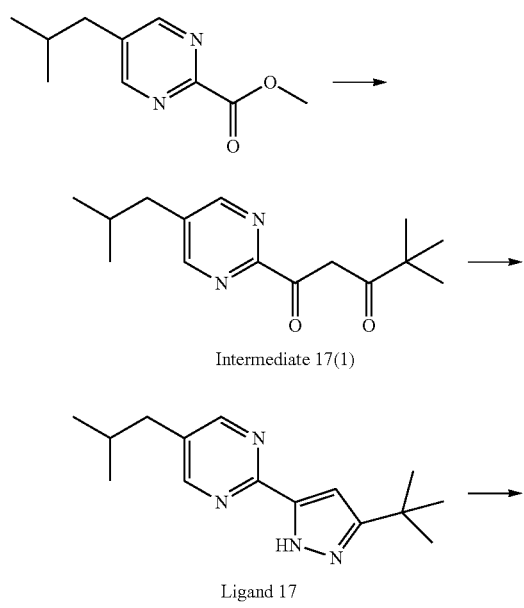

<Reaction Scheme 17>

Intermediate 17(1)

Ligand 17

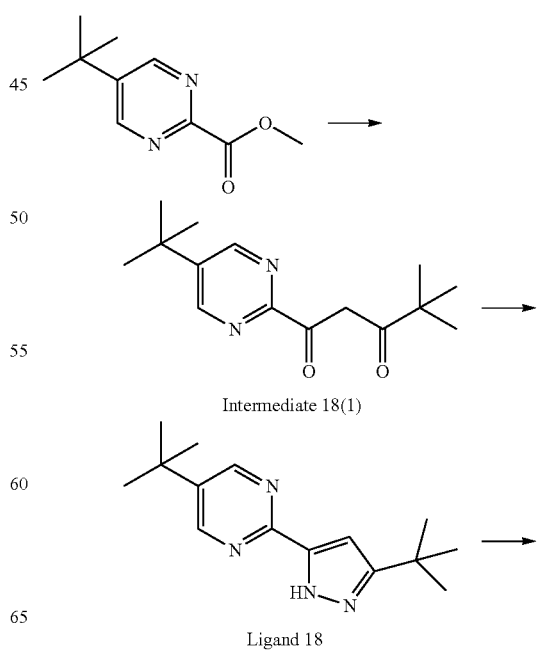

<Reaction Scheme 18>

Intermediate 18(1)

Ligand 18

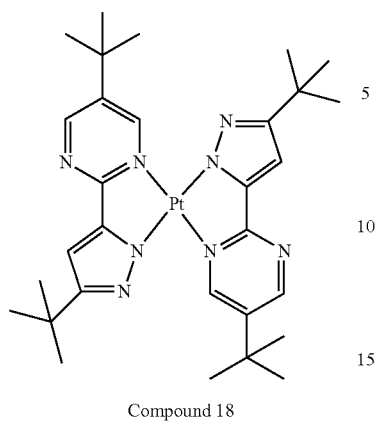

Compound 18

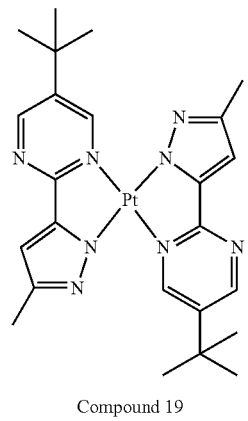

Compound 19

Compound 18 (Yield 10%) was synthesized in the same manner as described in Synthesis Example 1, via the synthesis of Intermediate 18(1), ligand 18, and Compound 18 according to Reaction Scheme 18, except that 5-Isobutyl-pyrimidine-2-carboxylic acid methyl ester, instead of the pyrimidine-2-carboxylic acid methyl ester used in the synthesis of Intermediate 2(1), was used. This compound was identified using LC-MS and NMR.

LC-MS m/z=710(M+H)$^+$ $^1$H NMR(300MHz, CDCl$_3$) δ=9.55 (s, 4H), 6.82(s, 2H), 1.35(s, 18H), 1.33 (s, 18H)

Synthesis Example 19

Synthesis of Compound 19

Compound 19 (Yield 53%) was synthesized in the same manner as described in Synthesis Example 18, via the synthesis of Intermediate 19(1), ligand 19, and Compound 19 according to Reaction Scheme 19, except that acetone, instead of the dimethyl-2-butanone used in the synthesis of Intermediate 18(1), was used. This compound was identified using LC-MS and NMR.

LC-MS m/z=626(M+H)$^+$ $^1$H NMR(300MHz, CDCl$_3$) δ=9.51 (s, 4H), 6.76(s, 2H), 2.82(s, 6H), 1.32 (s, 18H)

Synthesis Example 20

Synthesis of Compound 20

<Reaction Scheme 19>

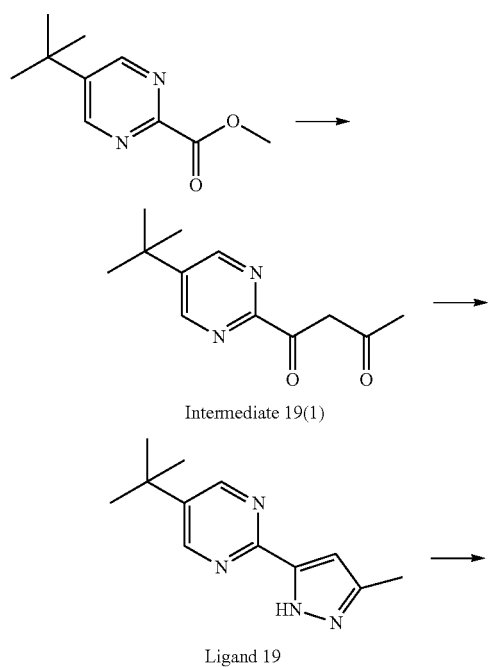

Intermediate 19(1)

Ligand 19

<Reaction Scheme 20>

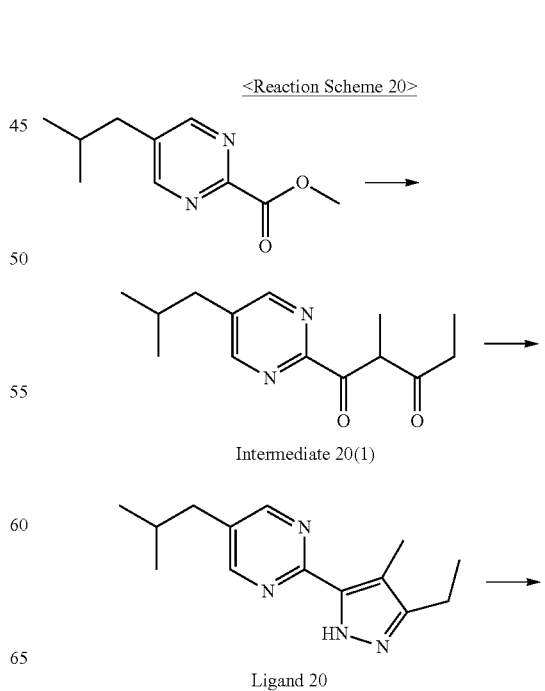

Intermediate 20(1)

Ligand 20

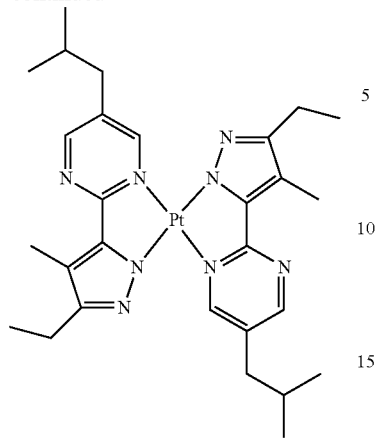

Compound 20

Compound 20 (Yield 8%) was synthesized in the same manner as described in Synthesis Example 17, via the synthesis of Intermediate 20(1), ligand 20, and Compound 20 according to Reaction Scheme 17, except that 3-pentanone, instead of the dimethyl-2-butanone used in the synthesis of Intermediate 17(1), was used. This compound was identified using LC-MS and NMR.

LC-MS m/z=682(M+H)+

$^{1}$H NMR(300MHz, CDCl$_{3}$) δ=9.39 (s, 2H), 2.48(q, 4H), 2.45(d, 4H), 2.22-2.21(m, 2H), 2.06(s, 6H), 1.25(t, 6H), 1.03(t, 12H)

Synthesis Example 21

Synthesis of Compound 21

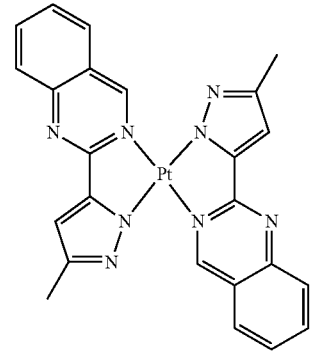

Compound 21

Compound 21 (Yield 8%) was synthesized in the same manner as described in Synthesis Example 8, via the synthesis of Intermediate 21(1), ligand 21, and Compound 21 according to Reaction Scheme 21, except that quinazoline-2-carboxylic acid methyl ester, instead of the pyrimidine-2-carboxylic acid methyl ester used in the synthesis of Intermediate 2(1), was used. This compound was identified using LC-MS and NMR.

LC-MS m/z=614(M+H)+

$^{1}$H NMR(300MHz, CDCl$_{3}$) δ=9.47 (s, 2H), 8.01-7.84(m, 6H), 7.60-7.58(m, 2H), 6.88(s, 2H), 2.81(s, 6H)

Synthesis Example 22

Synthesis of Compound 22

<Reaction Scheme 21>

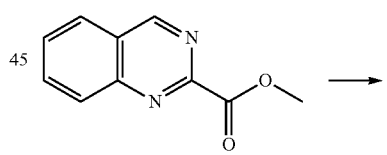

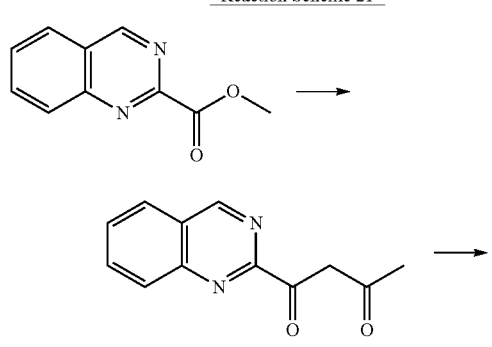

Intermediate 21(1)

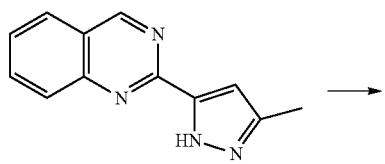

Ligand 21

<Reaction Scheme 22>

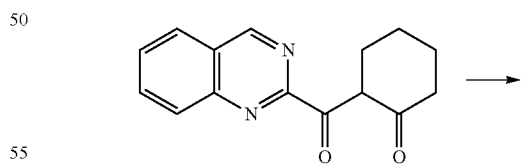

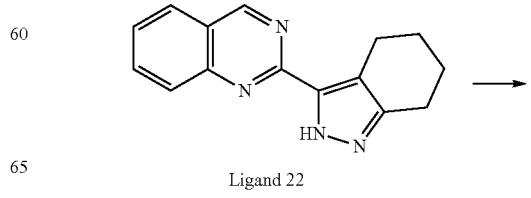

Intermediate 22(1)

Ligand 22

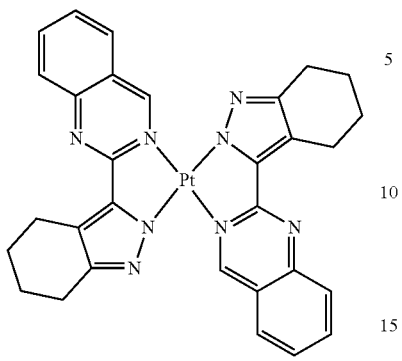

Compound 22

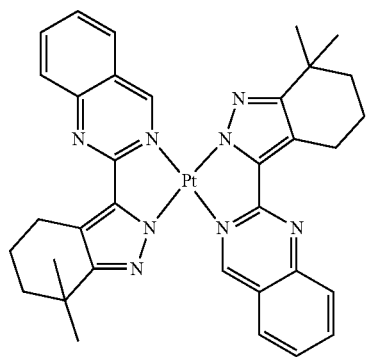

Comopund 23

Compound 22 (Yield 21%) was synthesized in the same manner as described in Synthesis Example 9, via the synthesis of Intermediate 22(1), ligand 22, and Compound 22 according to Reaction Scheme 22, except that methyl quinazoline-2-carboxylate, instead of the pyrimidine-2-carboxylic acid methyl ester used in the synthesis of Intermediate 22(1), was used. This compound was identified using LC-MS and NMR.

LC-MS m/z=694(M+H)$^+$ $^1$H NMR(300MHz, CDCl$_3$) δ=9.82 (s, 2H), 8.01-7.58(m, 8H), 2.52-2.48 (m, 8H), 1.68-1.64 (m, 8H)

Compound 23 (Yield 21%) was synthesized in the same manner as described in Synthesis Example 10, via the synthesis of Intermediate 23(1), ligand 23, and Compound 23 according to Reaction Scheme 23, except that methyl quinazoline-2-carboxylate, instead of the pyrimidine-2-carboxylic acid methyl ester used in the synthesis of Intermediate 23(1), was used. This compound was identified using LC-MS and NMR.

LC-MS m/z=750(M+H)$^+$ $^1$H NMR(300MHz, CDCl$_3$) δ=9.78 (s, 2H), 8.06-7.66(m, 8H), 2.48-2.42 (m, 4H), 1.71-1.66 (m, 8H), 1.42 (s, 12H)

Synthesis Example 23

Synthesis of Compound 23

<Reaction Scheme 23>

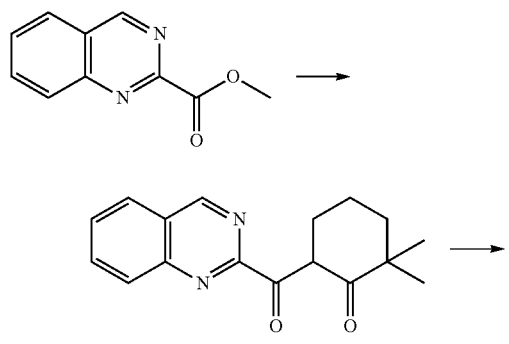

Intermediate 23(1)

Ligand 23

Synthesis Example 24

Synthesis of Compound 24

<Reaction Scheme 24>

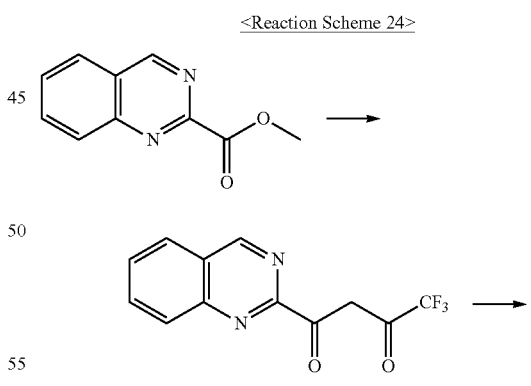

Intermediate 24(1)

Ligand 24

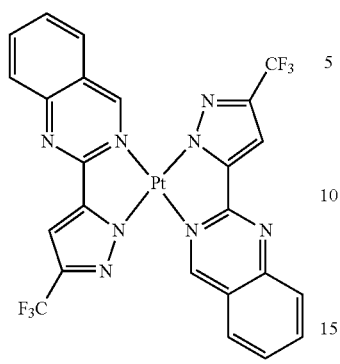

Compound 24

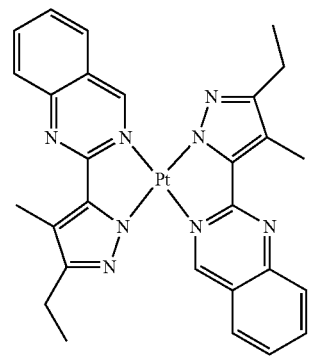

Compound 25

Compound 24 (Yield 21%) was synthesized in the same manner as described in Synthesis Example 22, via the synthesis of Intermediate 24(1), ligand 24, and Compound 24 according to Reaction Scheme 24, except that 1,1,1-trifluoro-propan-2-one, instead of the cyclohexanone used in the synthesis of Intermediate 24(1), was used. This compound was identified using LC-MS and NMR.

LC-MS m/z=722(M+H)$^+$ $^1$H NMR(300MHz, CDCl$_3$) δ=9.72 (s, 2H), 8.03-7.66(m, 8H), 6.87 (s, 2H)

Synthesis Example 25

Synthesis of Compound 25

Compound 25 (Yield 21%) was synthesized in the same manner as described in Synthesis Example 21, via the synthesis of Intermediate 25(1), ligand 25, and Compound 25 according to Reaction Scheme 25, except that 3-pentanone, instead of the acetone used in the synthesis of Intermediate 25(1), was used. This compound was identified using LC-MS and NMR.

LC-MS m/z=670(M+H)$^+$ $^1$H NMR(300MHz, CDCl$_3$) δ=9.81 (s, 2H), 8.11-7.76(m, 8H), 2.53 (q, 4H), 2.09 (s, 6H), 1.27 (s, 6H)

Synthesis Example 26

Synthesis of Compound 26

<Reaction Scheme 25>

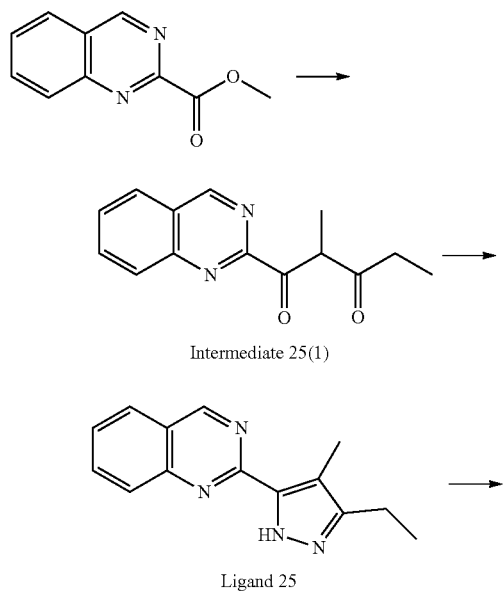

Intermediate 25(1)

Ligand 25

<Reaction Scheme 26>

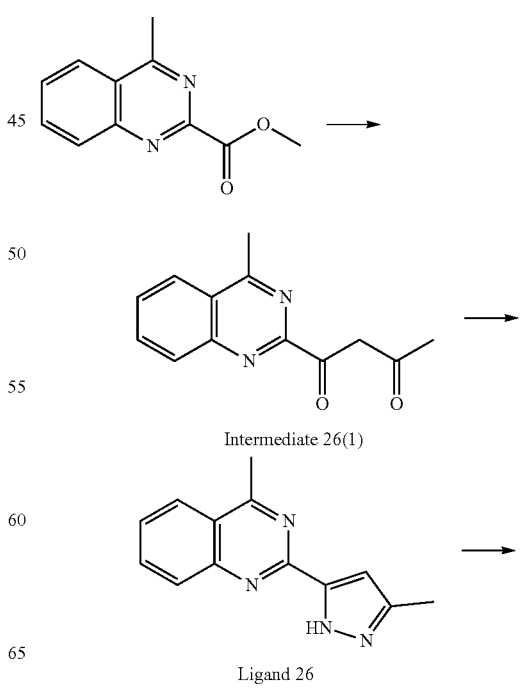

Intermediate 26(1)

Ligand 26

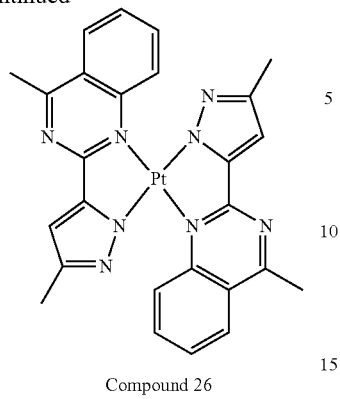

Compound 26

Compound 26 (Yield 11%) was synthesized in the same manner as described in Synthesis Example 8, via the synthesis of Intermediate 26(1), ligand 26, and Compound 26 according to Reaction Scheme 26, except that 4-methyl-quinazoline-2-carboxylic acid methyl) ester, instead of the pyrimidine-2-carboxylic acid methyl ester used in the synthesis of Intermediate 8(1), was used. This compound was identified using LC-MS and NMR.

LC-MS m/z=642(M+H)$^+$ $^1$H NMR(300MHz, CDCl$_3$) δ=8.68 (s, 2H), 8.06-8.03 (m, 4H), 7.68-7.62 (m, 2H), 6.79 (s, 2H), 2.81 (s, 6H), 2.28 (s, 6H)

Synthesis Example 27

Synthesis of Compound 27

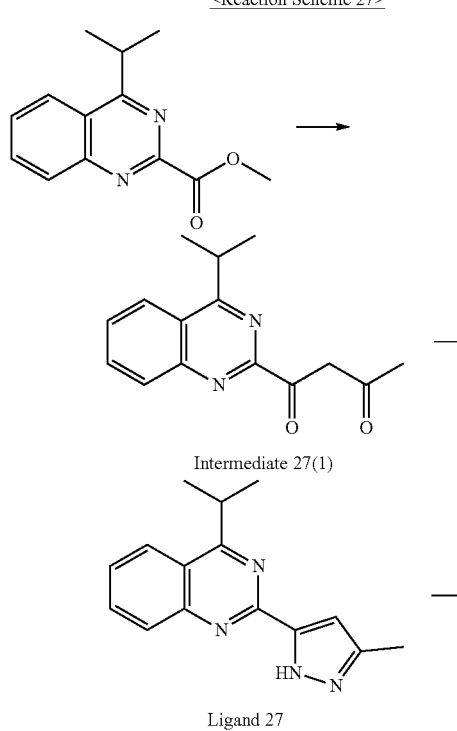

<Reaction Scheme 27>

Intermediate 27(1)

Ligand 27

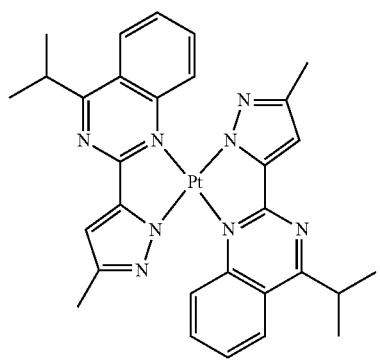

Compound 27

Compound 27 (Yield 6%) was synthesized in the same manner as described in Synthesis Example 26, via the synthesis of Intermediate 27(1), ligand 27, and Compound 27 according to Reaction Scheme 27, except that 4-isopropyl-quinazoline-2-carboxylic acid methyl ester, instead of the 4-methyl-quinazoline-2-carboxylic acid methyl ester used in the synthesis of Intermediate 26(1), was used. This compound was identified using LC-MS and NMR.

LC-MS m/z=698(M+H)$^+$ $^1$H NMR(300MHz, CDCl$_3$) δ=8.71 (s, 2H), 8.09-8.05 (m, 4H), 7.72-7.68 (m, 2H), 6.76 (s, 2H), 3.14-3.12 (m, 2H), 2.78 (s, 6H), 1.21 (s, 12H)

Synthesis Example 28

Synthesis of Compound 28

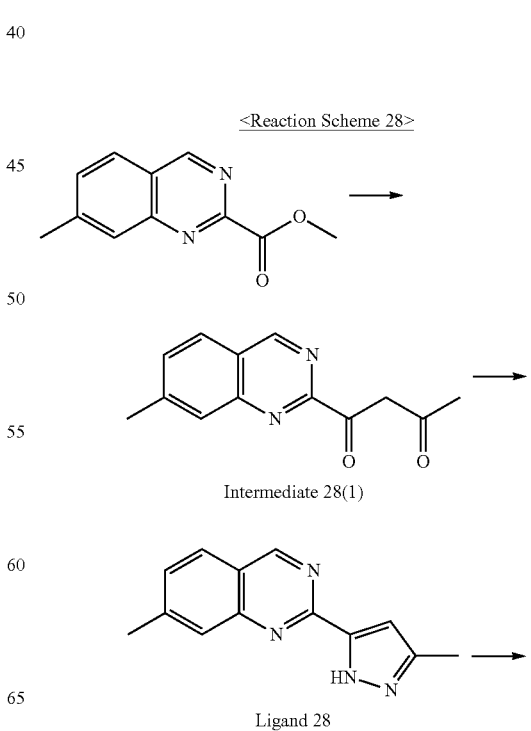

<Reaction Scheme 28>

Intermediate 28(1)

Ligand 28

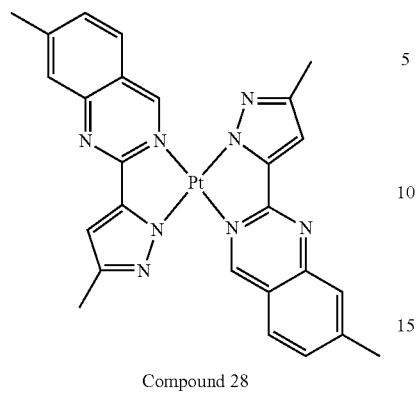

Compound 28

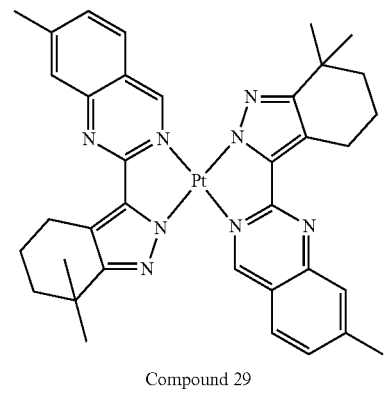

Compound 29

Compound 28 (Yield 17%) was synthesized in the same manner as described in Synthesis Example 26, via the synthesis of Intermediate 28(1), ligand 28, and Compound 28 according to Reaction Scheme 28, except that 7-methyl-quinazoline-2-carboxylic acid methyl ester, instead of the 4-methyl-quinazoline-2-carboxylic acid methyl ester used in the synthesis of Intermediate 26(1), was used. This compound was identified using LC-MS and NMR.

LC-MS m/z=642(M+H)$^+$ $^1$H NMR(300MHz, CDCl$_3$) δ=9.42 (s, 2H), 7.86-7.77 (m, 4H), 7.49-7.45(m, 2H), 6.86 (s, 2H), 2.77 (s, 6H), 2.26 (s, 6H)

Compound 29 (Yield 22%) was synthesized in the same manner as described in Synthesis Example 28, via the synthesis of Intermediate 29(1), ligand 29, and Compound 29 according to Reaction Scheme 29, except that 2,2-dimethyl-cyclohexanone, instead of the acetone used in the synthesis of Intermediate 28(1), was used. This compound was identified using LC-MS and NMR.

LC-MS m/z=778(M+H)$^+$ $^1$H NMR(300MHz, CDCl$_3$) δ=9.39 (s, 2H), 7.81-7.69 (m, 4H), 7.46-7.43(m, 2H), 2.56-2.54 (m, 4H), 2.31 (s, 6H), 1.65-1.52 (m, 8H), 1.29 (s, 12H)

Synthesis Example 29

Synthesis of Compound 29

Synthesis Example 30

Synthesis of Compound 30

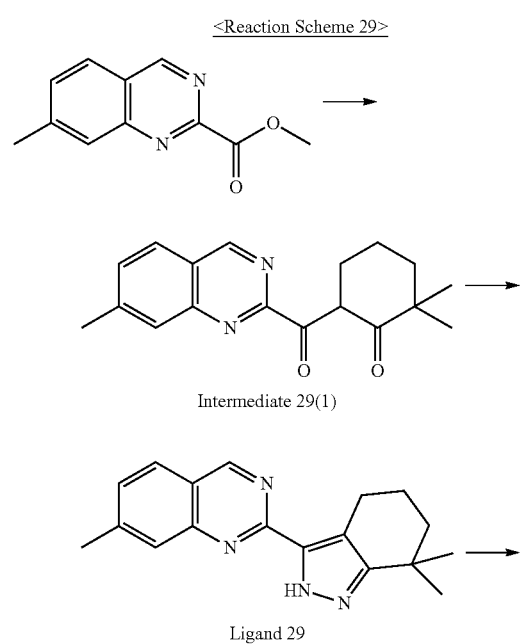

<Reaction Scheme 29>

Intermediate 29(1)

Ligand 29

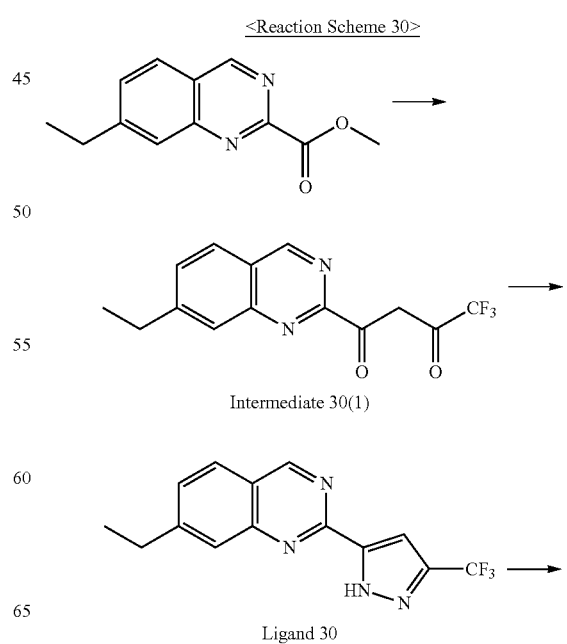

<Reaction Scheme 30>

Intermediate 30(1)

Ligand 30

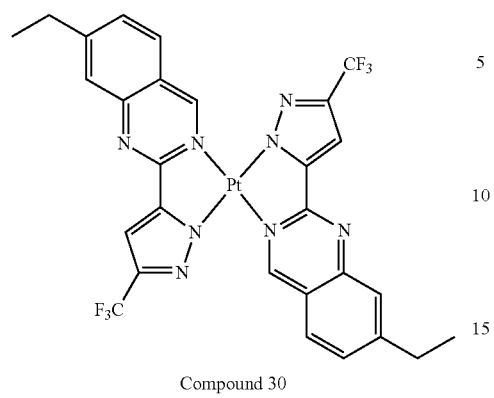

Compound 30

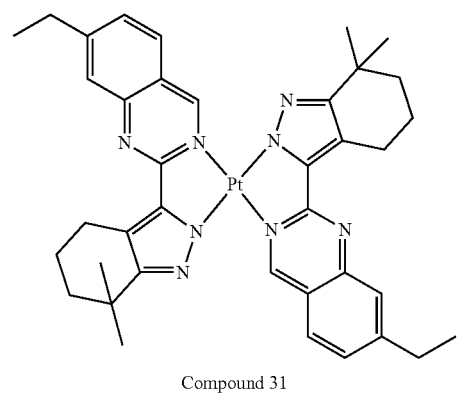

Compound 31

Compound 30 (Yield 19%) was synthesized in the same manner as described in Synthesis Example 24, via the synthesis of Intermediate 30(1), ligand 30, and Compound 30 according to Reaction Scheme 30, except that 7-ethyl-quinazoline-2-carboxylic acid methyl ester, instead of the methyl quinazoline-2-carboxylate used in the synthesis of Intermediate 24(1), was used. This compound was identified using LC-MS and NMR.

LC-MS m/z=778(M+H)$^+$ $^1$H NMR(300MHz, CDCl$_3$) δ=9.36 (s, 2H), 7.85-7.74 (m, 4H), 7.32-7.28(m, 2H), 6.76 (s, 2H), 2.62 (q, 4H), 1.21 (t, 3H)

Compound 31 (Yield 19%) was synthesized in the same manner as described in Synthesis Example 30, via the synthesis of Intermediate 31(1), ligand 31, and Compound 31 according to Reaction Scheme 31, except that 2,2-dimethyl-cyclohexanone, instead of the 1,1,1-trifluoro-propan-2-one used in the synthesis of Intermediate 30(1), was used. This compound was identified using LC-MS and NMR.

LC-MS m/z=806(M+H)$^+$ $^1$H NMR(300MHz, CDCl$_3$) δ=9.42 (s, 2H), 7.79-7.72 (m, 4H), 7.42-7.21(m, 2H), 2.61-2.59 (br m, 8H), 1.62-1.54 (m, 8H), 1.41 (s, 12H), 1.27 (t, 6H)

Synthesis Example 31

Synthesis of Compound 31

Synthesis Example 32

Synthesis of Compound 32

<Reaction Scheme 31>

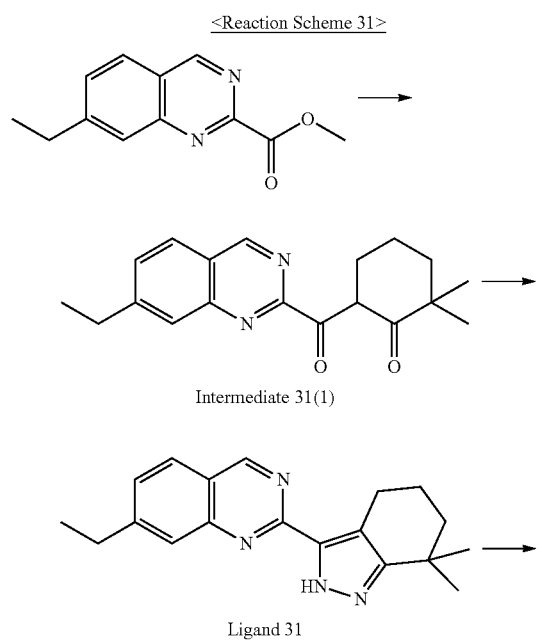

<Reaction Scheme 32>

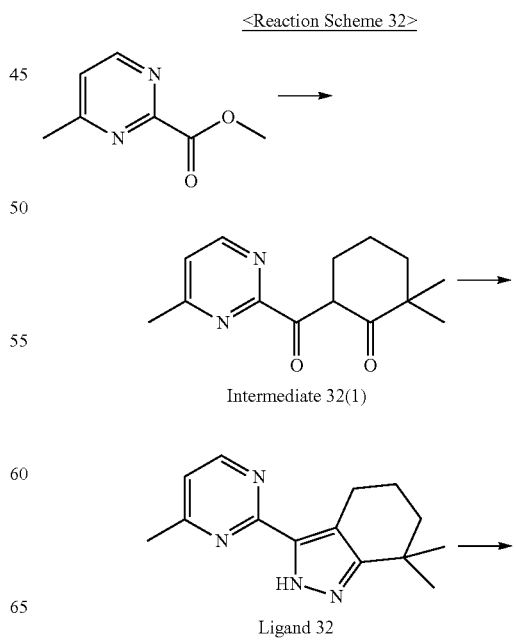

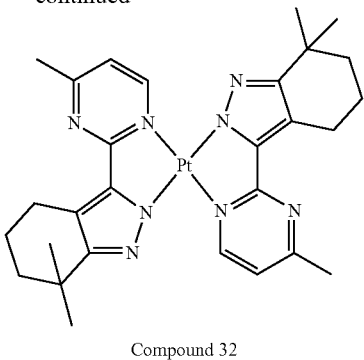

Compound 32

Compound 32 (Yield 22%) was synthesized in the same manner as described in Synthesis Example 10, via the synthesis of Intermediate 32(1), ligand 32, and Compound 32 according to Reaction Scheme 32, except that 4-methyl-pyrimidine-2-carboxylic acid methyl ester, instead of the pyrimidine-2-carboxylic methyl ester used in the synthesis of Intermediate 32(1), was used. This compound was identified using LC-MS and NMR.

LC-MS m/z=678(M+H)$^+$ $^1$H NMR(300MHz, CDCl$_3$) δ=8.85 (s, 2H), 7.16 (s, 2H), 2.52-2.50 (m, 4H), 2.31 (s, 6H), 1.62-1.53 (m, 8H), 1.29 (s, 12H)

Synthesis Example 33

Synthesis of Compound 33

<Reaction Scheme 33>

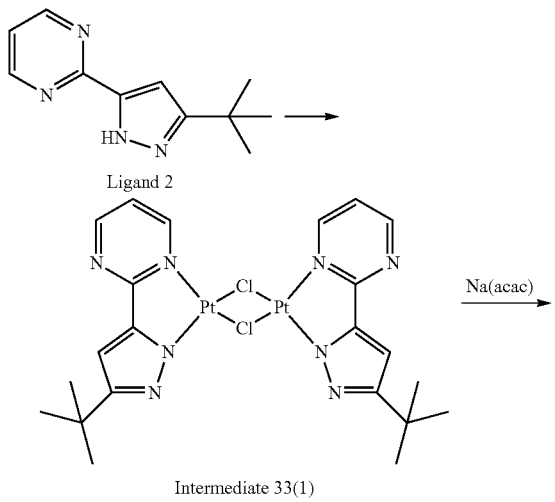

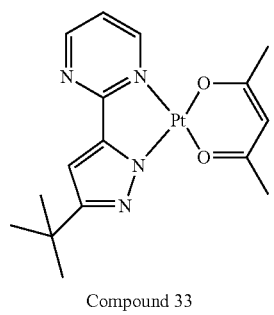

Compound 33

Synthesis of Intermediate 33(1)

About 1 g (4.7 mmol) of ligand 2 from Synthesis Example 1 and 2.0 g (4.7 mmol) of K$_2$PtCl$_4$ were dissolved in a mixed solvent of 30 ml of ethanol and 10 ml of distilled water, followed by an addition of 5 ml of 4N HCl, and heating under reflux. After 18 hours of reflux, the reaction product was cooled to room temperature, filtered, and dried to obtain Intermediate 33(1).

Synthesis of Compound 33

NaH (4.7 mmol) was dissolved in 30 ml of anhydrous tetrahydrofuran to obtain a solution, and Intermediate 33(1) (4.7 mmol) mixed with 10 ml of tetrahydrofuran was slowly added to the solution at about 0° C. After 5 minutes, Na(acac) was added to the mixture, which was then heated under reflux for about 18 hours. The resulting solid was filtered to obtain Compound 33 (Yield 18%). This compound was identified using LC-MS and NMR.

LC-MS m/z=498(M+H)$^+$ $^1$H NMR(300MHz, CDCl$_3$) δ=9.68 (d, 2H), 8.61-8.60 (m, 1H), 6.88 (s, 2H), 5.35 (s, 1H), 3.52-3.50(m, 1H), 1.38(s, 9H), 1.18(s, 6H)

Synthesis Example 34

Synthesis of Compound 34

Compound 34 (Yield 11%) was synthesized in the same manner as described in Synthesis Example 33, except that ligand 10 of Synthesis Example 10, instead of ligand 2, was used.

LC-MS m/z=524(M+H)$^+$ $^1$H NMR(300MHz, CDCl$_3$) δ=9.81 (d, 2H), 8.71-8.69 (m, 1H), 5.31 (br s, 1H), 3.52-3.50(m, 1H), 2.75-2.73(m, 2H), 1.79-1.76(m, 2H), 1.54-1.52(m, 2H), 1.40(s, 6H), 1.20(s, 6H)

Synthesis Example 35

Synthesis of Compound 35

Compound 35 (Yield 8%) was synthesized in the same manner as described in the method of Synthesis Example 33, except that ligand 3 of Synthesis Example 3, instead of ligand 2, was used.

LC-MS m/z=510(M+H)$^+$ $^1$H NMR(300MHz, CDCl$_3$) δ=9.74(d, 2H), 8.65-8.63(m, 1H), 6.36(s, 1H), 5.33 (br s, 1H), 3.53-3.51(m, 1H), 1.18(s, 6H)

Synthesis Example 36

Synthesis of Compound 36

Compound 36 (Yield 13%) was synthesized in the same manner as described in Synthesis Example 33, except that ligand '4 of Synthesis Example 14, instead of ligand 2, was used.

LC-MS m/z=512(M+H)$^+$ $^1$H NMR(300MHz, CDCl$_3$) δ=9.87 (d, 2H), 8.71-8.70 (m, 1H), 5.31 (br s, 1H), 3.52-3.50(m, 1H), 2.75-2.73(m, 2H), 2.10(s, 3H), 1.35(s, 9H), 1.18(s, 6H)

Synthesis Example 37

Synthesis of Compound 37

Synthesis of ligand 7

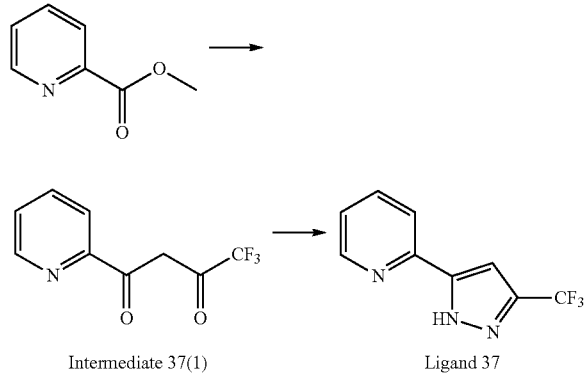

<Reaction Scheme 37-1>

Intermediate 37(1) → Ligand 37

Ligand 37 (Yield 63%) was synthesized in the same manner as described in the method of synthesizing ligand 2 of Synthesis Example 1, via the synthesis of Intermediate 37(1) and ligand 37 according to Reaction Scheme 37-1, except that methyl picolinate, instead of the pyrimidine-2-carboxylic acid methyl ester used in the synthesis of Intermediate 2(1), was used. This compound was identified using LC-MS.

LC-MS m/z=214(M+H)$^\pm$

Synthesis of Compound 37

<Reaction Scheme 37-2>

Ligand 3

Intermediate 3(5)  + Ligand 37 →

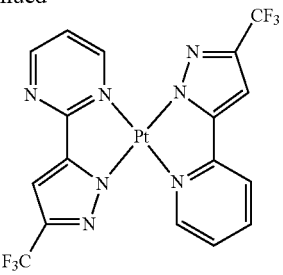

Compound 37

A quantity of 1.5 g (7.1 mmol) of ligand 3 from Synthesis Example 3, and 3.0 g (7.1 mmol) of $K_2PtCl_4$ were dissolved in a mixed solvent of 45 ml of ethanol and 20 ml of distilled water, and 8 ml of 4N HCl was added to the mixture, which was then heated under reflux. After 18 hours of reflux, the reaction mixture was cooled to room temperature. The resulting solid compound was filtered and dried to obtain Intermediate 3(5). NaH (7.0 mmol) was dissolved in 50 ml of anhydrous tetrahydrofuran in another reaction vessel, and ligand 37 (7.0 mmol) of Synthesis Example 17 mixed with 20 ml of tetrahydrofuran was slowly added thereto at about 0° C. After 30 minutes, Intermediate 3(5) was added to the reaction product, which was then heated under reflux for about 24 hours. The resulting solid product was filtered to obtain Compound 37 (Yield 21%). This compound was identified using LC-MS and NMR.

LC-MS m/z=621(M+H)$^+$ $^1$H NMR(300MHz, CDCl$_3$) δ=9.41 (s, 2H), 9.11 (s, 1H), 7.82-7.71 (m, 2H), 7.34-7.32 (m, 2H), 6.84 (s, 1H), 6.79 (s, 1H)

Synthesis Example 38

Synthesis of Compound 38

Synthesis of Ligand 38

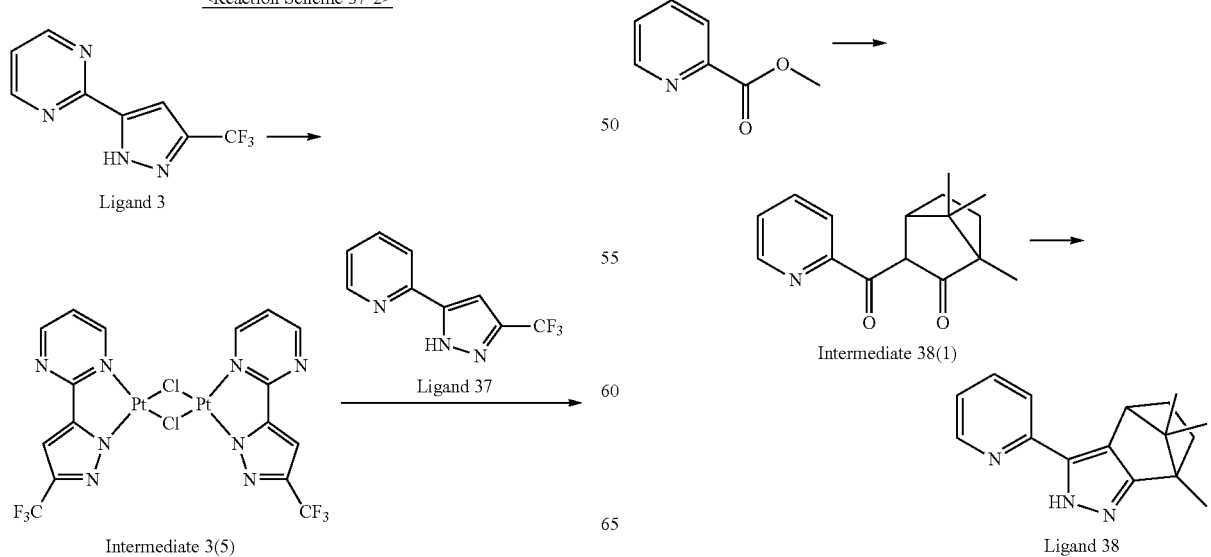

<Reaction Scheme 38>

Intermediate 38(1) → Ligand 38

Ligand 38 (Yield 55%) was synthesized in the same manner as described in the method of synthesizing ligand 2 of Synthesis Example 1, via the synthesis of Intermediate 38(1) and ligand 38 according to Reaction Scheme 38, except that methyl picolinate, instead of pyrimidine-2-carboxylic acid methyl ester, and camphor, instead of the dimethyl-2-butanone used in the synthesis of Intermediate 2(1), was used.

This compound was identified using LC-MS and NMR.
LC-MS m/z=254(M+H)$^+$

Synthesis of Compound 38

Compound 38 (Yield 15%) was synthesized in the same manner as described in the method of synthesizing Compound 37 in Synthesis Example 37, except that ligand 38, instead of ligand 37, was used. This compound was identified using LC-MS and NMR.
LC-MS m/z=661(M+H)$^+$
$^1$H NMR (300 MHz, CDCl$_3$) δ=9.61 (d, 2H), 8.72-7.70 (m, 1H), 7.81-7.72 (m, 2H), 7.34-7.32 (m, 2H), 6.51 (s, 1H), 2.75-2.72 (m, 1H), 1.80-1.70 (m, 4H), 1.42 (s, 3H), 1.09 (s, 6H)

Synthesis Example 39

Synthesis of Compound 39

Synthesis of Ligand 39

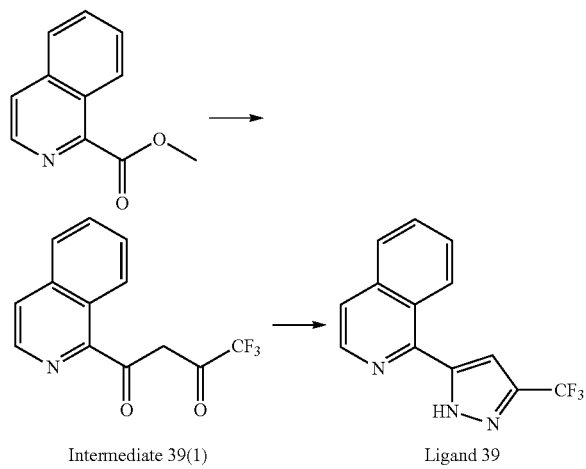

<Reaction Scheme 39>

Intermediate 39(1)    Ligand 39

Ligand 39 (Yield 50%) was synthesized in the same manner as described in the method of synthesizing ligand 2 of Synthesis Example 1, via the synthesis of Intermediate 39(1) and ligand 39 according to Reaction Scheme 39, except that methyl isoquinoline-1-carboxylate, instead of pyrimidine-2-carboxylic acid methyl ester, and 1,1,1-trifluoropropan-2-one, instead of the dimethyl-2-butanone used in the synthesis of Intermediate 2(1), was used. This compound was identified using LC-MS and NMR.
LC-MS m/z=264(M+H)$^+$ Synthesis of Compound 39

Compound 37 (Yield 10%) was synthesized in the same manner as described in the method of synthesizing Compound 37 in Synthesis Example 37, except that ligand 39, instead of ligand 37, was used. This compound was identified using LC-MS and NMR.
LC-MS m/z=671(M+H)$^+$
$^1$H NMR(300MHz, CDCl$_3$) δ=9.32 (d, 2H), 8.58-8.56 (m, 1H), 7.91-7.32 (m, 6H), 6.58 (s, 1H)

Synthesis Example 40

Synthesis of Compound 40

Compound 40 (Yield 16%) was synthesized in the same manner as described in the method of synthesizing Compound 37 in Synthesis Example 37, except that 2-phenylpyridine, instead of ligand 37, was used. This compound was identified using LC-MS and NMR.
LC-MS m/z=563(M+H)$^+$
$^1$H NMR(300MHz, CDCl$_3$) δ=9.56 (d, 2H), 8.46-8.43 (m, 1H), 8.01-6.7.36 (m, 8H), 6.55 (s, 1H)

Synthesis Example 41

Synthesis of Compound 41

Synthesis of Ligand 41

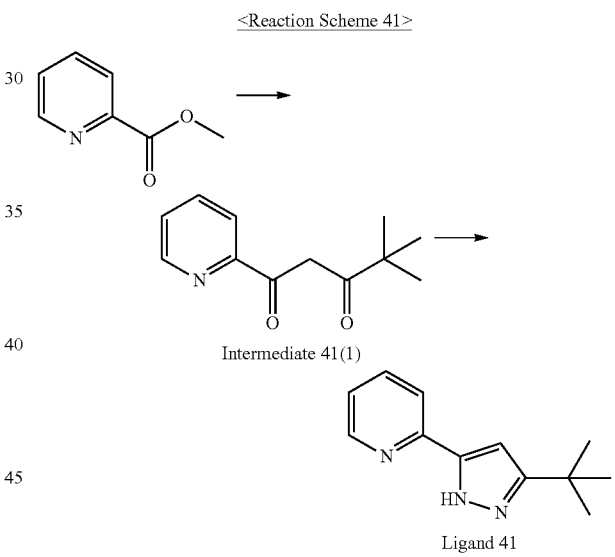

<Reaction Scheme 41>

Intermediate 41(1)

Ligand 41

Ligand 41 (Yield 60%) was synthesized in the same manner as described in the method of synthesizing ligand 2 of Synthesis Example 1, via the synthesis of Intermediate 41(1) and ligand 41 according to Reaction Scheme 41, except that methyl picolinate, instead of the pyrimidine-2-carboxylic acid methyl ester used in the synthesis of Intermediate 2(1), was used. This compound was identified using LC-MS and NMR.
LC-MS m/z=202(M+H)$^+$ Synthesis of Compound 41

Compound 41 (Yield 15%) was synthesized in the same manner as described in the method of synthesizing Compound 37 in Synthesis Example 37, except that ligand 41, instead of ligand 37, was used. This compound was identified using LC-MS and NMR.
LC-MS m/z=609(M+H)$^+$ $^1$H NMR(300MHz, CDCl$_3$) δ=9.33 (d, 2H), 8.52-8.50 (m, 1H), 7.81-7.34 (m, 4H), 6.48 (s, 1H), 6.45 (s, 1H), 1.32 (s, 9H)

Synthesis Example 42

Synthesis of Compound 42

Compound 42 was synthesized according to Reaction Scheme 42 below:

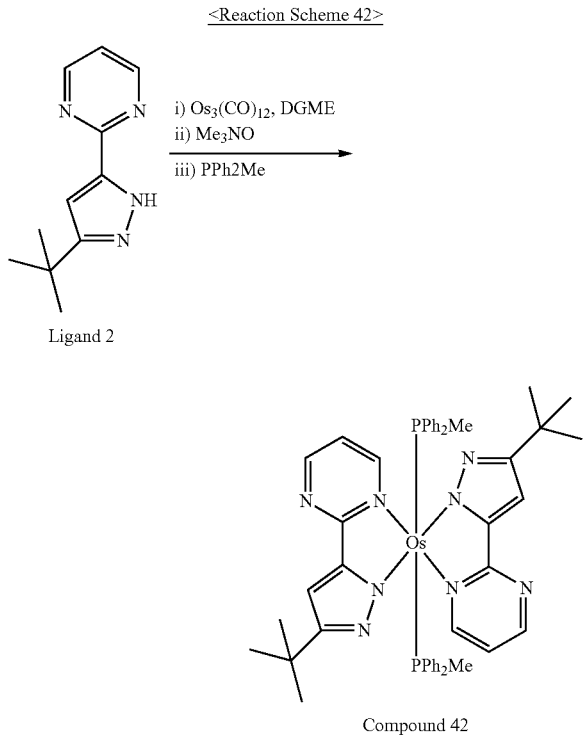

Ligand 2 (6.0 mmol) was dissolved in 40 ml of diethylene glycol monoethyl ether, and 0.9 g (1.0 mmol) of Os$_3$(CO)$_{12}$ was added to the solution and stirred at about 180° C. for 24 hours. After the temperature was lowered to about 140° C., 0.4 g (5.0 mmol) of trimethyl amine N-oxide was added to the reaction product, which was then stirred at about 180° C. for about 5 minutes. After 5 minutes, 5.0 mmol of diphenyl (methyl)phosphine (PPh$_2$Me) was added thereto and stirred for about 24 hours. After completion of the reaction, 80 ml of distilled water was added to the reaction product, which was then extracted with 200 ml of ethyl acetate. The organic layer was collected, dried using anhydrous magnesium sulfate, distilled under reduced pressure, and the resulting product residue was then separated and purified using column chromatography, followed by purification via sublimation to obtain Compound 42 (Yield 7%). This compound was identified using LC-MS and NMR.

LC-MS m/z=1010(M+H)$^+$ $^1$H NMR(300MHz, CDCl$_3$) δ=10.87(d, 4H), 8.36-8.33(m, 2H), 7.23-7.16(d, 4H), 6.96-6.93(m, 8H), 6.46-6.43(m, 6H), 1.37(m, 18H), 0.81(m, 6H), 0.60(m, 6H)

Synthesis Example 43

Synthesis of Compound 43

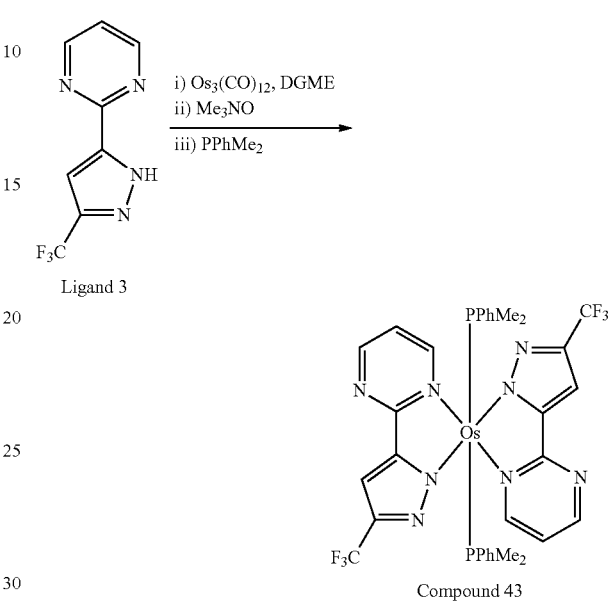

Compound 43 (Yield 10%) was synthesized in the same manner as described in Synthesis Example 42, except that ligand 3, instead of ligand 2, and dimethyl(phenyl)phosphine (PPhMe$_2$), instead of diphenyl(methyl)phosphine (PPh$_2$Me), were used. This compound was identified using LC-MS and NMR.

LC-MS m/z=895(M+H)$^+$ $^1$H NMR(300MHz, CDCl$_3$) δ=11.01(d, 4H), 8.41-8.38(m, 2H), 7.62-7.58 (m, 2H), 7.05-7.00 (d, 2H), 6.92-6.87(m, 8H), 0.81(m, 6H), 0.60(m, 6H)

Synthesis Example 44

Synthesis of Compound 44

Compound 44 was synthesized according to Reaction Scheme 44 below:

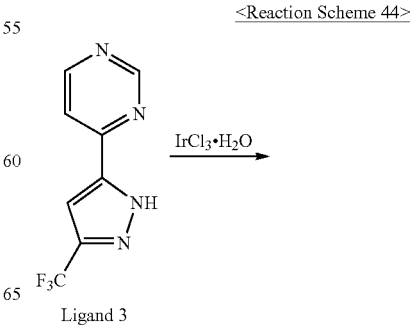

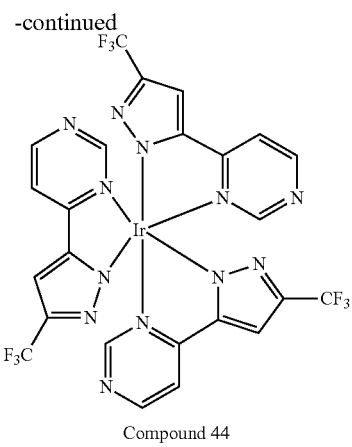

Compound 44

Ligand 3 (1.0 mmol) was dissolved in 30 ml of ethylene glycol, and 0.4 g (0.3 mmol) of IrCl$_3$.3H$_2$O was added to the solution, which was then stirred at about 220° C. for about 24 hours. After completion of the reaction, 50 ml of distilled water was added at room temperature to the reaction product, which was then extracted with 100 ml of methylene chloride. The organic layer was collected, dried using anhydrous magnesium sulfate, distilled under reduced pressure, and the resulting product residue was then separated and purified using column chromatography to obtain Compound 44 (Yield <2%). This compound was identified using LC-MS and NMR.

LC-MS m/z=833(M+H)$^+$

Synthesis Example 45

Synthesis of Compound 45

Compound 45 was synthesized according to Reaction Scheme 45 below:

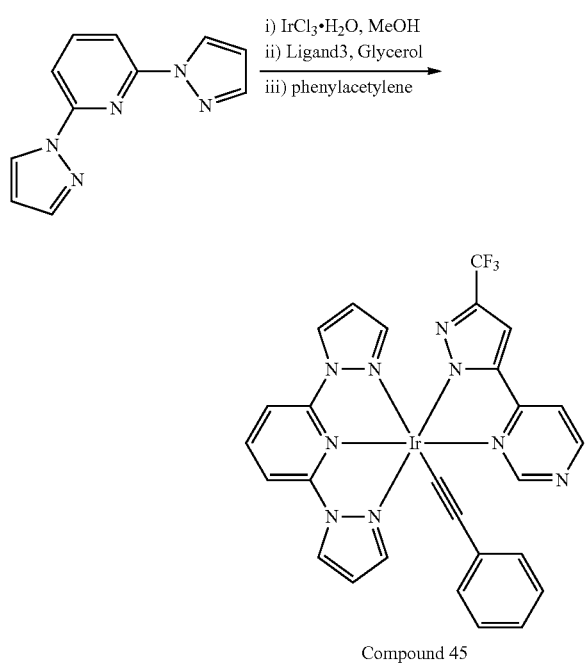

Compound 45

A quantity of 1.5 g (7.1 mmol) of 2,6-di-pyrazole-1-yl-pyridine and 2.6 g (2.0 mmol) of IrCl$_3$.3H$_2$O were dissolved in 60 ml of methanol to obtain a mixture, which was then heated under reflux for about 15 hours. The temperature was then cooled to room temperature, and the resulting solid product was filtered, dried, and then dissolved in 120 ml of glycerol. A quantity of 4.5 g (21.3 mmol) ligand 3 was added to the reaction mixture and reacted for about 3 hours by microwave radiation (300 W). After completion of the reaction, 200 ml of saturated sodium chloride solution was added to the reaction product and stirred. The resulting solid product was filtered, dried, and recrystallized using a mixed solvent of dichloromethane and hexane. The resulting solid compound was dissolved in 80 ml of glycerol, followed by an addition of potassium hydroxide and reaction for about 6 hours by microwave radiation (300 W). After completion of the reaction, 100 ml of saturated sodium chloride solution was added at room temperature to the reaction product, which was then extracted with 300 ml of methylene chloride. The organic layer was collected, dried using anhydrous magnesium sulfate, distilled under reduced pressure, and separated and purified using column chromatography to obtain Compound 45 (Yield 18%). This compound was identified using LC-MS and NMR.

LC-MS m/z=719(M+H)$^+$

Example 1

To manufacture an anode, a glass substrate with deposited ITO/Ag/ITO layers (70/1000/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was deposited to form an HIL having a thickness of 600 Å on the anode, and then 4,4'-bis[N-(1-naphthyl)-N-phenylamino]biphenyl (NPS) was deposited on the HIL to form a HTL having a thickness of about 1000 Å.

CBP (host) and Compound 2 (dopant) were co-deposited in a weight ratio of about 95:5 on the hole transport layer to form an emission layer having a thickness of about 400 Å, followed by depositing BCP on the emission layer to form a hole blocking layer having a thickness of about 50 Å. After deposition of Alq$_3$ on the hole blocking layer to form an electron transport layer having a thickness of about 350 Å, LiF was deposited on the electron transport layer to form an electron injecting layer having a thickness of about 10 Å, followed by depositing Mg and Al in a weight ratio of about 90:10 on the electron injection layer to form a cathode having a thickness of about 120 Å, thereby completing the manufacture of the organic light-emitting device.

Example 2

An organic light-emitting device was manufactured in the same manner as described in Example 1, except that Compound 4, instead of Compound 2, was used to form the EML.

Example 3

An organic light-emitting device was manufactured in the same manner as described in Example 1, except that Compound 5, instead of Compound 2, was used to form the EML.

Example 4

An organic light-emitting device was manufactured in the same manner as described in Example 1, except that Compound 10, instead of Compound 2, was used to form the EML.

Example 5

An organic light-emitting device was manufactured in the same manner as described in Example 1, except that Compound 18, instead of Compound 2, was used to form the EML.

Example 6

An organic light-emitting device was manufactured in the same manner as described in Example 1, except that Compound 20, instead of Compound 2, was used to form the EML.

Example 7

An organic light-emitting device was manufactured in the same manner as described in Example 1, except that Compound 29, instead of Compound 2, was used to form the EML.

Example 8

An organic light-emitting device was manufactured in the same manner as described in Example 1, except that the thickness of the hole transport layer was varied about 1350 Å, and CBP (host) and Compound 15 (dopant) were co-deposited in a weight ratio of about 94:6 on the hole transport layer to form an emission layer having a thickness of about 400 Å.

Example 9

An organic light-emitting device was manufactured in the same manner as described in Example 1, except that Compound 42, instead of Compound 15, was used to form the EML.

Example 10

An organic light-emitting device was manufactured in the same manner as described in Example 1, except that Compound 43, instead of Compound 15, was used to form the EML.

Comparative Example 1

An organic light-emitting device was manufactured in the same manner as described in Example 1, except that Ir(ppy)$_3$, instead of Compound 2, was used to form the EML.

Comparative Example 2

An organic light-emitting device was manufactured in the same manner as described in Example 1, except that Compound A, instead of Compound 2, was used to form the EML.

Comparative Example 3

An organic light-emitting device was manufactured in the same manner as described in Example 1, except that Compound B, instead of Compound 2, was used to form the EML.

Comparative Example 4

An organic light-emitting device was manufactured in the same manner as described in Example 1, except that Compound C, instead of Compound 2, was used to form the EML.

Comparative Example 5

An organic light-emitting device was manufactured in the same manner as described in Example 3, except that PtOEP, instead of Compound 2, was used to form the EML.

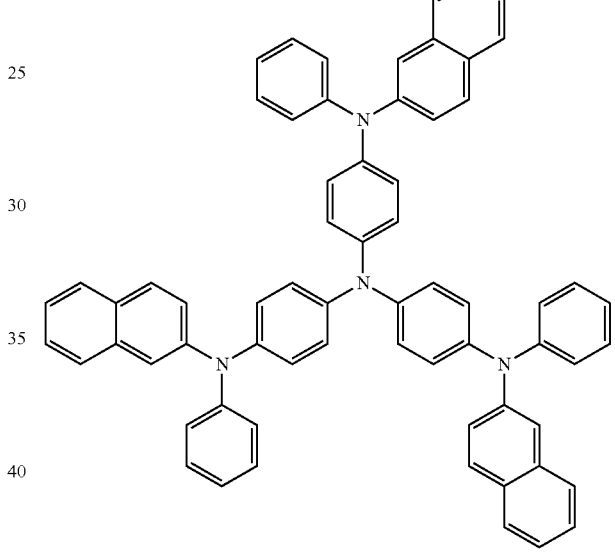

2-TNATA

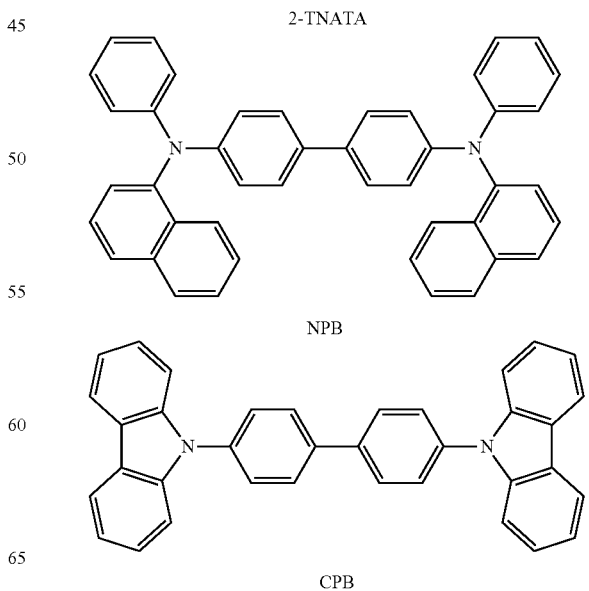

NPB

CPB

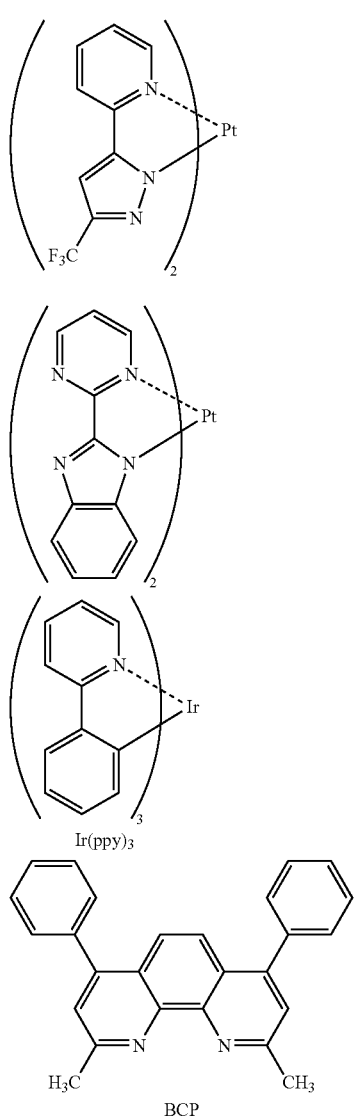

Compound A

Compound B

Ir(ppy)₃

BCP

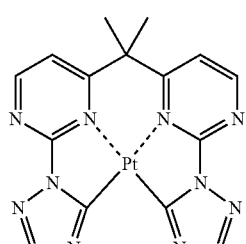

<Compound C>

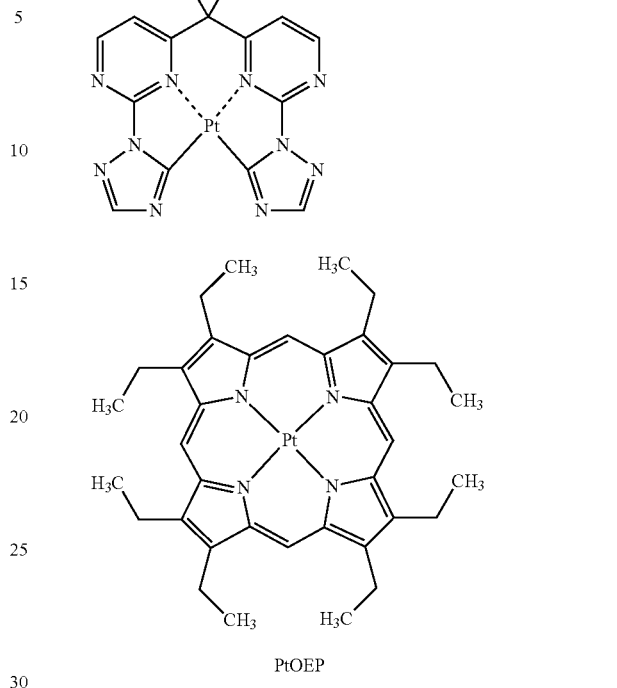

PtOEP

Evaluation Example 1

Driving voltages, current densities, luminance, efficiencies, and color purities of the organic light-emitting devices of Examples 1 to 10 and Comparative Examples 1 to 5 were measured using a PR650 (Spectroscan) Source Measurement Unit. (available from Photo Research, Inc.). In Table 1, $LT_{97}$ lifetime indicates the time taken until an initial luminance (assumed as 100%) measured at a current density of about 10 mA/cm² is reduced to 97%. The results are shown in Table 1 below.

TABLE 1

|  | Dopant | Driving voltage (V) | Current density (mA/cm²) | Luminance (cd/m²) | Efficiency (cd/A) | Emission color | Color coordinates | $LT_{97}$ (HR) |
|---|---|---|---|---|---|---|---|---|
| Example 1 | Compound 2 | 5.5 | 10 | 6,870 | 68.7 | Green | 0.27, 0.72 | 98 |
| Example 2 | Compound 4 | 5.6 | 10 | 6,782 | 67.8 | Green | 0.25, 0.70 | 92 |
| Example 3 | Compound 5 | 5.3 | 10 | 6,520 | 65.2 | Green | 0.27, 0.70 | 95 |
| Example 4 | Compound 10 | 5.5 | 10 | 6,810 | 68.1 | Green | 0.26, 0.71 | 93 |
| Example 5 | Compound 18 | 5.3 | 10 | 6,938 | 69.4 | Green | 0.25, 0.72 | 95 |
| Example 6 | Compound 20 | 5.3 | 10 | 6,972 | 69.7 | Green | 0.27, 0.72 | 98 |
| Example 7 | Compound 29 | 5.4 | 10 | 6,620 | 66.2 | Green | 0.25, 0.69 | 91 |
| Example 8 | Compound 15 | 5.9 | 10 | 3,042 | 30.4 | Red | 0.65, 034 | 107 |
| Example 9 | Compound 42 | 5.8 | 10 | 3,476 | 34.8 | Red | 0.64, 0.32 | 100 |
| Example 10 | Compound 43 | 5.9 | 10 | 3,351 | 33.5 | Red | 0.65, 0.33 | 102 |
| Comparative Example 1 | Ir(ppy)₃ | 6.8 | 10 | 4,766 | 47.7 | Green | 0.25, 0.70 | 61 |
| Comparative Example 2 | Compound A | 5.9 | 10 | 4,856 | 48.5 | Green | 0.25, 0.68 | 76 |
| Comparative Example 3 | Compound B | 6.3 | 10 | 5,510 | 55.1 | Green | 0.27, 0.70 | 55 |

TABLE 1-continued

| | Dopant | Driving voltage (V) | Current density (mA/cm$^2$) | Luminance (cd/m$^2$) | Efficiency (cd/A) | Emission color | Color coordinates | LT$_{97}$ (HR) |
|---|---|---|---|---|---|---|---|---|
| Comparative Example 4 | Compound C | 7.8 | 10 | 1,276 | 12.7 | Red | 0.53, 0.42 | 23 |
| Comparative Example 5 | PtOEP | 7.3 | 10 | 2,212 | 22.1 | Red | 0.67, 0.32 | 75 |

Referring to Table 1, the organic light-emitting devices of Examples 1 to 7 were found to have lower driving voltages, higher luminences, higher efficiencies, and better lifetime characteristics than the organic light-emitting devices of Comparative Examples 1 to 3. The organic light-emitting devices of Examples 8 to 10 were found to have lower driving voltages, higher luminances, higher efficiencies, and better lifetime characteristics than the organic light-emitting devices of Comparative Examples 4 and 5.

As described above, according to the one or more embodiments of the present invention, an organic light-emitting device including the organometallic compound of Formula 1 above may have a low driving voltage, a high efficiency, a high color purity, and a long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic compound represented by Formula A below:

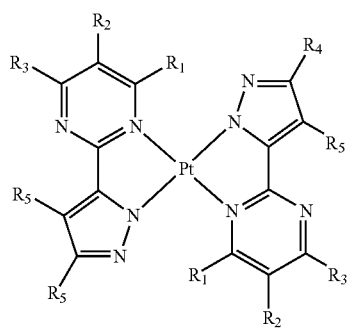

<Formula A>

$R_1$ to $R_5$ in Formula A being each independently one of a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), —C(=O)($Q_6$) (where $Q_1$ to $Q_6$ are each independently one of a hydrogen atom, a substituted or unsubstituted $C_1$-$C_{60}$ alkyl group, a substituted or unsubstituted $C_6$-$C_{60}$ aryl group and a substituted or unsubstituted $C_2$-$C_{60}$ heteroaryl group), and a binding site with an adjacent ligand via a divalent linking group, at least two substituents of $R_1$ to $R_5$ being optionally linked to each other to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group.

2. The organometallic compound of claim 1, $R_1$ to $R_5$ being each independently one of a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof; a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; a methyl group, an ethyl group, an n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group that are substituted with at least one of a deuterium atom, —F, a hydroxy group, a cyano group, and a nitro group; a phenyl group, a naphthyl group, an anthryl group, a fluorenyl group, a phenanthrenyl group, a chrysenyl group, a carbazolyl group, a pyridinyl group, a pyrimidinyl group, a pyrazinyl group, a triazinyl group, a quinolinyl group, and an isoquinolinyl group; and a phenyl group, a naphthyl group, an anthryl group, a fluorenyl group, a phenanthrenyl group, a chrysenyl group, a carbazolyl group, a pyridinyl group, a pyrimidinyl group, a pyrazinyl group, a triazinyl group, a quinolinyl group, and an isoquinolinyl group that are substituted with at least one of a deuterium atom, —F, a hydroxy group, a cyano group, a nitro group, -a methyl group, an ethyl group, a n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, a pentoxy group, a phenyl group, a naphthyl group, and an anthryl group.

3. The organometallic compound of claim 1, the organometallic compound being represented by one of Formulae 1A2, 1B2, 1C2, 1D2, 1E2, 1F2 and 1G2 below, <Formula 1A2>
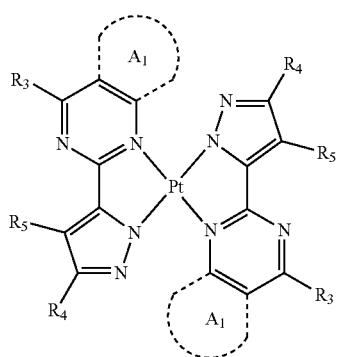

<Formula 1B2>
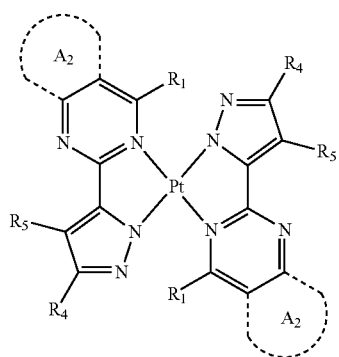

<Formula 1C2>
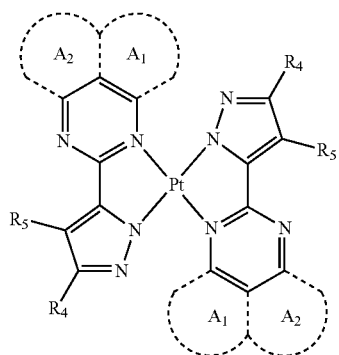

<Formula 1D2>
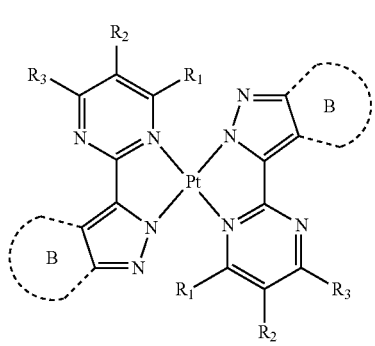

<Formula 1E2>
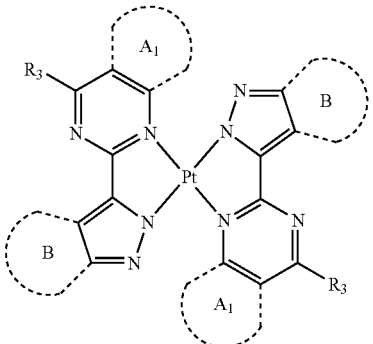

<Formula 1F2>
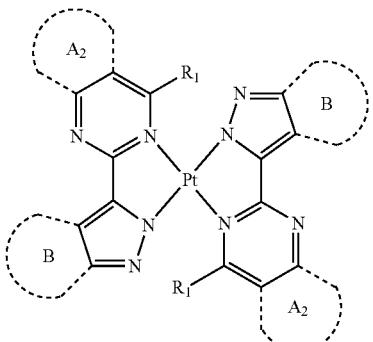

<Formula 1G2>
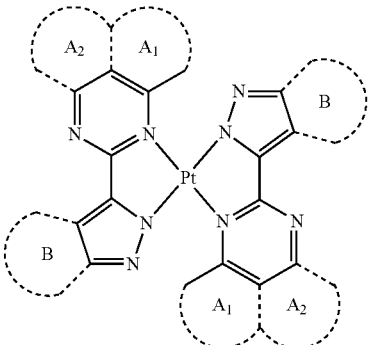

$R_1$ to $R_5$ in Formulae 1A2 to 1G2 being as defined in claim 1; and an $A_1$ ring, an $A_2$ ring, and a B ring are each independently one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

4. The organometallic compound of claim 3, the $A_1$ ring and the $A_2$ ring being each independently one of benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene; and benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene that are substituted with at least one of a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one hydrogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (where $Q_{11}$ to $Q_{15}$ are each independently one of a hydrogen atom, a $C_1$-$C_{10}$ alkyl group, a $C_6$-$C_{20}$ aryl group, and a $C_2$-$C_{20}$ heteroaryl group); and the B ring is one of cyclopropane, cyclobutane, cyclopentane, cyclohexane, cycloheptane, cyclooctane, cyclopentene, cyclopentadiene, cyclohexadiene, cycloheptadiene, bicycloheptane, bicyclooctane, benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene; and cyclopropane, cyclobutane, cyclopentane, cyclohexane, cycloheptane, cyclooctane, cyclopentene, cyclopentadiene, cyclohexadiene, cycloheptadiene, bicycloheptane, bicyclooctane, benzene, pentalene, indene, naphthalene, azulene, heptalene, indacene, acenaphthylene, fluorene, spiro-fluorene, phenalene, phenanthrene, anthracene, fluoranthene, triphenylene, pyrene, and chrysene that are substituted with at least one of a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one hydrogen atom, a $C_2$-$C_{60}$ alkenyl group, a $C_2$-$C_{60}$ alkynyl group, a $C_1$-$C_{60}$ alkoxy group, a $C_3$-$C_{70}$ cycloalkyl group, a $C_3$-$C_{70}$ cycloalkeny group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (where $Q_{11}$ to $Q_{15}$ are each independently one of a hydrogen atom, a $C_1$-$C_{10}$ alkyl group, a $C_6$-$C_{20}$ aryl group, and a $C_2$-$C_{20}$ heteroaryl group).

5. The organometallic compound of claim 1, the organometallic compound being a compound represented by one of Formulae 1A-(3), 1A-(4), 1B-(2), 1D-(4), 1D-(5), 1D-(6), 1F-(4), 1F-(5), and 1F-(6) below:

<Formula 1A-(3)>

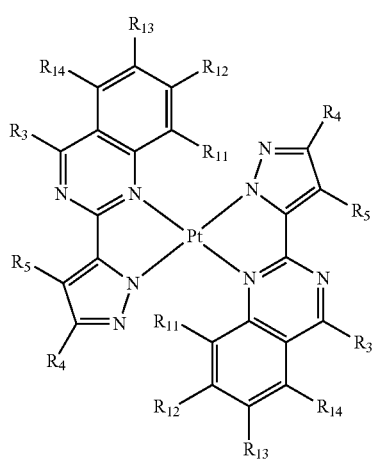

<Formula 1A-(4)>

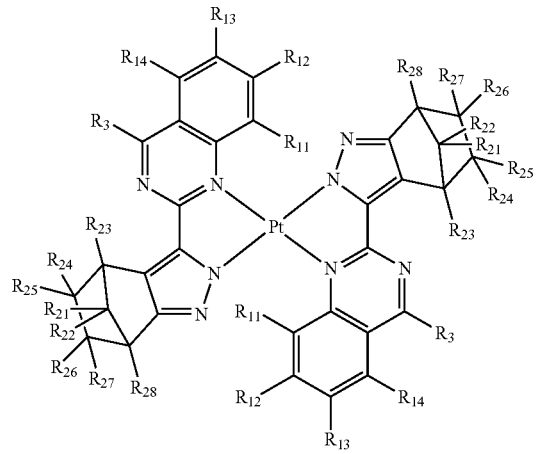

<Formula 1B-(2)>

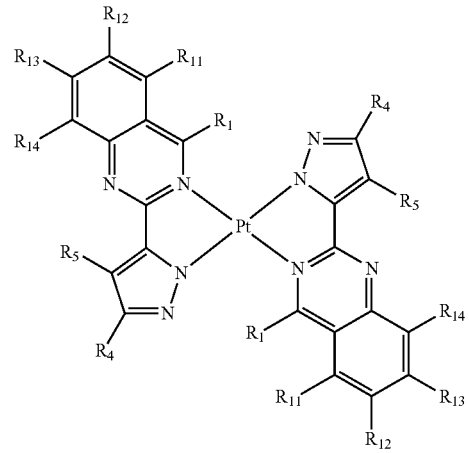

<Formula 1D-(4)>

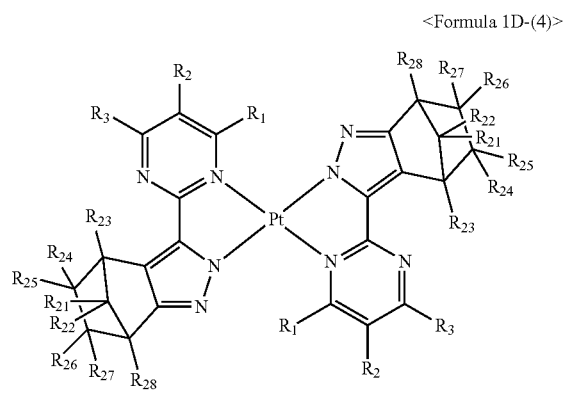

-continued

<Formula 1D-(5)>

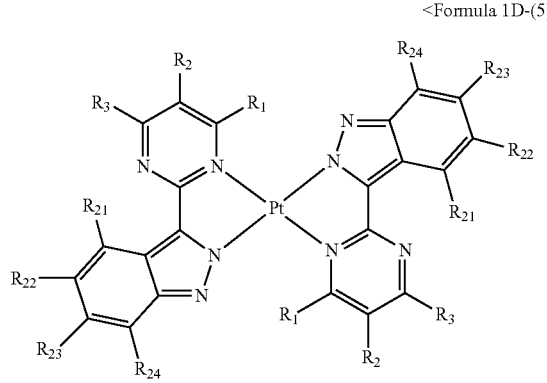

<Formula 1D-(6)>

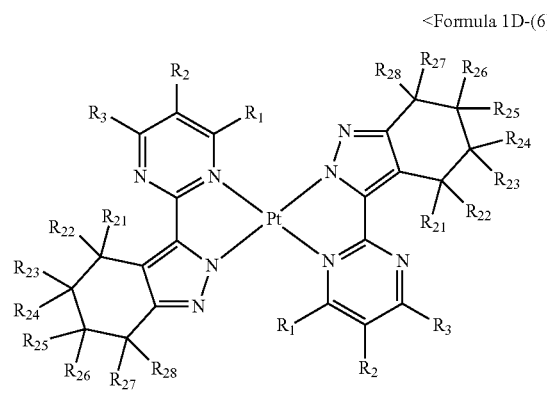

<Formula 1F-(4)>

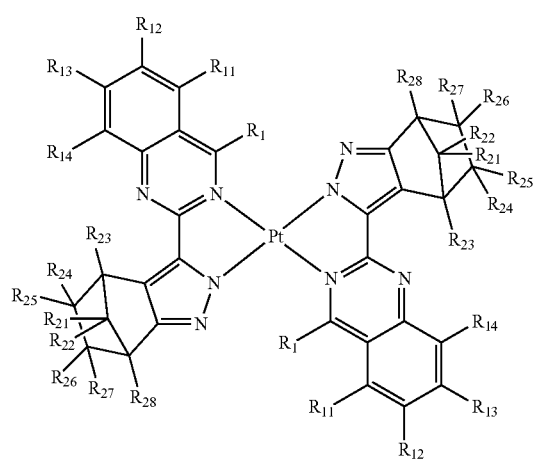

-continued

<Formula 1F-(5)>

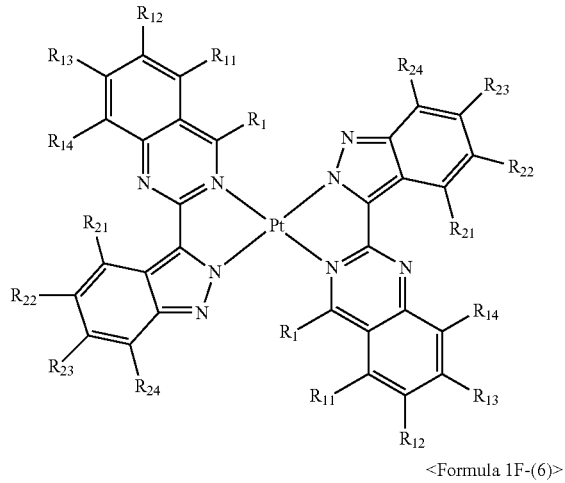

<Formula 1F-(6)>

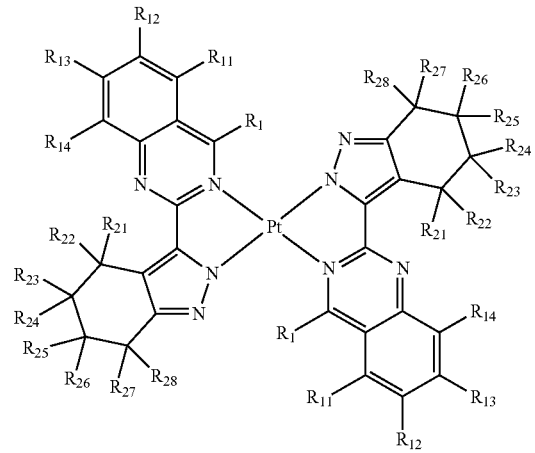

$R_1$ to $R_3$, $R_{11}$ to $R_{14}$, and $R_{21}$ to $R_{28}$ being each independently one of a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxy group, a cyano group, and a nitro group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxy group, a cyano group, a nitro group, a $C_1$-$C_{20}$ alkyl group, a $C_1$-$C_{20}$ alkoxy group, a phenyl group, an naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, and a triazinyl group.

6. The organometallic compound of claims 1,
$R_1$ to $R_5$ being each independently one of a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxy group, a cyano group, and a nitro group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxy group, a cyano group, a nitro group, a $C_1$-$C_{20}$ alkyl group, a $C_1$-$C_{20}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, and a triazinyl group.

7. The organometallic compound of claim 1, the organometallic compound being one of Compounds 1 to 32 below:

1
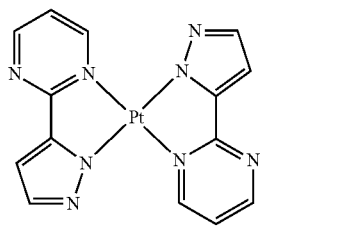

2
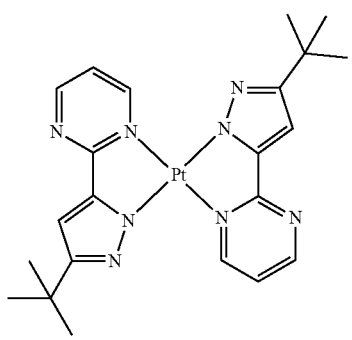

3
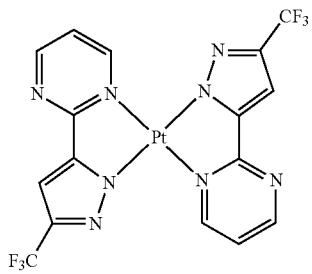

4
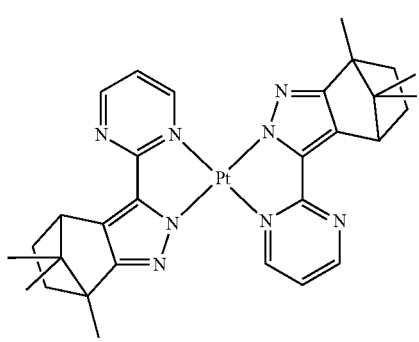

-continued

5
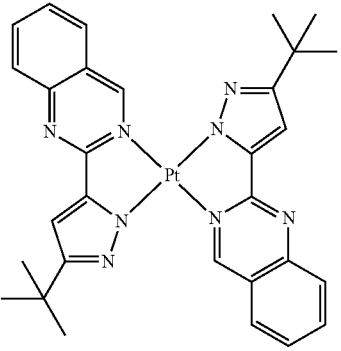

6
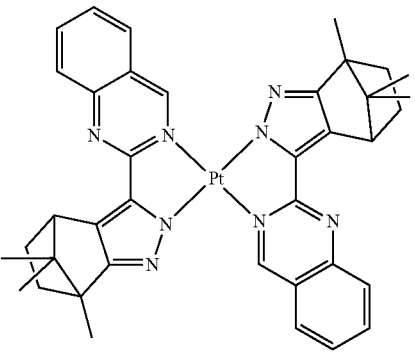

7
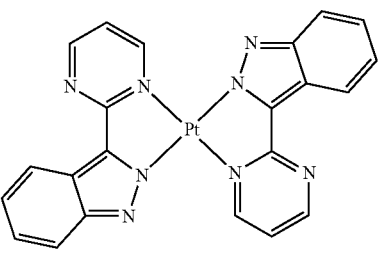

8
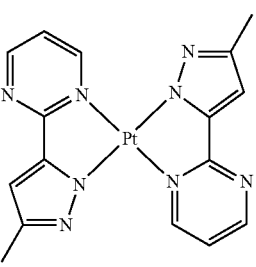

9
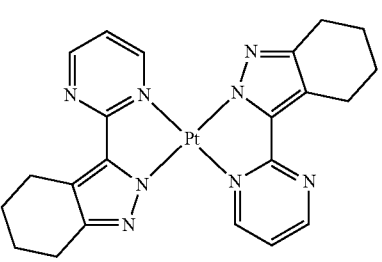

125
-continued
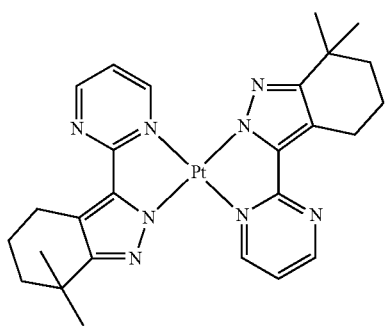
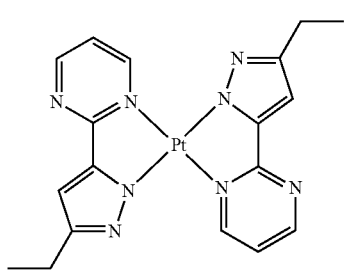
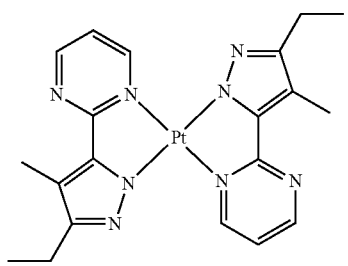
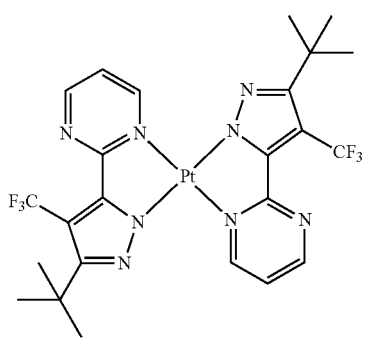
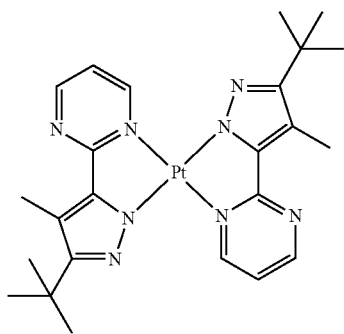
126
-continued
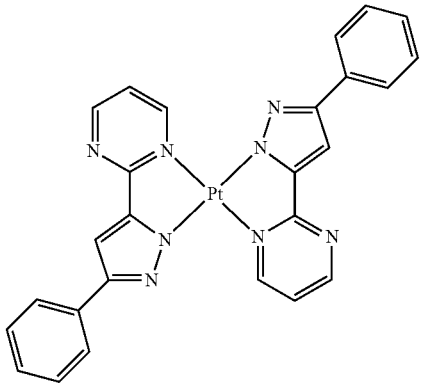
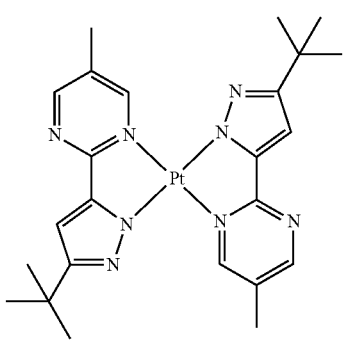
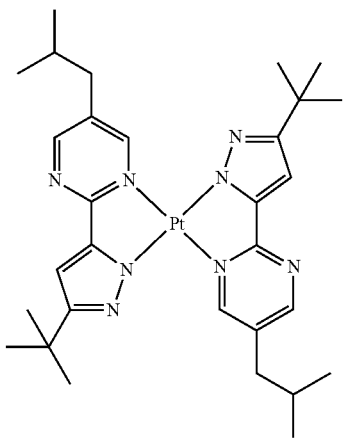
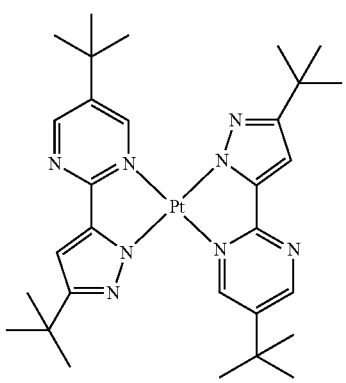

-continued
19
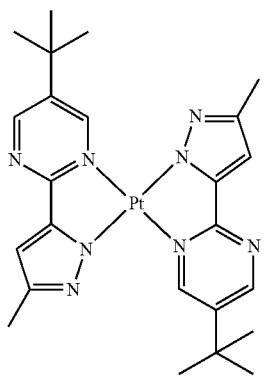
20
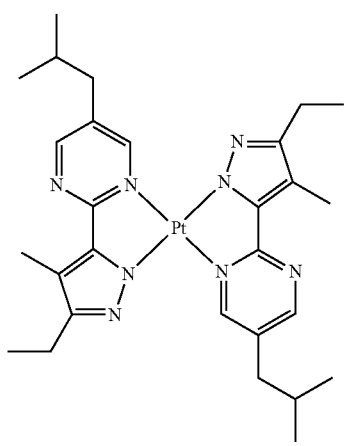
21
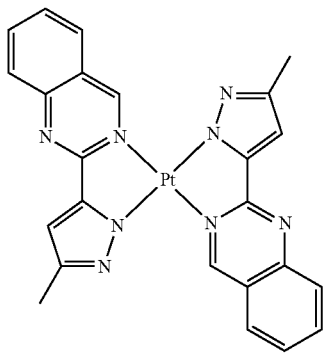
22
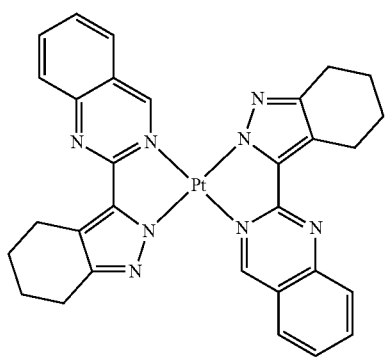
-continued
23
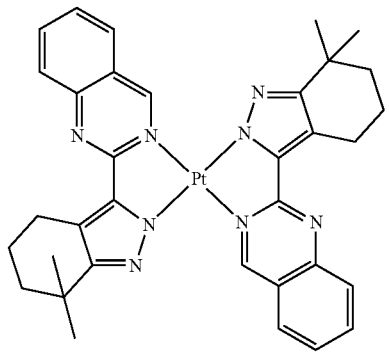
24
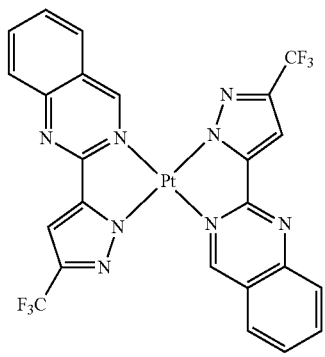
25
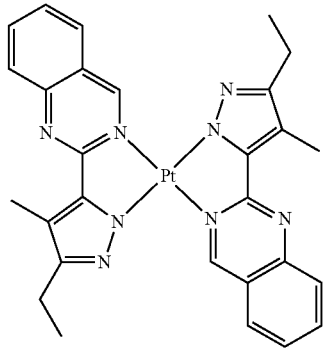
26
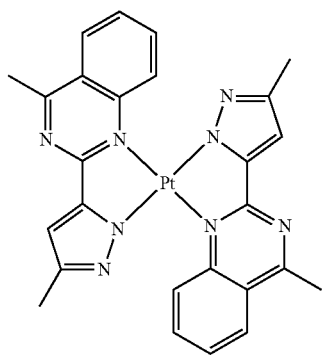

-continued

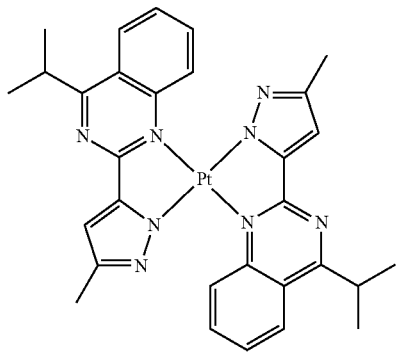
27

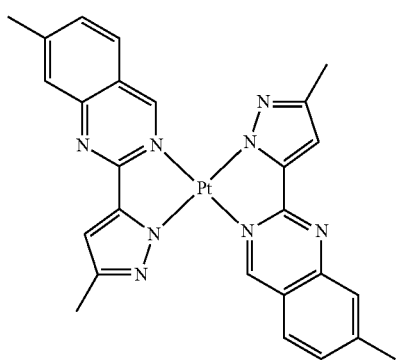
28

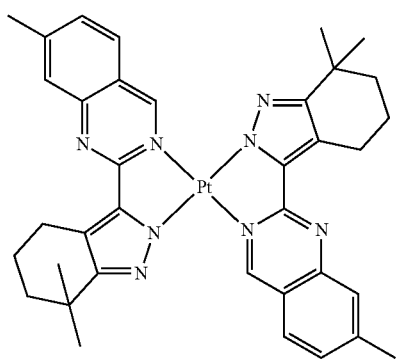
29

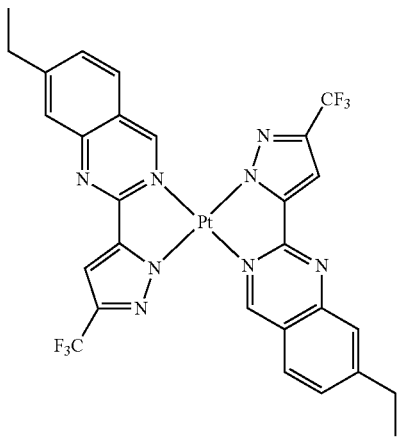
30

-continued

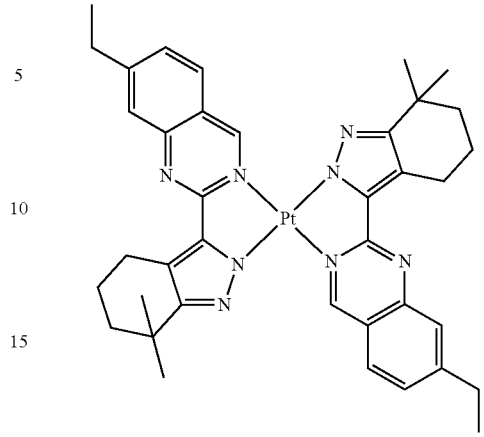
31

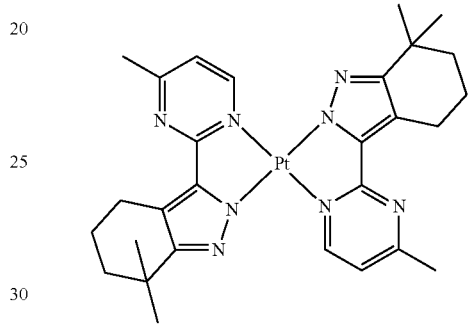
32

8. An organic light-emitting device comprising: a substrate; a first electrode; a second electrode disposed opposite to the first electrode; and an organic layer disposed between the first electrode and the second electrode and comprising an emission layer, the organic layer comprising at least one of the organometallic compounds of claim 1.

9. The organic light-emitting device of claim 8, the organic layer comprising at least one of a hole injection layer, a hole transport layer, a functional layer having both hole injection and hole transport capabilities, a buffer layer, and an electron blocking layer between the first electrode and the emission layer, and further comprising at least one of a hole blocking layer, an electron transport layer, and an electron injection layer between the emission layer and the second electrode.

10. The organic light-emitting device of claim 8, the emission layer comprising the organometallic compound, the emission layer emitting light based on the mechanism of phosphorescence; the organometallic compound in the emission layer serving as a dopant; and the emission layer further comprising a carbazole-based compound as a host.

11. The organic light-emitting device of claim 10, the carbazole-based compound being represented by Formula 10 below:

<Formula 10>

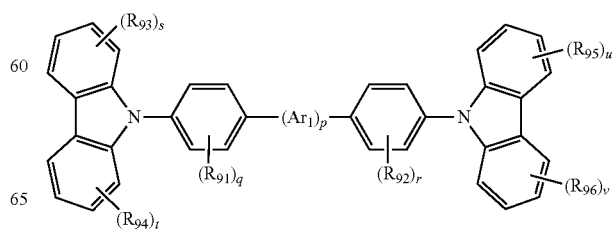

Ar$_1$ in Formula 10 being a substituted or unsubstituted C$_1$-C$_{60}$ alkylene group, a substituted or unsubstituted C$_2$-C$_{60}$ alkenylene group, —C(=O)—, —N(R$_{100}$)— (where R$_{100}$ is one of a substituted or unsubstituted C$_6$-C$_{60}$ aryl group, and a substituted or unsubstituted C$_2$-C$_{60}$ heteroaryl group), a substituted or unsubstituted C$_6$-C$_{60}$ arylene group, and a substituted or unsubstituted C$_2$-C$_{60}$ heteroarylene group;

p in Formula 10 being an integer from 0 to 10;

R$_{91}$ to R$_{96}$ in Formula 10 being each independently one of a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_3$-C$_{10}$ cycloalkenyl group, a substituted or unsubstituted C$_3$-C$_{10}$ heterocycloalkyl group, a substituted or unsubstituted C$_3$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, and a substituted or unsubstituted C$_2$-C$_{60}$ heteroaryl group, two adjacent substituents of R$_{91}$ to R$_{96}$ being optionally linked to form one of a substituted or unsubstituted C$_4$-C$_{20}$ alicyclic group, a substituted or unsubstituted C$_2$-C$_{20}$ heteroalicyclic group, a substituted or unsubstituted C$_6$-C$_{20}$ aromatic group, and a substituted or unsubstituted C$_2$-C$_{20}$ hetemaromatic group; and q, r, s, t, u, and v in Formula 10 being each independently an integer from 1 to 4.

12. The organic light-emitting device of claim 10, the carbazole-based compound being one of the following compounds:

H1
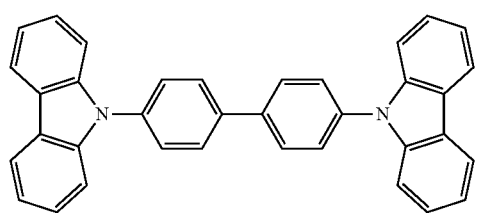

H2
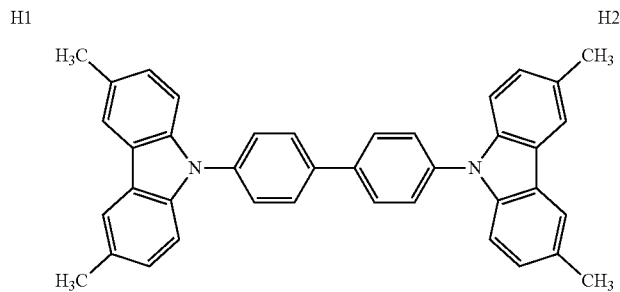

H3
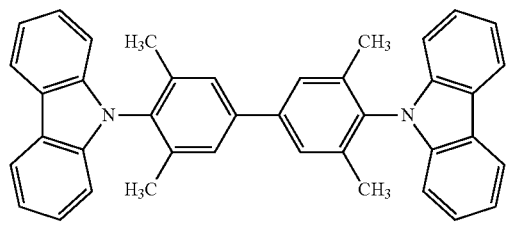

H4
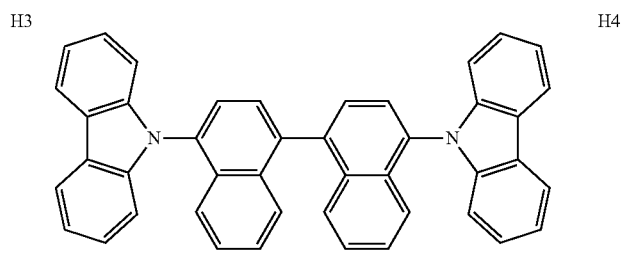

H5
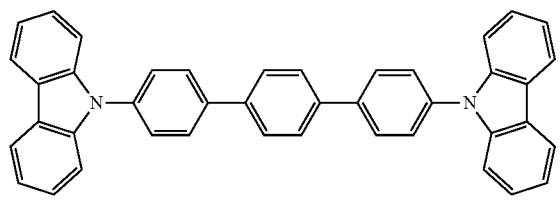

H6
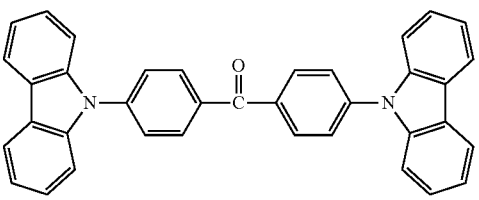

H7
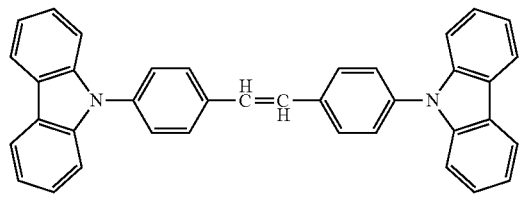

H8
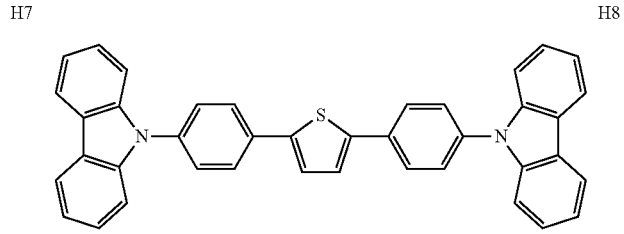

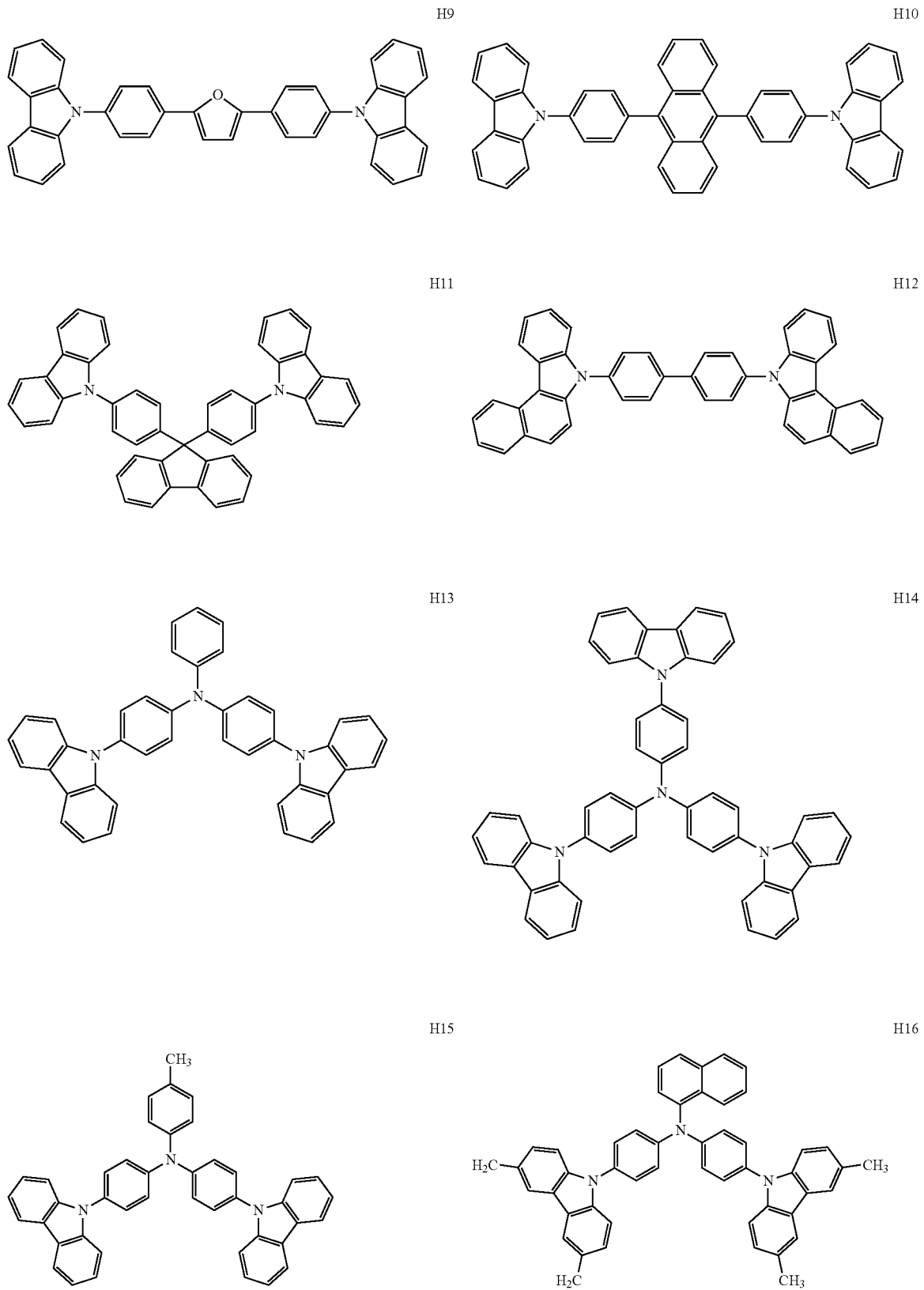

-continued
H17
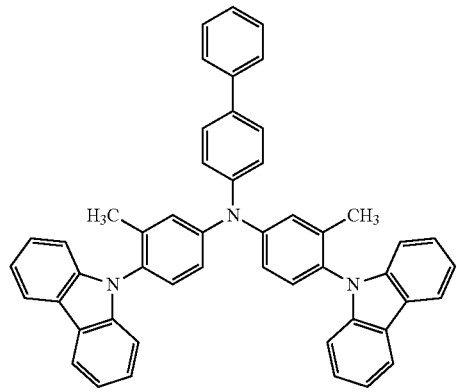
H18
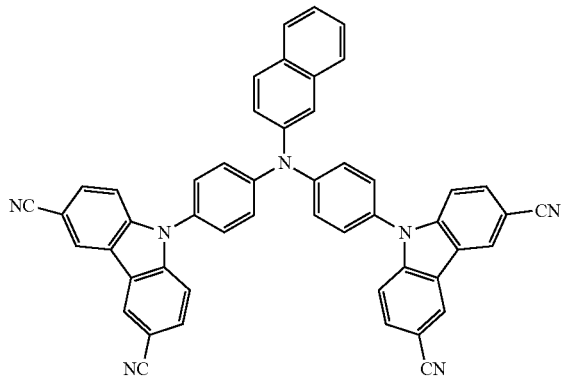
H19
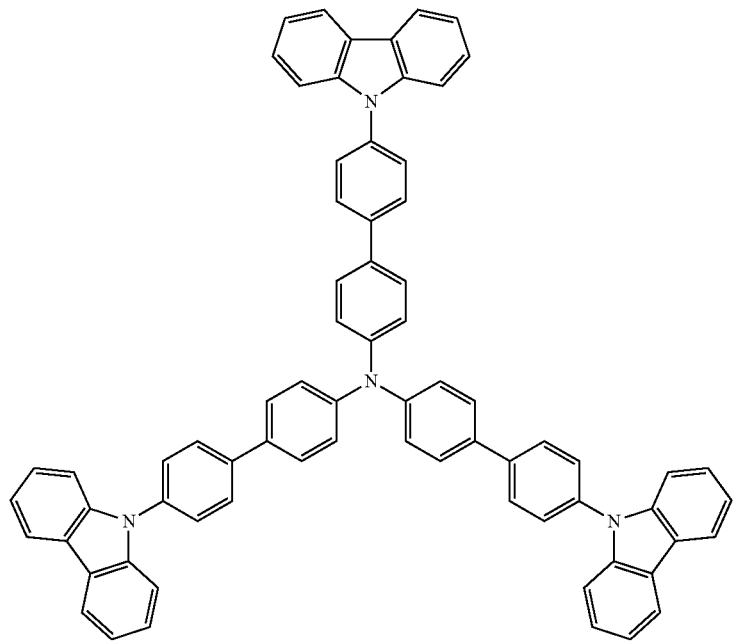
H20
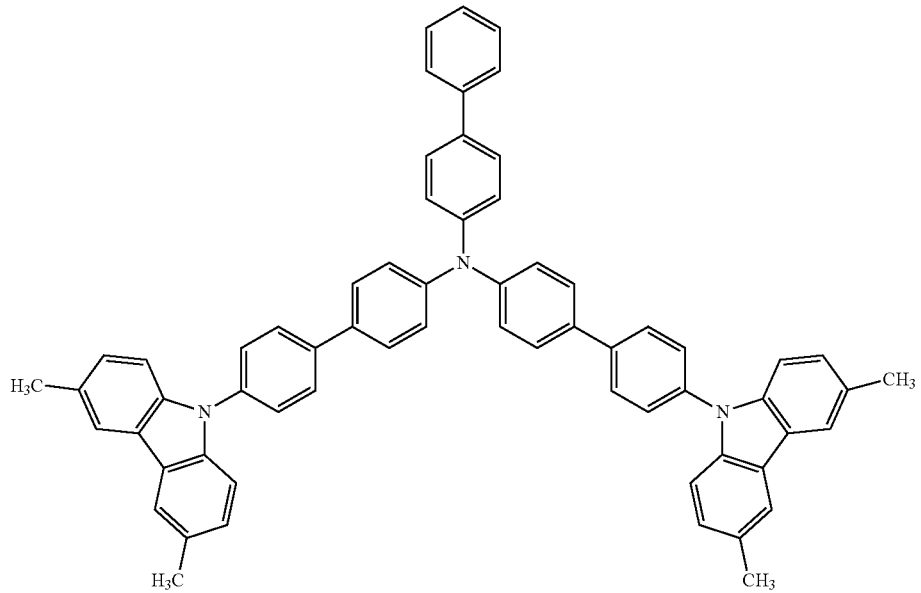

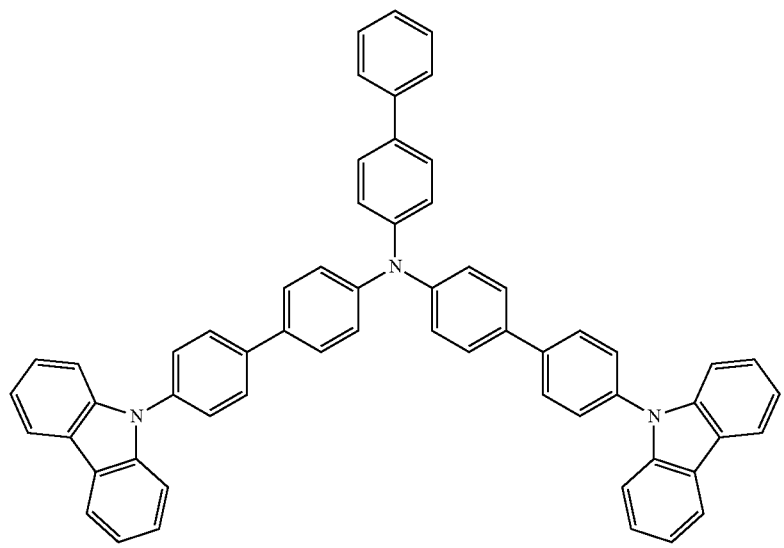
H21
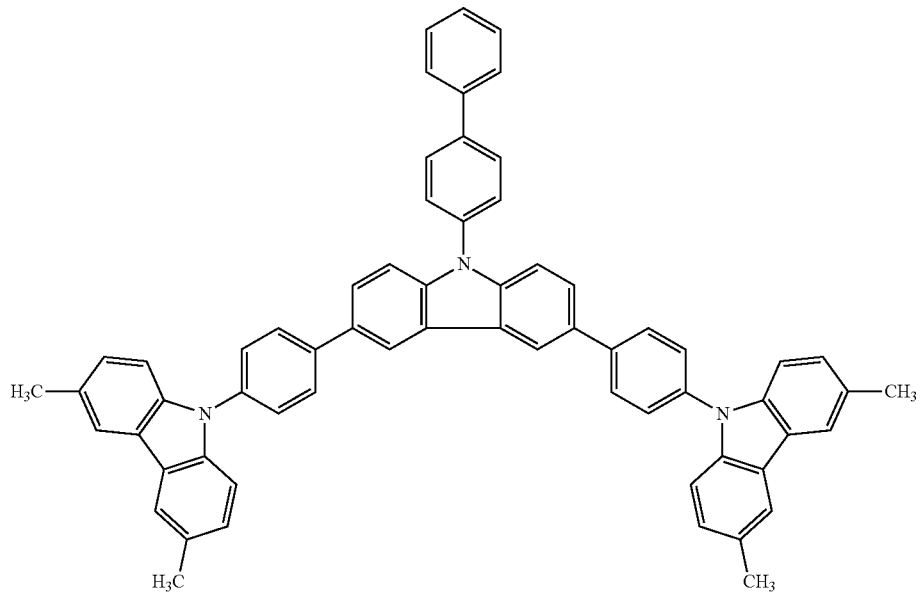
H22
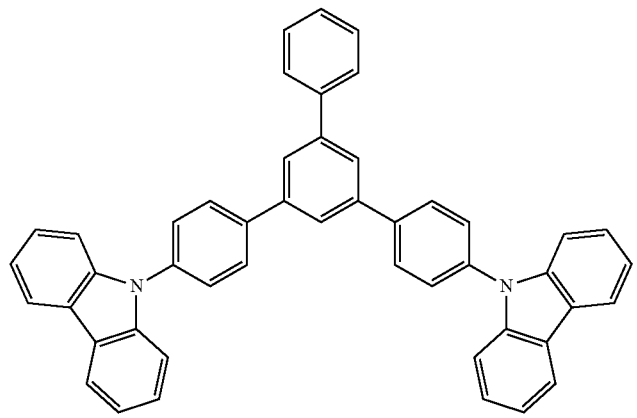
H23

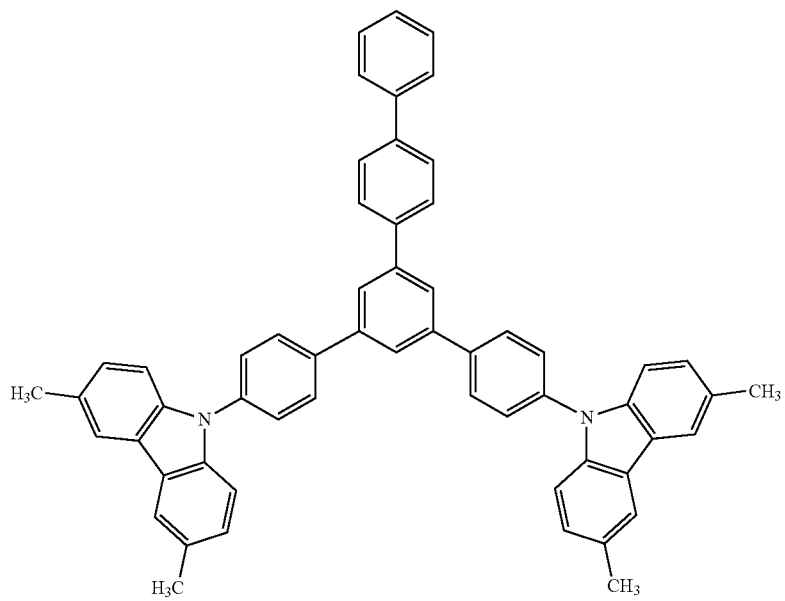
H24
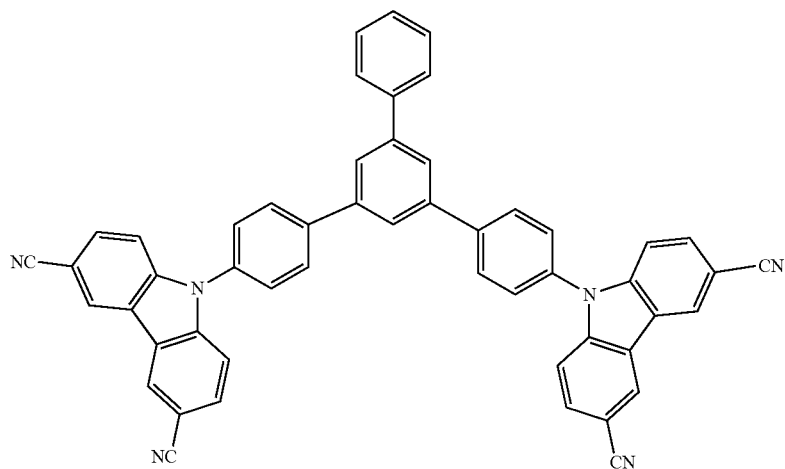
H25
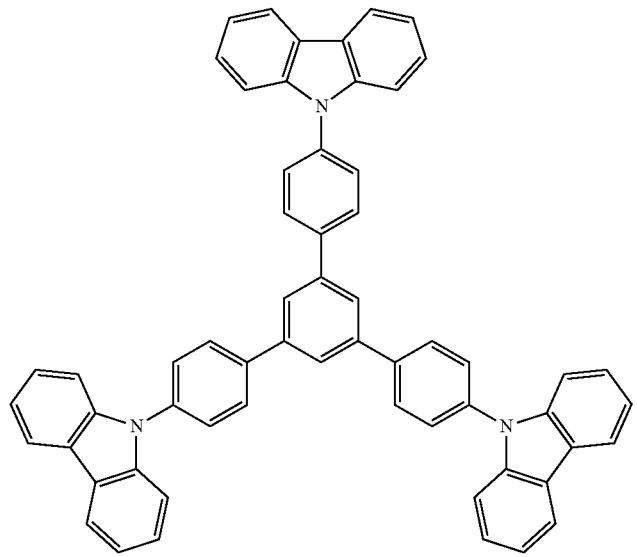
H26

-continued
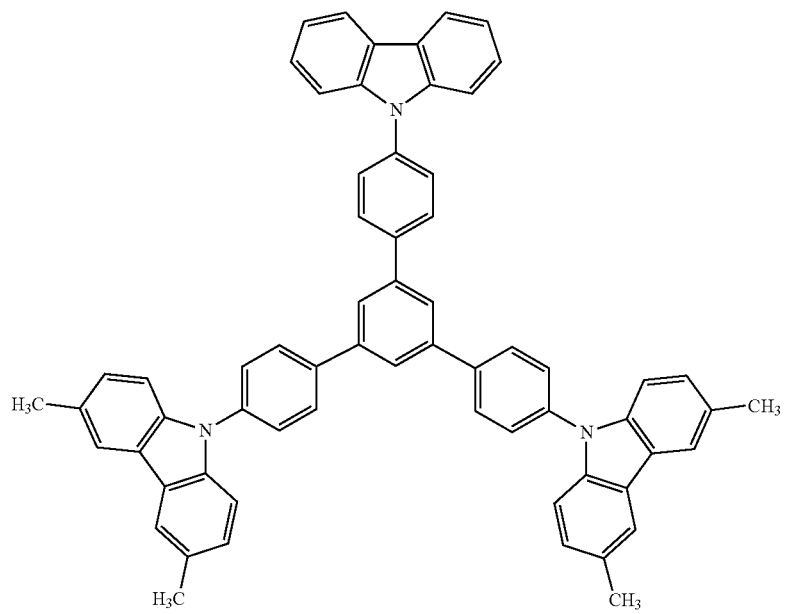
H27
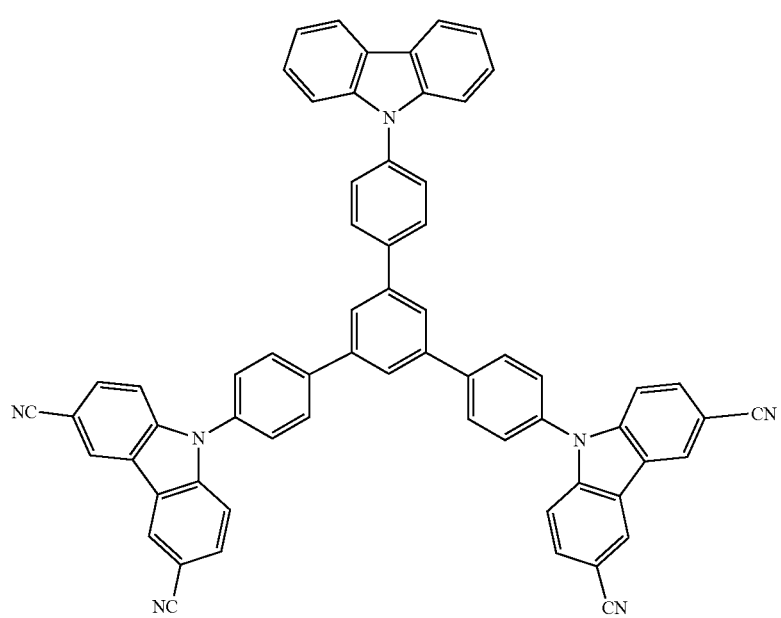
H28

-continued
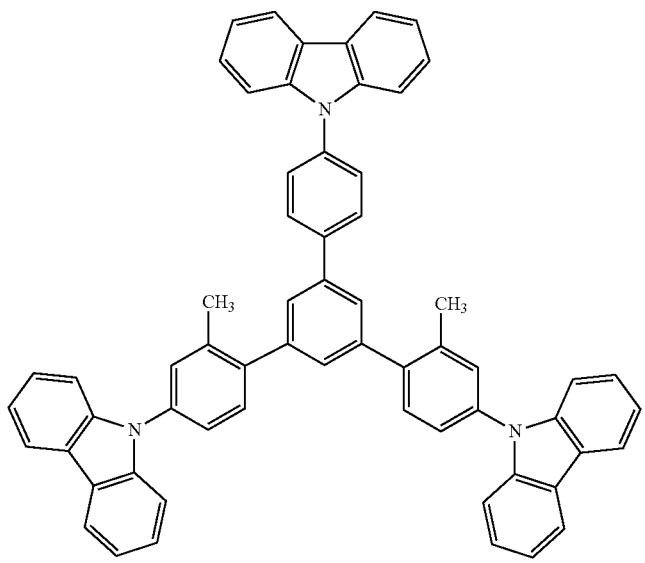
H29
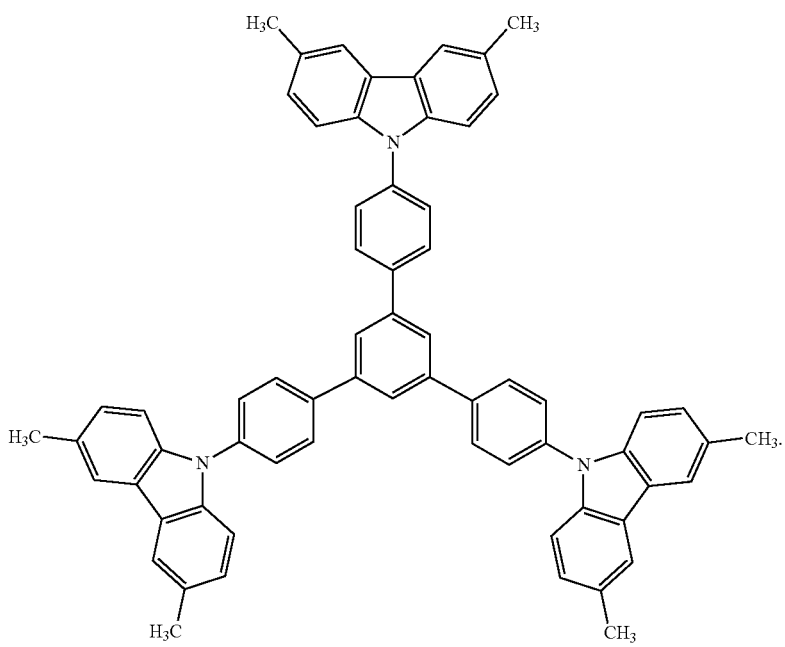
H30
* * * * *